(12) United States Patent
Zask et al.

(10) Patent No.: US 7,666,901 B2
(45) Date of Patent: Feb. 23, 2010

(54) ANALOGS OF 17-HYDROXYWORTMANNIN AS PI3K INHIBITORS

(75) Inventors: Arie Zask, New York, NY (US); Ping Cai, New City, NY (US); Jianxin Gu, River Edge, NJ (US); Joshua Kaplan, Nyack, NY (US); Ker Yu, Pine Brook, NJ (US); Tianmin Zhu, Monroe, NY (US)

(73) Assignee: Wyeth, Madison, NJ (US)

( * ) Notice: Subject to any disclaimer, the term of this patent is extended or adjusted under 35 U.S.C. 154(b) by 480 days.

(21) Appl. No.: 11/248,510

(22) Filed: Oct. 13, 2005

(65) Prior Publication Data

US 2006/0128793 A1 Jun. 15, 2006

Related U.S. Application Data

(60) Provisional application No. 60/617,654, filed on Oct. 13, 2004.

(51) Int. Cl.
*A61K 31/352* (2006.01)
*C07D 311/94* (2006.01)

(52) U.S. Cl. .................................. 514/453; 549/276
(58) Field of Classification Search ................ 549/276; 514/453
See application file for complete search history.

(56) References Cited

U.S. PATENT DOCUMENTS

| 5,378,725 A | 1/1995 | Bonjouklian et al. |
| 5,468,773 A | 11/1995 | Dodge et al. |
| 5,480,906 A * | 1/1996 | Creemer et al. ............. 514/453 |
| 6,670,348 B1 | 12/2003 | Rosen et al. |
| 6,703,414 B2 | 3/2004 | Powis et al. |
| 2003/0109572 A1 | 6/2003 | Powis |
| 2003/0194749 A1 | 10/2003 | Wandless et al. |
| 2006/0063824 A1* | 3/2006 | Kirkpatrick et al. ......... 514/422 |

FOREIGN PATENT DOCUMENTS

| GB | 2 302 021 A | 8/1997 |
| WO | WO 96/01108 | 1/1996 |
| WO | WO/01 00213 | 1/2001 |
| WO | WO/01 47921 | 7/2001 |
| WO | WO 03/024183 A2 | 3/2003 |
| WO | WO/03 030909 | 4/2003 |
| WO | WO 2004/024093 | 3/2004 |
| WO | WO 2004/093918 A2 | 11/2004 |

OTHER PUBLICATIONS

Creemer, L.C., et al., "Synthesis and in Vitro Evaluation of New Wortmannin Esters: Potent Inhibitors of Phosphatidylinositol 3-Kinase" (1996) *J. Med. Chem.*, vol. 39, No. 25, pp. 5021-5024.

De Luca, L., et al., "An Efficient Route to Alkyl Chlorides from Alcohols Using the Complex TCT/DMF" (2002) *Organic Letters*, vol. 4, No. 4, pp. 553-555.

Ihle, NT, et al., Abstract "95th Annual Meeting of the American Association for Cancer Research," Orlando, Florida, USA, Mar. 27-31, 2004.

Powis, G., et al., Abstract No. 4752 "Pharmacokinetic and pharmacodynamic studies of a novel antitumor wortmannin analogue inhibitor of phosphatidylinosito-3 kinase" Accession No. WD-2004-005811, Mar. 29, 2004.

Norman, B.H., et al., "Studies on the Mechanism of Phosphatidylinositiol 3-Kinase Inhibition by Wortmannin and Related Analogs," (1996)*J. Med. Chem.*, vol. 39, No. 5, pp. 1106-1111.

von Walter Haefliger, et al., Selektive Funktionalisierung von Wortmannin mit Hilfe einer Furanring-Maskierung, (1975) *Helvetica Chimica Acta*, vol. 58, No. 6. pp. 179-180.

Ihle, N.T., et al., "Molecular pharmacology and antitumor activity of PX-866, a novel inhibitor or phosphoinositide-3-kinase signaling" (1996) *Mol. Cancer Therapeutics*, vol. 3, No. 7,pp. 763-772 (2004).

Ihle, N.T., et al., "The phosphatidylinositol-3-kinase inhibitor PS-866 overcomes resistance to the epidermal growth factor receptor inhibitor gefitinib in A-549 human non-small cell lung cancer xenografts" *Mol. Cancer Therapeutics*, vol. 4, No. 9, pp. 1349-1357, (2005).

Pasut, G., et al., "Protein, peptide andnon-peptide drug PEGylation for therapeutic application," *Expert Opinion*, vol. 14, No. 6, pp. 859-894 (2004).

von Walter Haefliger, et al., "Einiunrung der Corticoid-Seitenkette bei Wortmannin," *Helvetica Chimica Acta*, vol. 58, No. 6. pp. 1629-1633, (1975).

Wipf, P., et al., "Synthesis and biological evaluation of synthetic viridins derived from C(20) -heteroalkylation of the steroidal PI-3-kinase inhibitor," *Org. Biomol. Chem.*, vol. 2, pp. 1911-1920, (2004).

* cited by examiner

*Primary Examiner*—Bernard Dentz
(74) *Attorney, Agent, or Firm*—David Rubin

(57) ABSTRACT

The present invention relates to compounds of formula I:

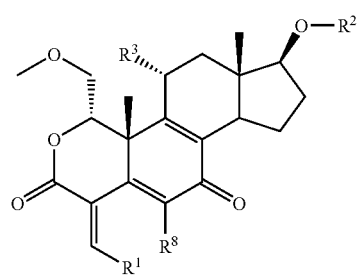

wherein $R^1$, $R^2$, $R^3$, and $R^8$ are defined herein.

15 Claims, 27 Drawing Sheets n=100-109

X is Br, Cl, or I and $R^{10}$ is $(CH_2)n$ or $-(CH_2)n-\langle\!\!\!\!\bigcirc\!\!\!\!\rangle-(CH_2)n-$, where n = 0-5.

PI3K inhibitor Compound 4 (referred to as "WAY-266175") in combination with the MEK inhibitors UO126 (5 µg/ml) (referred to as "UO") or 2-(2-chloro-4-iodoanilino)-N-(cycloprorylmethoxy-3,4-difluobenzamide) (referred to as "477") (1 µg/ml) synergistically inhibited growth of HCT116 colon tumor cells.

PI3K inhibitor compound 5 (referred to as "WAY-266176") in combination with the MEK inhibitors UO126 (5 µg/ml)(referred to as "UO") or 2-(2-chloro-4-iodoanilino)-N-(cycloprorylmethoxy-3,4-difluobenzamide) (referred to as "477") (1 µg/ml) synergistically inhibited growth of HCT116 colon tumor cells.

Compound 4 (referred to herein as "WAY-266175" or "175") in combination with 2-(2-chloro-4-iodoanilino)-N-(cycloprorylmethoxy-3,4-difluobenzamide) (referred to as either "WAY-176477" or "477") (1 µg/ml) demonstrated synergistic growth inhibitions in a panel of 7 colon tumor lines. Figure 18C shows compound 4 (+/-1 µg/ml WAY-176477) mean dose response inhibition curves of colon lines HCT116, HT29, SW620, SW480, LS-174T, Caco2 and Lovo.
Figure 18A
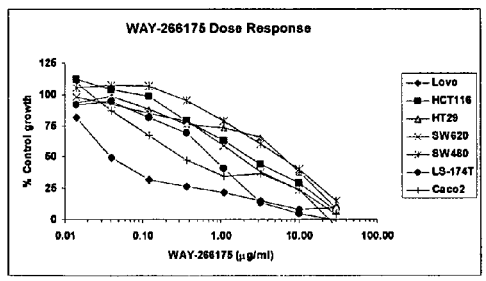
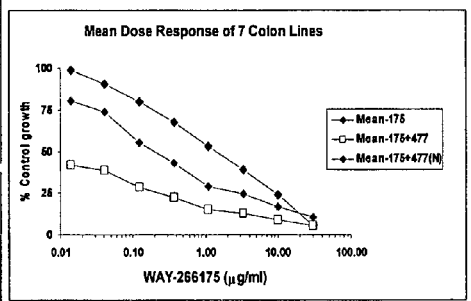
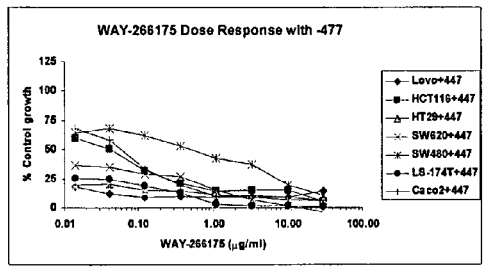
Figure 18B
Figure 18C Compound 4 (referred to herein as "WAY-266175") in combination with 2-(2-chloro-4-iodoanilino)-N-(cycloprorylmethoxy-3,4-difluobenzamide) (referred to as "477") (1 µg/ml) demonstrated synergistic growth inhibition in NSCLC lines A549 and H157.

Compound 4 (referred to herein as "WAY-266175" or "175") in combination with 2-(2-chloro-4-iodoanilino)-N-(cycloprorylmethoxy-3,4-difluobenzamide) (referred to as "WAY-176477") (1 µg/ml) demonstrated synergistic growth inhibition in MDA231 breast tumor cells. WAY-176477 in combination with compound 4 (0.1 µg/ml) demonstrated synergistic growth inhibition in DU145 prostate tumor cells.

Combination treatment of compound 4 (referred to as "WT-175") with MEK inhibitor 2-(2-chloro-4-iodoanilino)-N-(cycloprorylmethoxy-3,4-difluobenzamide) (referred to as "MEKI-477") synergistically induced apoptosis in HCT116 cells. Cells were treated for 24 hr.

provides Western blotting analysis of HCT116 cells on various molecular pathway markers of PI3K, MEK and cell cycle control. Cells were treated with single or combination agents for 16 hr. Compound 4 is referred to as "WAY-266175" and MEK inhibitor 2-(2-chloro-4-iodoanilino)-N-(cycloprorylmethoxy-3,4-difluobenzamide) (referred to as "WAW-176477").

HER2/Neu inhibitor (E)-N-{4-[3-chloro-4-(2-pyridinyl methoxy) anilino]-3-cyano-7-ethoxy-6-quinolinyl}-4-(dimethylamino)-2-butenamide (referred to as "HKI-272") in combination with Compound 4 (0.1 µg/ml) (referred to herein as "WAY-266175" or "175") synergistically inhibited growth of HER2/Neu-overexpressing MDA361-DYT2 breast tumor cells.

Western blot analysis of MDA361-DYT2 on various molecular pathway markers of PI3K, HER2/Neu, ERK and cell cycle control. Cells were treated for 16 hr. Compound 4 is referred to as "WAY-266175." HER2/Neu inhibitor (E)-N-{4-[3-chloro-4-(2-pyridinyl methoxy) anilino]-3-cyano-7-ethoxy-6-quinolinyl}-4-(dimethylamino)-2-butenamide is referred to as "HKI-272."

mTOR inhibitor CCI-779 in combination with Compound 4 (0.1 µg/ml)(referred to as "175" herein ) synergistically inhibited growth of MDA-MB-231 breast cells.

mTOR inhibitor CCI-779 in combination with Compound 4 (0.1 µg/ml) (referred to as "175") synergistically inhibited growth of colon tumor lines Caco2 and HCT116.

mTOR inhibitor CCI-779 in combination with Compound 4 (0.1 µg/ml) (referred to as "175") additively inhibited growth of PTEN-negative breast tumor lines MDA468 and BT-549.
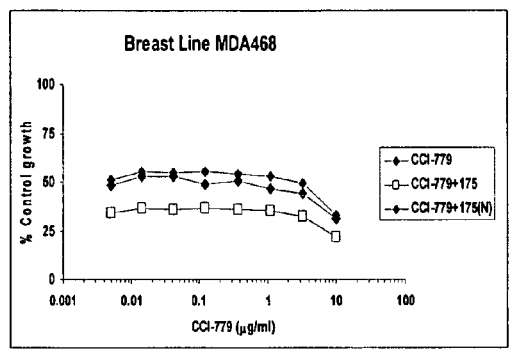
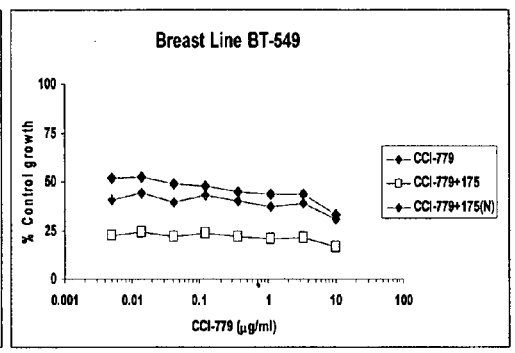
Figure 27A                    Figure 27B

ANALOGS OF 17-HYDROXYWORTMANNIN AS PI3K INHIBITORS

This application claims priority to provisional application U.S. 60/617,654, filed on Oct. 13, 2004, which is incorporated by reference in its entirety.

FIELD OF THE INVENTION

This invention relates to a series of 17-hydroxywortmannin analogs as PI3K inhibitors that have antitumor activity.

BACKGROUND OF THE INVENTION

Wortmannin is a fungal metabolite found to be a potent catalytic inhibitor of phosphatidylinositol-3(OH)-kinase (PI3K) and TOR kinase function within signal transduction pathways. (Norman, Bryan H., et al. (1996) "Studies on the Mechanism of the Phosphatidylinositol 3-Kinase Inhibition by Wortmannin and Related Analogs," *J. Med. Chem.*, 39, 1106-111 and Creemer, Lawrence C. (1996) "Synthesis and in Vitro Evaluation of New Wortmannin Esters: Potent Inhibitors of Phosphatidylinositol 3-Kinase," *J. Med. Chem.*, 39, 5021-5024).

Class-1a PI3K (referred to as PI3K) is a heterodimeric enzyme comprised of the p85 regulatory and p110 catalytic subunits. In response to growth factor receptor stimulation, PI3K catalyzes the production of the lipid second messenger phosphatidylinositol-3,4,5-triphosphate (PIP3) at the cell membrane. PIP3 in turn contributes to the activation of a wide range of downstream cellular substrates. The most critical signaling mediators downstream of PI3K include the serine/threonine kinase AKT and the mammalian target of rapamycin (mTOR). AKT confers a dominant survival signal and promotes proliferation via direct phosphorylation of multiple cell death/apoptosis proteins and cell cycle factors. mTOR is a central regulator of cell growth via controlling cellular protein translation. Thus, the PI3K/AKT/TOR pathway is critical for cell proliferation, growth, survival and angiogenesis.

In human cancer, deregulation in the PI3K/AKT/TOR pathway is among the most frequent events occurring in all major human tumors. Genetic loss of the tumor suppressor gene PTEN, a PIP3 phosphatase and a negative regulator of the PI3K signaling, is estimated to occur in 30-50% of all human cancers including lung, prostate, breast, brain, renal, melanoma, ovarian, endometrium, thyroid and lymphoid. In addition, constitutive elevation of PI3K expression has been associated with lung, ovarian and pancreatic cancers. Finally, cell surface oncogenes such as Her-2, EGFR and Ras cause constitutive PI3K signaling in breast, prostate, colon and lung tumors. These clinical data provide a strong rationale for exploring PI3K inhibitors as novel anticancer agents. (Cantley, L. and Neel, B. (1999) "New Insights into Tumor Suppression: PTEN Suppresses Tumor Formation by Restraining the Phosphoinositide 3-kinase/AKT pathway," *Proc. Natl. Acad. Sci. USA*, 96, 4240-4245). PI 3 kinase and TOR kinase have been shown to be active in cancer (Vivanco, I. and Sawyer, C. (2002) "The phosphatidylinositol 3-kinase-AKT Pathway in Human Cancer," *Nature Reviews Cancer*, 2, 489-501), iscaemic heart disease and restenosis (Shiojima, I. And Walsh, K. (2002) "Role of Akt Signaling in Vascular Homeostasis and Angiogenesis," *Circulation Research*, 90, 1243-1250 and Ruygrok P., et al. (2003) "Rapamycin in Cardiovascular Medicine," *Intern Med J.*, 33, 103-109), inflammation (Wymann, M., et al. (2003) "Phosphoinostide 3-kinase gamma: A Key Modulator in Inflammation and Allergy," *Biochem Soc Trans*, 31, 275-280 and Kwak, Yong-Geun, et al. (April 2003) "Involvement of PTEN in airway hyperresponsiveness and inflammation in bronchial asthma," *The Journal of Clinical Investigation*, 111:7, 1083-1092), platelet aggregation (Watanabe, N., et al. (March 2003) "Functional Phenotype of Phosphoinositide 3-kinase p85 (alpha) Null Platelets Characterized by an Impaired Response to GP VI Stimulation," Blood (epub)), sclerosis (Kenerson, H., et al. (2002) "Activated Mammalian Target of Rapamycin in the Pathogenesis of Tuberous Sclerosis Complex Renal Tumors," *Cancer Res.*, 62, 5645-5650), respiratory disorders (Kitaura, J., et al. (2000) "AKT-dependent Cytokine Production in Mast Cells," *J. Exp. Med.*, 192, 729-739 and Stewart A. (2001) "Airway Wall Remodeling and Hyper-responsiveness: Modeling Remodeling in vitro and in vivo," Pulm Pharmacol Ther, 14, 255-265), HIV (Francois, F. and Klotman, M. "Phosphatidylinositol 3-kinase Regulates Human Immunodeficiency Virus Type-1 Replication Following Viral Entry in Primary CD4(+) T Lymphocytes and Macrophages," *J. Virol.*, 77, 2539-2549), and bone resorption (Pilkington, M., et al. (1998) "Wortmannin Inhibits Spreading and Chemotaxis of Rat Osteoclasts in vitro," *J Bone Miner Res*, 13, 688-694).

PI3K exists as a tightly associated heterodimer of an 85 kDa regulatory subunit and 110 kDa catalytic subunit, and is found in cellular complexes with almost all ligand-activated growth factor receptors and oncogene protein tyrosine kinases (Cantley, L. C., et al., *Cell*, 64:281-302 (1991)). The 85 kDa regulatory subunit apparently acts as an adaptor of PI3K to interact with growth factor receptors and tyrosine phosphorylated proteins (Margolis, C., *Cell Growth Differ.*, 3:73-80 (1992)).

Although PI3K appears to be an important enzyme in signal transduction, with particular implications relative to mitogenesis and malignant transformation of cells, only a limited number of water-soluble drug-polymer conjugates have been identified as having inhibitory activity against PI3K (see, e.g., Matter, W. F., et al., *Biochem. Biophys, Res. Commun.*, 186: 624-631 (1992)). Contrary to the selective PI3K activity of the water-soluble drug-polymer conjugates used in the methods of the present invention, the bioflavinoid water-soluble drug-polymer conjugates used by Matter, et al., particularly quercetin and certain analogs thereof, inhibit PI3K and other kinases such as protein kinase C and PI 4-kinase (Id.).

U.S. Pat. No. 5,378,725, issued Jan. 3, 1995, provided a method for inhibiting PI3K in mammals using wortmannin or one of certain analogs thereof. One of the disadvantages of wortmannin is its toxicity to living creatures. Even in low dosages, wortmannin in pure form is often systemically dose limiting to laboratory animals.

The biosynthetic production of wortmannin is well known in the art and the derivatives are synthesized from wortmannin. (Dewald, Beatrice, et al. (1988) "Two Transduction Sequences Are Necessary for Neutrophil Activation by Receptor Agonists," *The Journal of Biological Chemistry*, Vol. 263, Issue of November 5, pp 16179-16184; Norman, Bryan H., et al. (1996) "Studies on the Mechanism of Phosphatidylinositol 3-Kinase Inhibition by Wortmannin and Related Analogs," *J. Med. Chem.*, 39, pp 1106-1111; Varticovski, L., et al. (2001) "Water-soluble HPMA copolymer-wortmannin conjugate retains phosphoinositide 3-kinase inhibitory activity in vitro and in vivo," *Journal of Controlled Release*, 74, pp 275-281), all hereby incorporated by reference.

A wortmannin derivative, 17β-Hydroxywortmannin prepared from the reduction of wortmannin with diborane, showed a 10-fold increase in activity relative to wortmannin and pushed the PI3K $IC_{50}$ into the subnanomolar range, with an $IC_{50}$ of 0.50 nM. However, antitumor activity of 17β-Hydroxywortmannin in the C3H mammary model showed no inhibition at a dose of 0.5 (mg/kg) and toxicity at a dose of 1.0 mg/kg. These findings lead the authors to conclude, "nucleophilic addition to the electrophilic C-21 position of wortmannin and related analogs is required for inhibitor potency and antitumor activity. Unfortunately, this mechanism appears to be linked to the observed toxicity" (Norman, Bryan H., et al. (1996) "Studies on the Mechanism of Phosphatidylinositol 3-Kinase Inhibition by Wortmannin and Related Analogs," *J. Med. Chem.*, 39, 1106-1111, 1109-1110).

Wortmannin derivatives acetylated at the C-17 hydroxyl group showed a dramatic loss in activity leading the authors to conclude, "the active site cannot accommodate liphophilicity or steric bulk at C-17" (Creemer, Lawrence C., et al. (1996) "Synthesis and in Vitro Evaluation of New Wortmannin Esters: Potent Inhibitors of Phosphatidylinositol 3-Kinase," *J. Med. Chem.*, 39, 5021-5024, 5022). This conclusion is consistant with the X-ray crystallographic structure of PI3K bound to wortmannin subsequently elucidated (Walker, Edward H., et. al (2000) "Structural Determinants of Phosphoinositide 3-Kinase Inhibition by Wortmannin, LY294002, Quercetin, Myricetin, and Staurosporine," *Molecular Cell*, 6(4), 909-919).

Other wortmannin derivatives are opened at C-20. By reacting wortmannin with nucleophiles at the C-20 position, the furan ring is opened. Such ring-opened compounds demonstrate a range of biological activities (Wipf, Peter, et al. (2004) "Synthesis and biological evaluation of synthetic viridins derived from C(20)-heteroalkylation of the steroidal PI-3-kinase inhibitor wortmannin," *Org. Biomol. Chem.*, 2, 1911-1920). See also U.S. 2003/0109572 to Powis.

Attaching poly(ethyleneglycol) (PEG) has been successfully employed in medicinal chemistry to improve the aqueous solubility and administration of drugs. (Id.) However, covalently attaching PEG does not necessarily offer improvement in water solubility and availability of the drug to which it is attached (Bebbington, David, et al. (2002) "Prodrug and Covalent Linker Strategies for the Solubilization of Dual-Action Antioxidants/Iron Chelators," *Bioorganic & Medicinal Chemistry Letters*, 12, 3297-3300, 3299) and (Feng, Xia, et al. (2002) "Synthesis and Evaluation of Water-Soluble Paclitaxel Prodrugs," *Bioorganic & Medicinal Chemistry Letters*, 12, 3301-3303, 3302).

In an overview of PEG drugs, no low molecular weight (<20,000) PEG small molecule drug conjugates, prepared over a 20-year period, have led to a clinically approved product (Greenwald, R. B. (2001) "PEG drugs: an overview," *Journal of Controlled Release*, 74, pp 159-171, abstract). In fact only a few small organic molecule anticancer agents have been conjugated to PEG with permanent bonds, and those did not lead to clinically superior water-soluble drug-polymer conjugates (Greenwald, R. B., et al. (2003) "Effective Drug Delivery by PEGylated Drug Conjugates," *Advanced Drug Delivery Reviews*, 55, pp 217-250, 220). Using PEG-CPT, lethality was demonstrated to be approximately 50%, 10% and 0% for the PEG-CPT 40,000, 20,000 and 8,000 constructs. Ostensibly, employing polymer $M_w$ 5000 to conjugate drugs gave rapidly excreted species that would have little or no effect in vivo (Id., 225). That is not to say the attachment of PEG 40,000 with its ability to accumulate in tumors will automatically permit drugs to have greater antitumor activity (Id., 235).

There is a need for wortmannin analogs with improved antitumor activity and/or low toxicity. Compounds of the present invention fulfill this need.

SUMMARY OF THE INVENTION

In one embodiment, the present invention provides a compound of formula I:

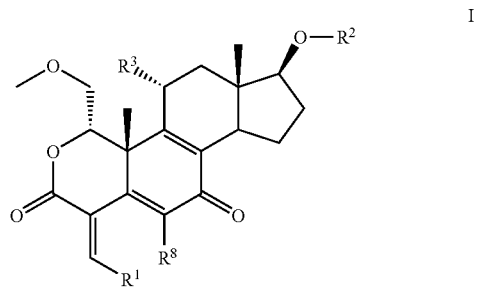

wherein:
$R^1$ is selected from the group consisting of $NR^4R^5$, $SR^6$, and $OR^7$;
$R^2$ is selected from the group consisting of hydrogen, formyl, and acyl;
$R^3$ is selected from the group consisting of hydrogen, hydroxy, alkoxy, alkanoyloxy, =O, acyloxy and carbonyl;
$R^4$ and $R^5$ are independently selected from the group consisting of hydrogen, hydroxyl, alkyl, alkenyl, heterocyclic, aryl, heteroaryl, aralkyl, and PEG; and wherein $R^4$ and $R^5$ are optionally joined to form a ring;
$R^6$ is selected from the group consisting of alkyl, aryl, heteroaryl, aralkyl, and PEG; and
$R^7$ is selected from the group consisting of hydrogen, alkyl, aryl, heteroaryl, aralkyl, and PEG;
$R^8$ is selected from the group consisting of hydroxy, acyloxy, and alkoxy;
and salts, solvates, and hydrates thereof.

In one embodiment, $R^1$ is $NR^4R^5$.
In one embodiment, $R^2$ is hydrogen.
In another embodiment, $R^2$ is a formyl group.
In yet another embodiment, $R^3$ is an acyloxy group. Preferably, $R^3$ is an acetoxy group.
In one embodiment, $R^8$ is a hydroxy group.
In one embodiment, the present invention provides a compound of formula I, wherein:
$R^1$ is selected from the group consisting of $NR^4R^5$, $SR^6$ and $OR^7$;
$R^2$ is selected from the group consisting of hydrogen and formyl;
$R^3$ is selected from the group consisting of hydrogen, hydroxy, and acyloxy;
$R^4$ and $R^5$ are independently selected from the group consisting of hydrogen, alkyl, alkenyl, heterocyclic, aryl, aralkyl, and PEG; and wherein $R^4$ and $R^5$ are optionally joined to form a ring;
$R^6$ is an alkyl group;
$R^7$ is hydrogen;
$R^8$ is a hydroxy-group
and salts, solvates, and hydrates thereof.

In one embodiment, the present invention provides exemplary compounds of formula I. One example is (1E,4S,4aR, 5R,6aS,7S)-1-{[[3-(dimethylamino)propyl](methyl)amino] methylene}-7,11-dihydroxy-4-(methoxymethyl)-4a,6a-dimethyl-2,10-dioxo-1,2,4,4a,5,6,6a,7,8,9,9a,10-dodecahydroindeno[4,5-h]isochromen-5-yl acetate.

The present invention also encompasses PEGylated compounds of formula I wherein the R groups are described as above. Examples include, but are not limited to compounds PEGylated at position $R^1$, $R^2$, or $R^3$.

In another embodiment, the present invention provides a method of inhibiting PI3K activity by providing a compound of the present invention. The present invention also provides a method of inhibiting PI3K in mammals, particularly humans, comprising administering a compound of the present invention. The present invention also provides a method of treating a PI3K-dependent condition comprising administering a compound of the present invention.

The present invention also provides methods of inhibiting TOR activity by providing a compound of the present invention. The present invention also provides a method of inhibiting TOR in mammals, particularly humans, comprising administering a compound of the present invention.

The present invention also provides pharmaceutical compositions comprising a compound of the present invention and a pharmaceutically acceptable carrier. The present invention provides a method of treating cancer comprising administering a pharmaceutical composition of the present invention. The present invention also provides methods further comprising administering one or more agents that modulate growth factor signaling, cytokine response, and cell cycle control.

BRIEF DESCRIPTION OF THE FIGURES

FIGS. 18A-C show that compound 4 in combination with 2-(2-chloro-4-iodoanilino)-N-(cycloprorylmethoxy-3,4-difluobenzamide) (an MEK inhibitor) demonstrated synergistic growth inhibition in a panel of seven colon tumor lines.

FIGS. 27A and B show that mTOR inhibitor CCI-779 in combination with compound 4 (0.1 µg/ml) synergistically inhibited growth of PTEN-negative breast tumor cell lines.

Figure 1:
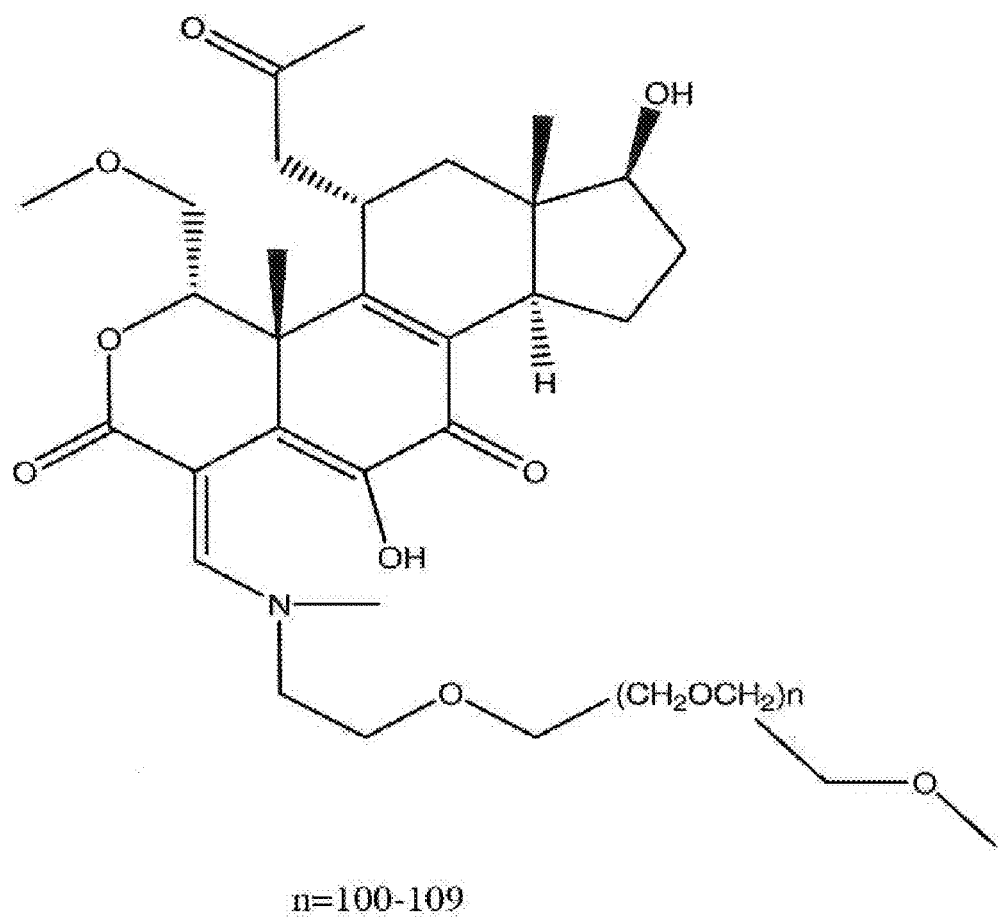
FIG. 1 depicts a PEGylated 17-hydroxywortmannin compound.

In the event of a conflict between the name and the structure of a compound, the structure takes precedence.

DETAILED DESCRIPTION OF THE INVENTION

In one embodiment, the present invention provides a compound of formula I:

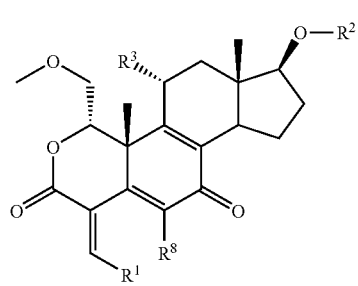

wherein:
$R^1$ is selected from the group consisting of $NR^4R^5$, $SR^6$, and $OR^7$;
$R^2$ is selected from the group consisting of hydrogen, formyl, and acyl;
$R^3$ is selected from the group consisting of hydrogen, hydroxy, alkoxy, alkanoyloxy, =O, acyloxy and carbonyl;
$R^4$ and $R^5$ are independently selected from the group consisting of hydrogen, hydroxyl, alkyl, alkenyl, heterocyclic, aryl, heteroaryl, aralkyl, and PEG; and wherein $R^4$ and $R^5$ are optionally joined to form a ring;

$R^6$ is selected from the group consisting of alkyl, aryl, heteroaryl, aralkyl, and PEG; and $R^7$ is selected from the group consisting of hydrogen, alkyl, aryl, heteroaryl, aralkyl, and PEG;

$R^8$ is selected from the group consisting of hydroxy, acyloxy, and alkoxy;

and salts, solvates, and hydrates thereof, provided that the compound is not a compound of formula V:

V wherein $R^9$ is alkyl, or a drug-polymer conjugate of a single non-repeating formula (B):

B wherein $R^{10}$ is —O—, —NH—, or —S—;
$R^{11}$ is alkyl, a cycloalkyl, or aryl;
$R^3$ is H, =O, —O—COC$_4$H$_9$, or OR$^{12}$;
$R^{12}$ is H, COR$^{13}$ or alkyl;
$R^{13}$ is alkyl, H, aryl, or —CH$_2$-aryl; and
n is 1-1000.

The R groups of the present invention are optionally substituted. Optionally substituted means having zero, one, or more than one substituent. Substituents include, but are not limited to, hydrogen, halogen, alkyl, alkenyl, alkynyl, hydroxy, alkoxy, acyl, alkylamino, arylamino, arylalkylamino, amino, cyano, carbamoyl, acetamido, carboxy, carbalkoxy, sulfonyl, PEG (polyethylene glycol), heterocyclic, aryl, aralkyl, heteroaryl, polycyclic groups, aryloxy, alkylthio, and arylthio groups. Substituents themselves may also be optionally substituted.

Unless otherwise specified, alkyl, alkenyl, and alkynyl groups have 1 to 10 carbon atoms and may be straight, branched, or cyclic.

Examples of heterocyclic groups include, but are not limited to pyrrolidine, piperidine, piperazine, oxopiperidine, morpholine, and azetidine. Examples of a benzene ring fused to a heterocyclic ring include, but are not limited to quinoline, isoquinoline, and dihydroisoquinoline. Unless otherwise specified, the heterocyclic groups contain one or more heteroatoms selected from the group consisting of nitrogen, oxygen, and sulfur.

Examples of aryl groups include, but are not limited to phenyl and naphthyl groups.

A polycyclic group comprises one ring fused to one or more other rings. The rings can be aromatic or non-aromatic. The rings can be hydrocarbon or heterocyclic rings.

Formyl means the radical —C(O)H.

Acyl means an organic radical derived from and organic acid by the removal of the hydroxyl group; e.g. R C(O)— is the acyl radical of R CO OH.

Alkoxy means a group —OR, wherein R is an alkyl, alkenyl, or alkynyl group which can optionally be substituted with one or more functional groups.

Carbonyl means carbon bonded to oxygen with a double bond, i.e., C=O.

Acyloxy refers to the groups alkyl-C(O)O—, substituted alkyl-C(O)O—, cycloalkyl-C(O)O—, substituted cycloalkyl-C(O)O—, aryl-C(O)O—, heteroaryl-C(O)O—, and heterocyclic-C(O)O—. Acyloxy includes alkanoyloxy, alkenoyloxy and aroyloxy.

Heteroaryl means an aromatic heterocycle ring, including both mono- bi- and tricyclic ring systems, wherein at least one carbon atom of ring system is replaced with a heteroatom independently selected from nitrogen, oxygen and sulfur.

Aralkyl is an arylated alkyl, which is a radical in which an alkyl H atom is substituted by an aryl group.

PEG is polyethylene glycol.

In one embodiment, $R^1$ is $NR^4R^5$. In some embodiments, $R^4$ and $R^5$ are joined to form a ring. For example, embodiments include, but are not limited to those wherein $R^4$ and $R^5$ are joined such that $NR^4R^5$ is pyrrolidine, piperidine, piperazine, oxopiperidine, morpholine, or azetidine. The $NR^4R^5$ ring may be optionally substituted as described above. The $NR^4R^5$ ring may also be fused to a benzene ring such that $NR^4R^5$ is, for example, dihydroisoquinoline.

In another embodiment, $R^1$ is $SR^6$. Examples include, but are not limited to butylsulfanyl.

In another embodiment, $R^1$ is $OR^7$. Examples include, but are not limited to —OH.

In formula I, $R^1$ is depicted as having one particular structural relationship with respect to C20 of the wortmannin compound. One skilled in the art will recognize that other possible geometries of the C20 double bond are possible. Although not pictured, formula I and the compounds of the present invention include alternative geometries of the C20 double bond.

In one embodiment, $R^2$ is hydrogen or a formyl group.

$R^3$ is selected from the group consisting of hydrogen, hydroxy, alkoxy, alkanoyloxy, =O, acyloxy and carbonyl. In one embodiment, $R^3$ is an acyloxy group. Examples of an acyloxy group include, but are not limited to an acetoxy group.

In one embodiment, $R^8$ is a hydroxy group.

In one embodiment, the present invention provides a compound of formula I, wherein:

$R^1$ is selected from the group consisting of $NR^4R^5$, $SR^6$ and $OR^7$;

$R^2$ is selected from the group consisting of hydrogen and formyl;

$R^3$ is selected from the group consisting of hydrogen, hydroxy, and acyloxy;

$R^4$ and $R^5$ are independently selected from the group consisting of hydrogen, alkyl, alkenyl, heterocyclic, aryl, aralkyl, and PEG; and wherein $R^4$ and $R^5$ are optionally joined to form a ring;

$R^6$ is an alkyl group;

$R^7$ is hydrogen;

$R^8$ is a hydroxy group;

and salts, solvates, and hydrates thereof.

The chart below provides some exemplary compounds of the present invention and an assigned "compound number," which may be used herein throughout the specification. The present invention also includes salts, solvates and hydrates of the compounds.

| Compound number | Name of Compound |
|---|---|
| 1 | (1E,4S,4aR,5R,6aS,7S,9aR)-1-[(diethylamino)methylene]-7,11-dihydroxy-4-(methoxymethyl)-4a,6a-dimethyl-2,10-dioxo-1,2,4,4a,5,6,6a,7,8,9,9a,10-dodecahydroindeno[4,5-h]-isochromen-5-yl acetate |
| 2 | (1E,4S,4aR,5R,6aS,7S,9aR)-7,11-dihydroxy-4-(methoxymethyl)-4a,6a-dimethyl-2,10-dioxo-1-(Pyrrolidin-1-ylmethylene)-1,2,4,4a,5,6,6a,7,8,9,9a,10-dodecahydroindeno[4,5-h]isochromen-5-yl acetate |
| 3 | (1E,4S,4aR,5R,6aS,7S,9aR)-1-(anilinomethylene)-7,11-dihydroxy-4-(methoxymethyl)-4a,6a-dimethyl-2,10-dioxo-1,2,4,4a,5,6,6a,7,8,9,9a,10-dodecahydroindeno[4,5-h] isochromen-5-yl acetate |
| 4 | (1E,4S,4aR,5R,6aS,7S)-1-{[tert-butyl(2-hydroxyethyl)amino]methylene}-7,11-dihydroxy-4-(methoxymethyl)-4a,6a-dimethyl-2,10-dioxo-1,2,4,4a,5,6,6a,7,8,9,9a,10-dodecahydroindeno[4,5-h]isochromen-5-yl acetate |
| 5 | (1E,4S,4aR,5R,6aS,7S)-1-{[[3-(dimethylamino)propyl](methyl)amino]methylene}-7,11-dihydroxy-4-(methoxymethyl)-4a,6a-dimethyl-2,10-dioxo-1,2,4,4a,5,6,6a,7,8,9,9a,10-dodecahydroindeno[4,5-h]isochromen-5-yl acetate |
| 6 | (1E,4S,4aR,5R,6aS,7S)-7,11-dihydroxy-4-(methoxymethyl)-4a,6a-dimethyl-1-{[methyl(1-methylpyrrolidin-3-yl)amino]methylene}-2,10-dioxo-1,2,4,4a,5,6,6a,7,8,9,9a,10-dodecahydroindeno[4,5-h]isochromen-5-yl acetate |
| 7 | (1E,4S,4aR,5R,6aS,7S)-1-[(4-cyclohexylpiperazin-1-yl)methylene]-7,11-dihydroxy-4-(methoxymethyl)-4a,6a-dimethyl-2,10-dioxo-1,2,4,4a,5,6,6a,7,8,9,9a,10-dodecahydroindeno[4,5-h]isochromen-5-yl acetate |
| 8 | (1E,4S,4aR,5R,6aS,7S)-1-{[butyl (methyl)amino]methylene}-7,11-dihydroxy-4-(methoxymethyl)-4a,6a-dimethyl-2,10-dioxo-1,2,4,4a,5,6,6a,7,8,9,9a,10-dodecahydroindeno[4,5-h]isochromen-5-yl acetate |
| 9 | (1E,4S,4aR,5R,6aS,7S)-1-{[cyclohexyl (methyl)amino]methylene}-7,11-dihydroxy-4-(methoxymethyl)-4a,6a-dimethyl-2,10-dioxo-1,2,4,4a,5,6,6a,7,8,9,9a,10-dodecahydroindeno[4,5-h]isochromen-5-yl acetate |
| 10 | (1E,4S,4aR,5R,6aS,7S)-1-[(4-benzylpiperazin-1-yl)methylene]-7,11-dihydroxy-4-(methoxymethyl)-4a,6a-dimethyl-2,10-dioxo-1,2,4,4a,5,6,6a,7,8,9,9a,10-dodecahydroindeno[4,5-h]isochromen-5-yl acetate |
| 11 | (1E,4S,4aR,5R,6aS,7S)-7,11-dihydroxy-4-(methoxymethyl)-4a,6a-dimethyl-2,10-dioxo-1-(piperidin-1-ylmethylene)-1,2,4,4a,5,6,6a,7,8,9,9a,10-dodecahydroindeno[4,5-h] isochromen-5-yl acetate |
| 12 | (1E,4S,4aR,5R,6aS,7S)-1-(3,4-dihydroisoquinolin-2(1H)-ylmethylene)-7,11-dihydroxy-4-(methoxymethyl)-4a,6a-dimethyl-2,10-dioxo-1,2,4,4a,5,6,6a,7,8,9,9a,10-dodecahydroindeno[4,5-h] isochromen-5-yl acetate |
| 13 | (1E,4S,4aR,5R,6aS,7S)-7,11-dihydroxy-4-(methoxymethyl)-4a,6a-dimethyl-2,10-dioxo-1-[(4-phenylpiperazin-1-yl)methylene]-1,2,4,4a,5,6,6a,7,8,9,9a,10-dodecahydroindeno [4,5-h] isochromen-5-yl acetate |
| 14 | (1E,4S,4aR,5R,6aS,7S)-7,11-dihydroxy-4-(methoxymethyl)-4a,6a-dimethyl-1-[(4-methylpiperazin-1-yl)methylene]-2,10-dioxo-1,2,4,4a,5,6,6a,7,8,9,9a,10-dodecahydroindeno [4,5-h] isochromen-5-yl acetate |
| 15 | (1E,4S,4aR,5R,6aS,7S)-7,11-dihydroxy-4-(methoxymethyl)-4a,6a-dimethyl-2,10-dioxo-1-[(4-phenylpiperidin-1-yl)methylene]-1,2,4,4a,5,6,6a,7,8,9,9a,10-dodecahydroindeno [4,5-h] isochromen-5-yl acetate |
| 16 | (1E,4S,4aR,5R,6aS,7S)-7-(formyloxy)-11-hydroxy-4-(methoxymethyl)-4a,6a-dimethyl-2,10-dioxo-1-(pyrrolidin-1-ylmethylene)-1,2,4,4a,5,6,6a,7,8,9,9a,10-dodecahydroindeno[4,5-h]isochromen-5-yl acetate |
| 17 | (1E,4S,4aR,5R,6aS,7S)-1-[(diallylamino)methylene]-7-(formyloxy)-11-hydroxy-4-(methoxymethyl)-4a,6a-dimethyl-2,10-dioxo-1,2,4,4a,5,6,6a,7,8,9,9a,10-dodecahydroindeno[4,5-h]isochromen-5-yl acetate |
| 18 | (1E,4S,4aR,5R,6aS,7S)-1-[(diethylamino)methylene]-7-(formyloxy)-11-hydroxy-4-(methoxymethyl)-4a,6a-dimethyl-2,10-dioxo-1,2,4,4a,5,6,6a,7,8,9,9a,10-dodecahydroindeno[4,5-h]isochromen-5-yl acetate |
| 19 | Acetic acid 4-{[bis-(2-hydroxy-ethyl)-amino]-methylene}-6,17-dihydroxy-1-methoxymethyl-10,13-dimethyl-3,7-dioxo-1,3,4,7,10,11,12,13,14,15,16,17-dodecahydro-2-oxa-cyclopenta[a]phenanthren-11-yl ester |
| 20 | Acetic acid 4-[(tert-butyl-methyl-amino)-methylene]-6,17-dihydroxy-1-methoxymethyl-10,13-dimethyl-3,7-dioxo-1,3,4,7,10,11,12,13,14,15,16,17-dodecahydro-2-oxa-cyclopenta[a]phenanthren-11-yl ester |
| 21 | Acetic acid 4-{[bis-(3-dimethylamino-propyl)-amino]-methylene}-6,17-dihydroxy-1-methoxymethyl-10,13-dimethyl-3,7-dioxo-1,3,4,7,10,11,12,13,14,15,16,17-dodecahydro-2-oxa-cyclopenta[a]phenanthren-11-yl ester |
| 22 | 1-(11-Acetoxy-6,17-dihydroxy-1-methoxymethyl-10,13-dimethyl-3,7-dioxo-1,7,10,11,12,13,14,15,16,17-decahydro-2-oxa-cyclopenta[a]phenanthren-4-ylidenemethyl)-piperidine-4-carboxylic acid methyl ester |
| 23 | 1-(11-Acetoxy-6,17-dihydroxy-1-methoxymethyl-10,13-dimethyl-3,7-dioxo-1,7,10,11,12,13,14,15,16,17-decahydro-2-oxa-cyclopenta[a]phenanthren-4-ylidenemethyl)-piperidine-4-carboxylic acid |
| 24 | 4-[(11-Acetoxy-6,17-dihydroxy-1-methoxymethyl-10,13-dimethyl-3,7-dioxo-1,7,10,11,12,13,14,15,16,17-decahydro-2-oxa-cyclopenta[a]phenanthren-4-ylidenemethyl)-methyl-amino]-2,5-dimethyl-hex-2-enoic acid methyl ester |
| 25 | Acetic acid 6,17-dihydroxy-1-methoxymethyl-4-[({3-[4-(4-methoxy-phenyl)-piperazin-1-yl]-propyl}-methyl-amino)-methylene]-10,13-dimethyl-3,7-dioxo-1,3,4,7,10,11,12,13,14,15,16,17-dodecahydro-2-oxa-cyclopenta[a]phenanthren-11-yl ester |
| 26 | Acetic acid 6,17-dihydroxy-1-methoxymethyl-10,13-dimethyl-4-({methyl-[3-(4-methyl-piperazin-1-yl)-propyl]-amino}-methylene)-3,7-dioxo-1,3,4,7,10,11,12,13,14,15,16,17-dodecahydro-2-oxa-cyclopenta[a]phenanthren-11-yl ester |
| 27 | Acetic acid 6,17-dihydroxy-1-methoxymethyl-10,13-dimethyl-4-{[methyl-(3-morpholin-4-yl-propyl)-amino]-methylene}-3,7-dioxo-1,3,4,7,10,11,12,13,14,15,16,17-dodecahydro-2-oxa-cyclopenta[a]phenanthren-11-yl ester |
| 28 | Acetic acid 4-{[(2-benzenesulfonyl-ethyl)-(3-diethylamino-propyl)-amino]-methylene}-6,17-dihydroxy-1-methoxymethyl-10,13-dimethyl-3,7-dioxo-1,3,4,7,10,11,12,13,14,15,16,17-dodecahydro-2-oxa-cyclopenta[a]phenanthren-11-yl ester |
| 29 | Acetic acid 4-{[(1-aza-bicyclo[3.3.1]non-5-ylmethyl)-benzyl-amino]-methylene}-6,17-dihydroxy-1-methoxymethyl-10,13-dimethyl-3,7-dioxo-1,3,4,7,10,11,12,13,14,15,16,17-dodecahydro-2-oxa-cyclopenta[a]phenanthren-11-yl ester |
| 30 | Acetic acid 6,17-dihydroxy-1-methoxymethyl-10,13-dimethyl-4-[4-(3-morpholin-4-yl-propyl)-piperazin-1-ylmethylene]-3,7-dioxo-1,3,4,7,10,11,12,13,14,15,16,17-dodecahydro-2-oxa-cyclopenta[a]phenanthren-11-yl ester |
| 31 | Acetic acid 4-{[(2-dimethylamino-ethyl)-methyl-amino]-methylene}-6,17-dihydroxy-1-methoxymethyl-10,13-dimethyl-3,7-dioxo-1,3,4,7,10,11,12,13,14,15,16,17-dodecahydro-2-oxa-cyclopenta[a]phenanthren-11-yl ester |

| Compound number | Name of Compound |
|---|---|
| 32 | Acetic acid 4-[4-(3-dimethylamino-propyl)-piperazin-1-ylmethylene]-6,17-dihydroxy-1-methoxymethyl-10,13-dimethyl-3,7-dioxo-1,3,4,7,10,11,12,13,14,15,16,17-dodecahydro-2-oxa-cyclopenta[a]phenanthren-11-yl ester |
| 33 | Acetic acid 6,17-dihydroxy-1-methoxymethyl-10,13-dimethyl-4-[4-(2-morpholin-4-yl-ethyl)-piperazin-1-ylmethylene]-3,7-dioxo-1,3,4,7,10,11,12,13,14,15,16,17-dodecahydro-2-oxa-cyclopenta[a]phenanthren-11-yl ester |
| 34 | Acetic acid 6,17-dihydroxy-1-methoxymethyl-10,13-dimethyl-4-[4-(1-methyl-piperidin-4-yl)-piperazin-1-ylmethylene]-3,7-dioxo-1,3,4,7,10,11,12,13,14,15,16,17-dodecahydro-2-oxa-cyclopenta[a]phenanthren-11-yl ester |
| 35 | [(11-Acetoxy-6,17-dihydroxy-1-methoxymethyl-10,13-dimethyl-3,7-dioxo-1,7,10,11,12,13,14,15,16,17-decahydro-2-oxa-cyclopenta[a]phenanthren-4-ylidenemethyl)-methyl-amino]-acetic acid tert-butyl ester |
| 36 | Acetic acid 4-{[(2,3-dihydroxy-propyl)-methyl-amino]-methylene}-6,17-dihydroxy-1-methoxymethyl-10,13-dimethyl-3,7-dioxo-1,3,4,7,10,11,12,13,14,15,16,17-dodecahydro-2-oxa-cyclopenta[a]phenanthren-11-yl ester |
| 37 | 4-[(11-Acetoxy-6,17-dihydroxy-1-methoxymethyl-10,13-dimethyl-3,7-dioxo-1,7,10,11,12,13,14,15,16,17-decahydro-2-oxa-cyclopenta[a]phenanthren-4-ylidenemethyl)-methyl-amino]-butyric acid |
| 38 | 1-(11-Acetoxy-6,17-dihydroxy-1-methoxymethyl-10,13-dimethyl-3,7-dioxo-1,7,10,11,12,13,14,15,16,17-decahydro-2-oxa-cyclopenta[a]phenanthren-4-ylidenemethyl)-azetidine-2-carboxylic acid |
| 39 | 1-(11-Acetoxy-6,17-dihydroxy-1-methoxymethyl-10,13-dimethyl-3,7-dioxo-1,7,10,11,12,13,14,15,16,17-decahydro-2-oxa-cyclopenta[a]phenanthren-4-ylidenemethyl)-pyrrolidine-2-carboxylic acid methyl ester |
| 40 | 1-(11-Acetoxy-6,17-dihydroxy-1-methoxymethyl-10,13-dimethyl-3,7-dioxo-1,7,10,11,12,13,14,15,16,17-decahydro-2-oxa-cyclopenta[a]phenanthren-4-ylidenemethyl)-pyrrolidine-2-carboxylic acid methyl ester |
| 41 | Acetic acid 4-{[benzyl-(2-cyano-ethyl)-amino]-methylene}-6,17-dihydroxy-1-methoxymethyl-10,13-dimethyl-3,7-dioxo-1,3,4,7,10,11,12,13,14,15,16,17-dodecahydro-2-oxa-cyclopenta[a]phenanthren-11-yl ester |
| 42 | Acetic acid 4-{[(2-diethylamino-ethyl)-ethyl-amino]-methylene}-6,17-dihydroxy-1-methoxymethyl-10,13-dimethyl-3,7-dioxo-1,3,4,7,10,11,12,13,14,15,16,17-dodecahydro-2-oxa-cyclopenta[a]phenanthren-11-yl ester |
| 43 | Acetic acid 4-{[benzyl-(2-dimethylamino-ethyl)-amino]-methylene}-6,17-dihydroxy-1-methoxymethyl-10,13-dimethyl-3,7-dioxo-1,3,4,7,10,11,12,13,14,15,16,17-dodecahydro-2-oxa-cyclopenta[a]phenanthren-11-yl ester |
| 44 | Acetic acid 6,17-dihydroxy-1-methoxymethyl-10,13-dimethyl-3,7-dioxo-4-(4-oxo-piperidin-1-ylmethylene)-1,3,4,7,10,11,12,13,14,15,16,17-dodecahydro-2-oxa-cyclopenta[a]phenanthren-11-yl ester |
| 45 | 4-{[(2-Dimethylamino-ethyl)-ethyl-amino]-methylene}-6,17-dihydroxy-1-methoxymethyl-10,13-dimethyl-10,11,12,13,14,15,16,17-octahydro-1H,4H-2-oxa-cyclopenta[a]phenanthrene-3,7-dione |
| 46 | Acetic acid 4-{[(2-dimethylamino-ethyl)-ethyl-amino]-methylene}-6,17-dihydroxy-1-methoxymethyl-10,13-dimethyl-3,7-dioxo-1,3,4,7,10,11,12,13,14,15,16,17-dodecahydro-2-oxa-cyclopenta[a]phenanthren-11-yl ester |
| 47 | Acetic acid 4-[1,4']bipiperidinyl-1'-ylmethylene-6,17-dihydroxy-1-methoxymethyl-10,13-dimethyl-3,7-dioxo-1,3,4,7,10,11,12,13,14,15,16,17-dodecahydro-2-oxa-cyclopenta[a]phenanthren-11-yl ester |
| 48 | Acetic acid 6,17-dihydroxy-1-methoxymethyl-10,13-dimethyl-4-morpholin-4-ylmethylene-3,7-dioxo-1,3,4,7,10,11,12,13,14,15,16,17-dodecahydro-2-oxa-cyclopenta[a]phenanthren-11-yl ester |
| 49 | Propionic acid 4-{[(2-dimethylamino-ethyl)-methyl-amino]-methylene}-6,17-dihydroxy-1-methoxymethyl-10,13-dimethyl-3,7-dioxo-1,3,4,7,10,11,12,13,14,15,16,17-dodecahydro-2-oxa-cyclopenta[a]phenanthren-11-yl ester |
| 50 | (1E,4S,4aR,5R,6aS,7S,9aR)-1-[(diethylamino)methylene]-5,7,11-trihydroxy-4-(methoxymethyl)-4a,6a-dimethyl-4a,5,6,6a,7,8,9,9a-octahydroindeno[4,5-h]-isochromene-2,10(1H,4H)-dione |
| 51 | (1Z,4S,4aR,5R,6aS,7S)-7,11-dihydroxy-4-(methoxymethyl)-4a,6a-dimethyl-2,10-dioxo-1-{12-oxo-16-[(3aR,4R,6aS)-2-oxohexahydro-1H-thieno[3,4-d]imidazol-4-yl]-5,8-dioxa-2,11-diazahexadec-1-ylidene}-1,2,4,4a,5,6,6a,7,8,9,9a,10-dodecahydroindeno[4,5-h]isochromen-5-yl acetate |
| 52 | Acetic acid 4-butylsulfanylmethylene-6,17-dihydroxy-1-methoxymethyl-10,13-dimethyl-3,7-dioxo-1,3,4,7,10,11,12,13,14,15,16,17-dodecahydro-2-oxa-cyclopenta[a]phenanthren-11-yl ester |
| 53 | 17-Pegylated di-(1E,4S,4aR,5R,6aS,7S)-1-{[[3-(dimethylamino)propyl](methyl)amino]methylene}-7,11-dihydroxy-4-(methoxymethyl)-4a,6a-dimethyl-2,10-dioxo-1,2,4,4a,5,6,6a,7,8,9,9a,10-dodeca-hydroindeno[4,5-h]isochromen-5-yl acetate |
| 54 | 17-Pegylated (1E,4S,4aR,5R,6aS,7S,9aR)-1-[(diethylamino)-methylene]-7,11-dihydroxy-4-(methoxymethyl)-4a,6a-dimethyl-2,10-dioxo-1,2,4,4a,5,6,6a,7,8,9,9a,10-dodecahydroindeno[4,5-h]isochromen-5-yl acetate |
| 55 | a PEGylated 17-hydroxywortmannin compound |
| 56 | (1Z,4S,4aR,5R,6aS,7S)-1-{[t-butylamino]methylene}-7,11-dihydroxy-4-(methoxymethyl)-4a,6a-dimethyl-2,10-dioxo-1,2,4,4a,5,6,6a,7,8,9,9a,10-dodecahydroindeno[4,5-h]-isochromen-5-yl acetate |
| 57 | (1Z,4S,4aR,5R,6aS,7S)-1-{[3-dimethylamino-propylamino]-methylene}-7,11-dihydroxy-4-(methoxymethyl)-4a,6a-dimethyl-2,10-dioxo-1,2,4,4a,5,6,6a,7,8,9,9a,10-dodecahydroindeno[4,5-h]isochromen-5-yl acetate |
| 58 | (1Z,4S,4aR,5R,6aS,7S)-7,11-dihydroxy-1-{[(2-mercaptoethyl)amino]methylene}-4-(methoxymethyl)-4a,6a-dimethyl-2,10-dioxo-1,2,4,4a,5,6,6a,7,8,9,9a,10-dodecahydroindeno[4,5-h]isochromen-5-yl acetate |
| 59 | (1Z,4S,4aR,5R,6aS,7S,9aR)-1-[(ethylamino)methylene]-7,11-dihydroxy-4-(methoxymethyl)-4a,6a-dimethyl-2,10-dioxo-1,2,4,4a,5,6,6a,7,8,9,9a,10-dodecahydroindeno[4,5-h]-isochromen-5-yl acetate |
| 60 | (1E,4S,4aR,5R,6aS,7S)-1-{[[3-(dimethylamino)propyl](methyl)amino]methylene}-5,7,11-trihydroxy-4-(methoxymethyl)-4a,6a-dimethyl-4a,5,6,6a,7,8,9,9a-octahydroindeno[4,5-h]-isochromene-2,10(1H,4H)-dione |
| 61 | (1Z,4S,4aR,5R,6aS,7S,9aR)-7,11-dihydroxy-1-(hydroxy-methylene)-4-(methoxymethyl)-4a,6a-dimethyl-2,10-dioxo-1,2,4,4a,5,6,6a,7,8,9,9a,10-dodecahydroindeno[4,5-h]-isochromen-5-yl acetate |
| 62 | (1E,4S,4αR,5R,6αS,7S,9αR)-1-({tert-butyl[2-(dimethylamino)ethyl]amino}methylene)-7,11-dihydroxy-4-(methoxymethyl)-4α,6α-dimethyl-2,10-dioxo-1,2,4,4α,5,6,6α,7,8,9,9α,10-dodecahydroindeno[4,5-h]-isochrom en-5-yl acetate |
| 63 | Butanoic acid 4-{[(2-dimethylamino-propyl)-methyl-amino]-methylene}-6,17-dihydroxy-1-methoxymethyl-10,13-dimethyl-3,7-dioxo-1,3,4,7,10,11,12,13,14,15,16,17-dodecahydro-2-oxa-cyclopenta[a]phenanthren-11-yl ester |
| 64 | Acetic acid 4-{[(2-dimethylamino-propyl)-ethyl-amino]-methylene}-6,17-dihydroxy-1-methoxymethyl-10,13-dimethyl-3,7-dioxo-1,3,4,7,10,11,12,13,14,15,16,17-dodecahydro-2-oxa-cyclopenta[a]phenanthren-11-yl ester |
| 65 | (1E,4S,4aR,5R,6aS,7S,9aR)-1-({4-[2-(2,5-dioxo-2,5-dihydro-1H-pyrrol-1-yl)ethyl]piperazin-1-yl}methylene)-7,11-dihydroxy-4-(methoxymethyl)-4a,6a-dimethyl-2,10-dioxo-1,2,4,4a,5,6,6a,7,8,9,9a,10-dodecahydroindeno[4,5-h]-isochromen-5-yl acetate |

The present invention also encompasses PEGylated compounds of formula I wherein the R groups are described as above. Examples include, but are not limited to compounds PEGylated at position $R^1$, $R^2$, or $R^3$.

The presence of certain substituents in the compounds of formula I may enable salts of the compounds to be formed.

Suitable salts include pharmaceutically acceptable salts, for example acid addition salts derived from inorganic or organic acids, and salts derived from inorganic and organic bases.

Acid addition salts include hydrochlorides, hydrobromides, hydroiodides, alkylsulphonates, e.g. methanesulphonates, ethanesulphonates, or isethionates, arylsulphonates, e.g. p-toluenesulphonates, besylates or napsylates, phosphates, sulphates, hydrogen sulphates, acetates, trifluoroacetates, propionates, citrates, maleates, fumarates, malonates, succinates, lactates, oxalates, tartrates and benzoates.

Salts derived from inorganic or organic bases include alkali metal salts such as sodium or potassium salts, alkaline earth metal salts such as magnesium or calcium salts, and organic amine salts such as morpholine, piperidine, dimethylamine or diethylamine salts.

Particularly useful salts of compounds according to the invention include pharmaceutically acceptable salts, especially acid addition pharmaceutically acceptable salts.

Figure 2:
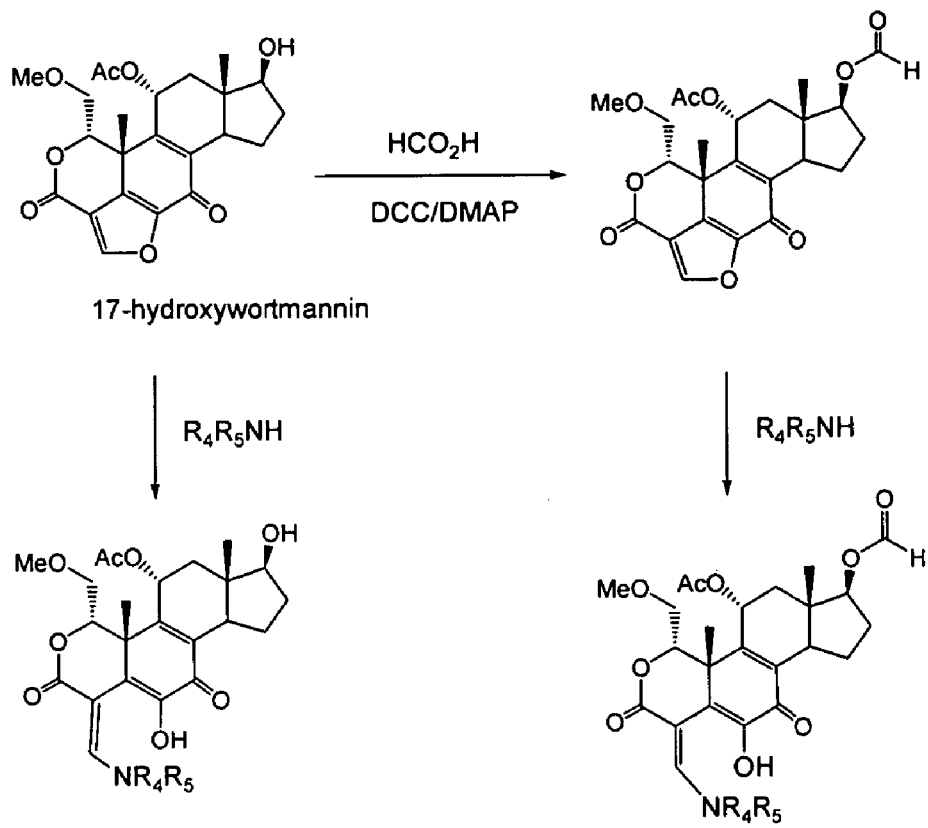
FIG. 2 depicts a general synthesis scheme for compounds of the present invention.

The compounds of the present invention can be made from 17-hydroxywortmannin, described above and as described in prior application U.S. Ser. No. 10/828,474 filed Apr. 20, 2004, herein incorporated by reference. 17-hydroxywortmannin can be treated with an amine to give a furan ring opened compound. 17-hydroxywortmannin can also be formylated at the 17-position and treated with an amine to give a furan ring opened compound. See FIG. 2.

Figure 3:
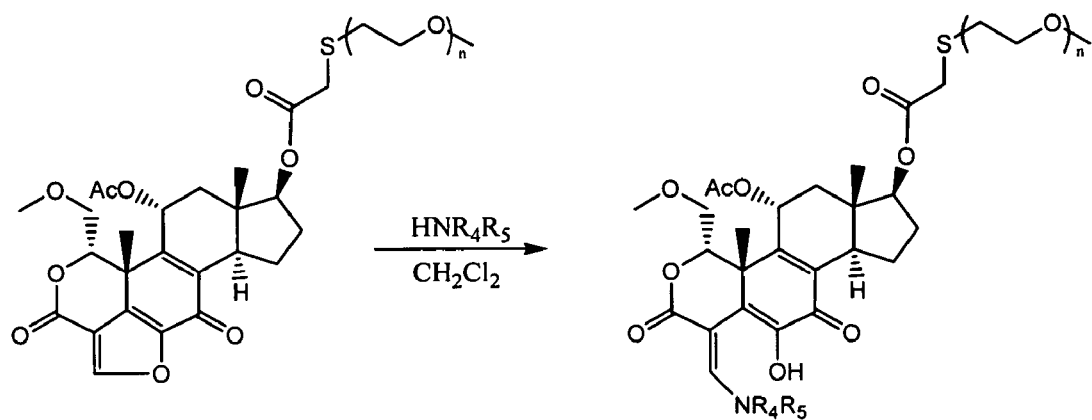
FIG. 3 depicts a synthesis scheme for PEGylated compounds of the present invention.
Figure 4:
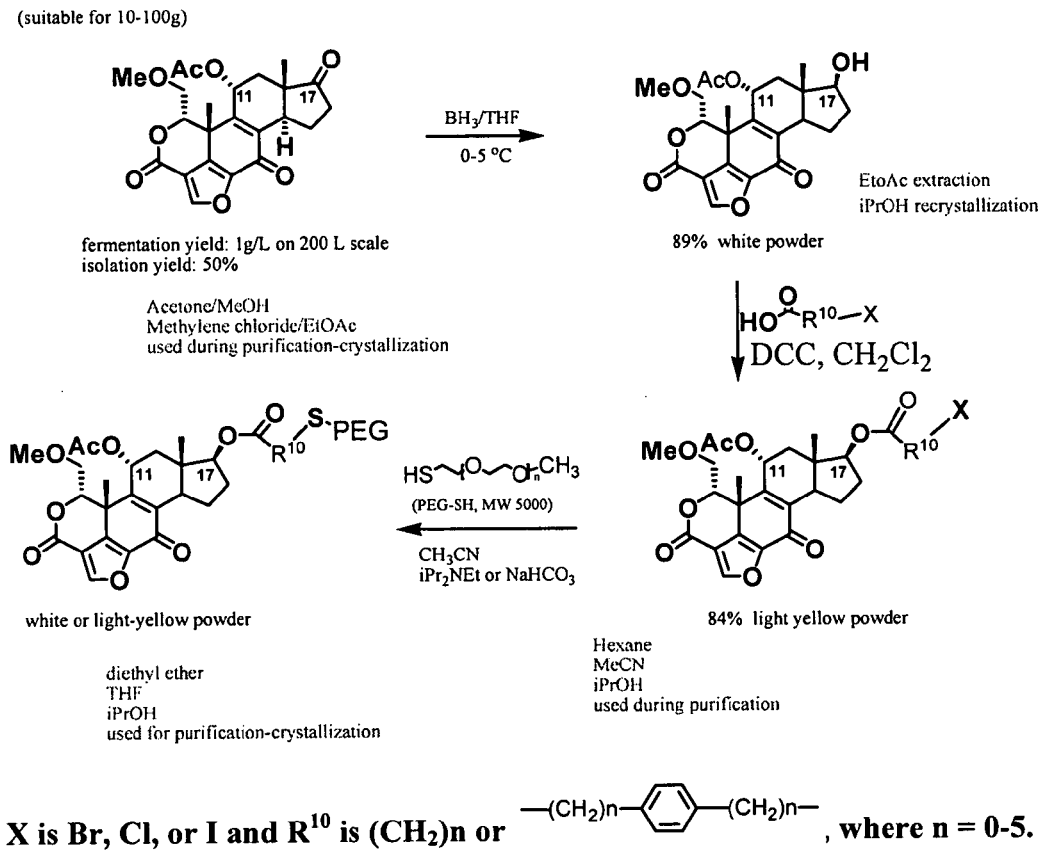
FIG. 4 depicts a synthesis scheme for PEGylated 17-hydroxywortmannin.
Figure 5:
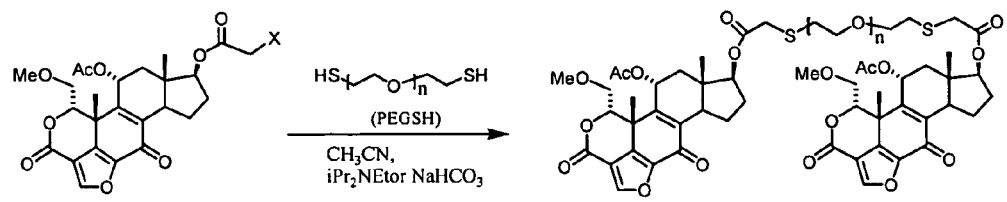
FIG. 5 depicts a synthesis scheme for a PEGylated 17-hydroxywortmannin derivative.
Figure 6:
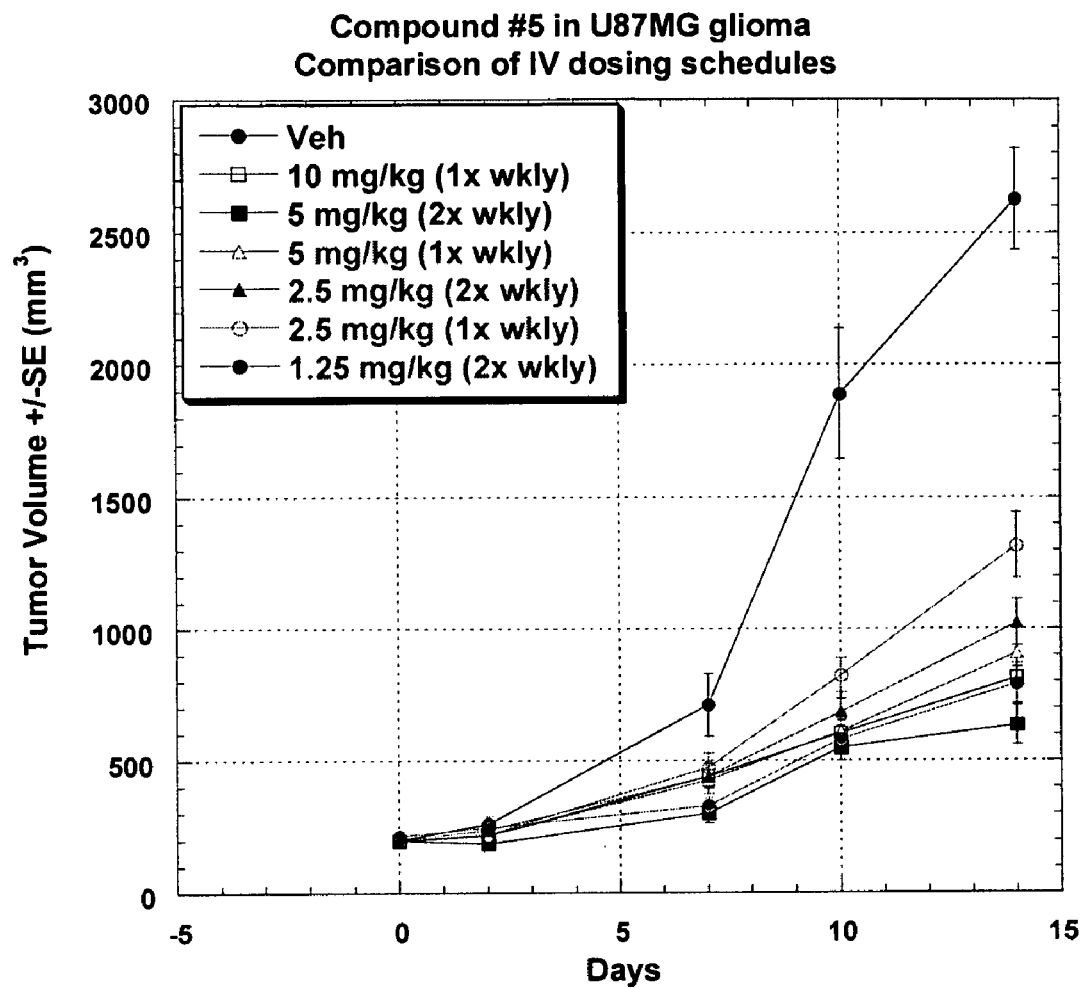
FIG. 6 shows a comparison of results obtained with different IV dosing schedules (1× and 2× weekly) and different concentrations of compound 5 in U87MG glioma.
Figure 7:
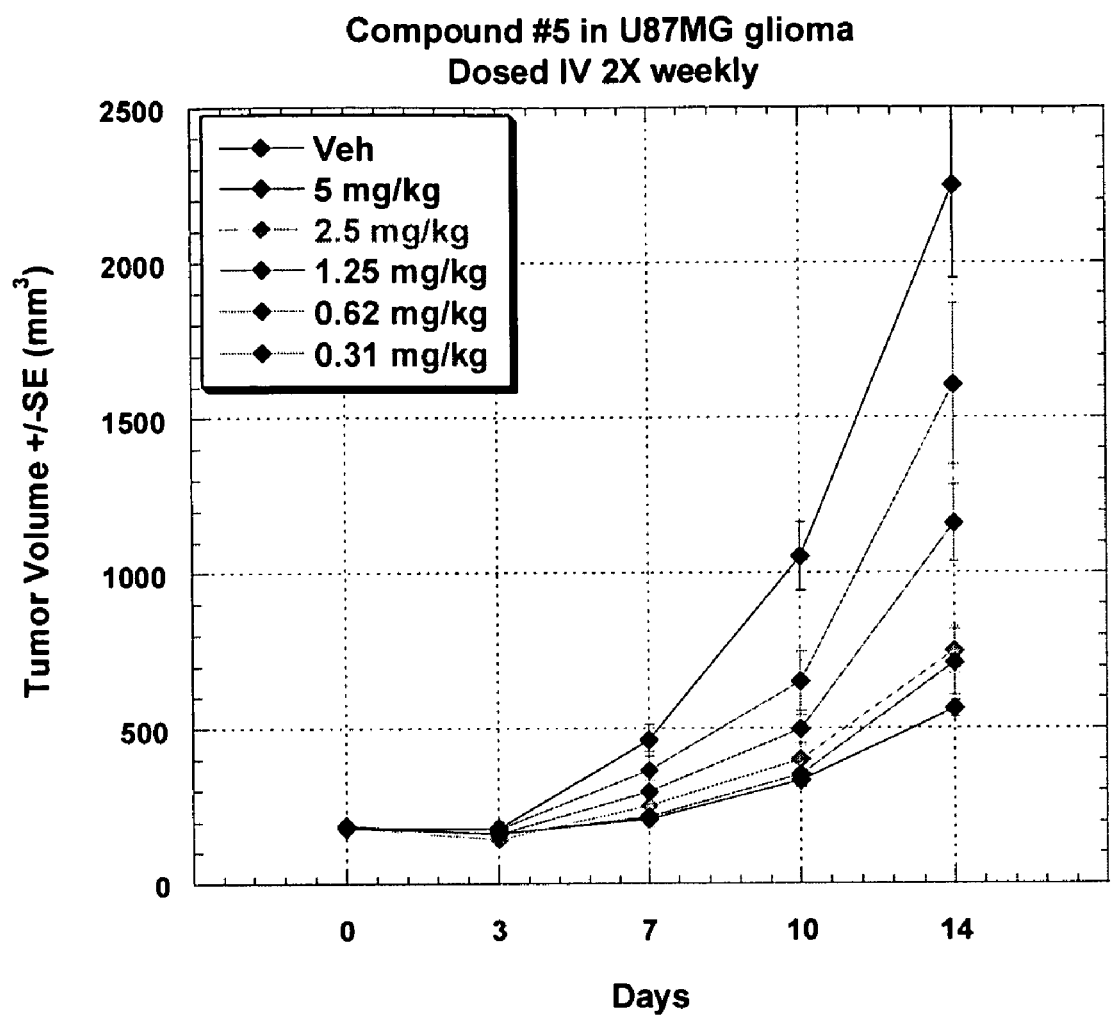
FIG. 7 shows a comparison of results obtained with different doses of compound 5 in U87MG glioma (dosed at 2× weekly IV).
Figure 8:
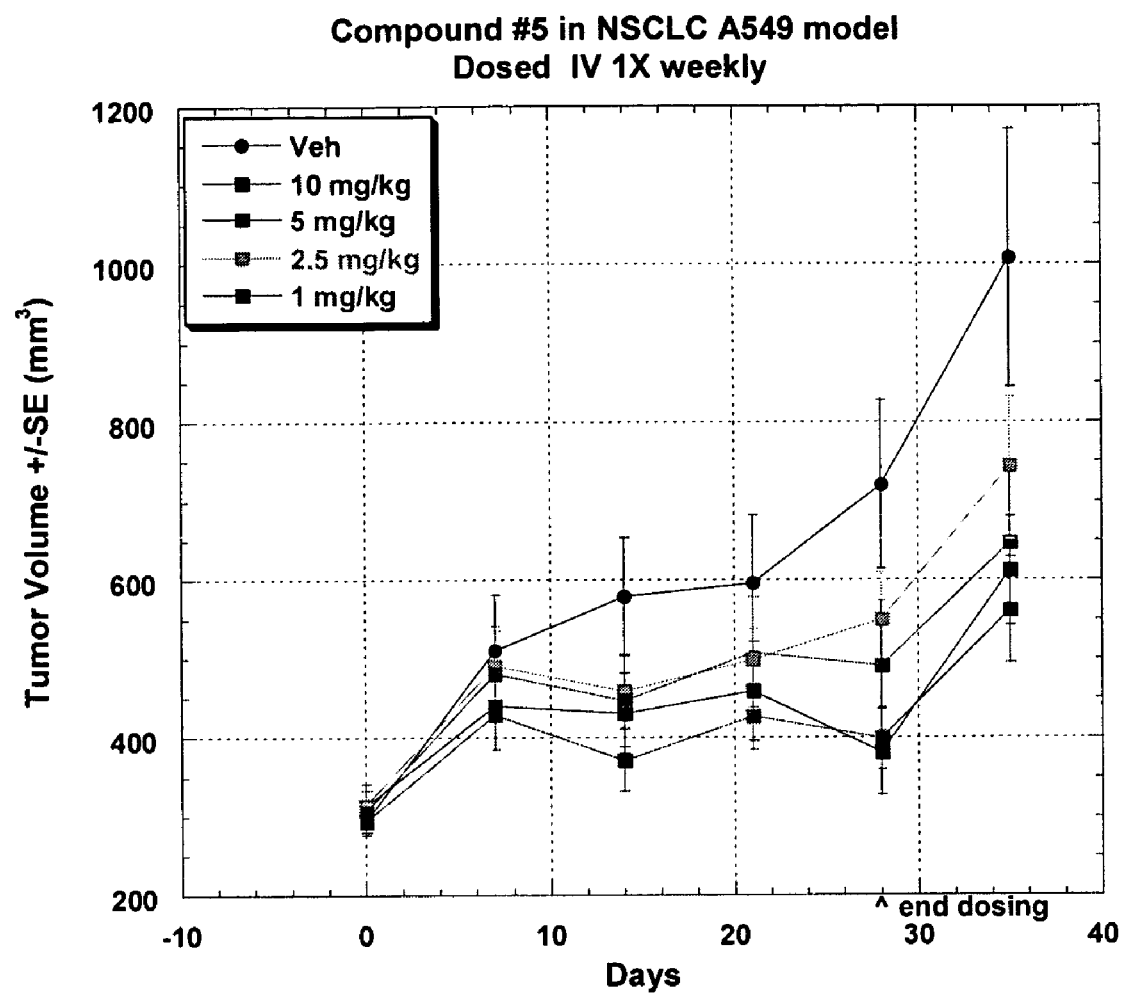
FIG. 8 shows a comparison of results obtained with different doses of compound 5 in a NSCLC A549 model (dosed at 1× weekly IV).
Figure 9:
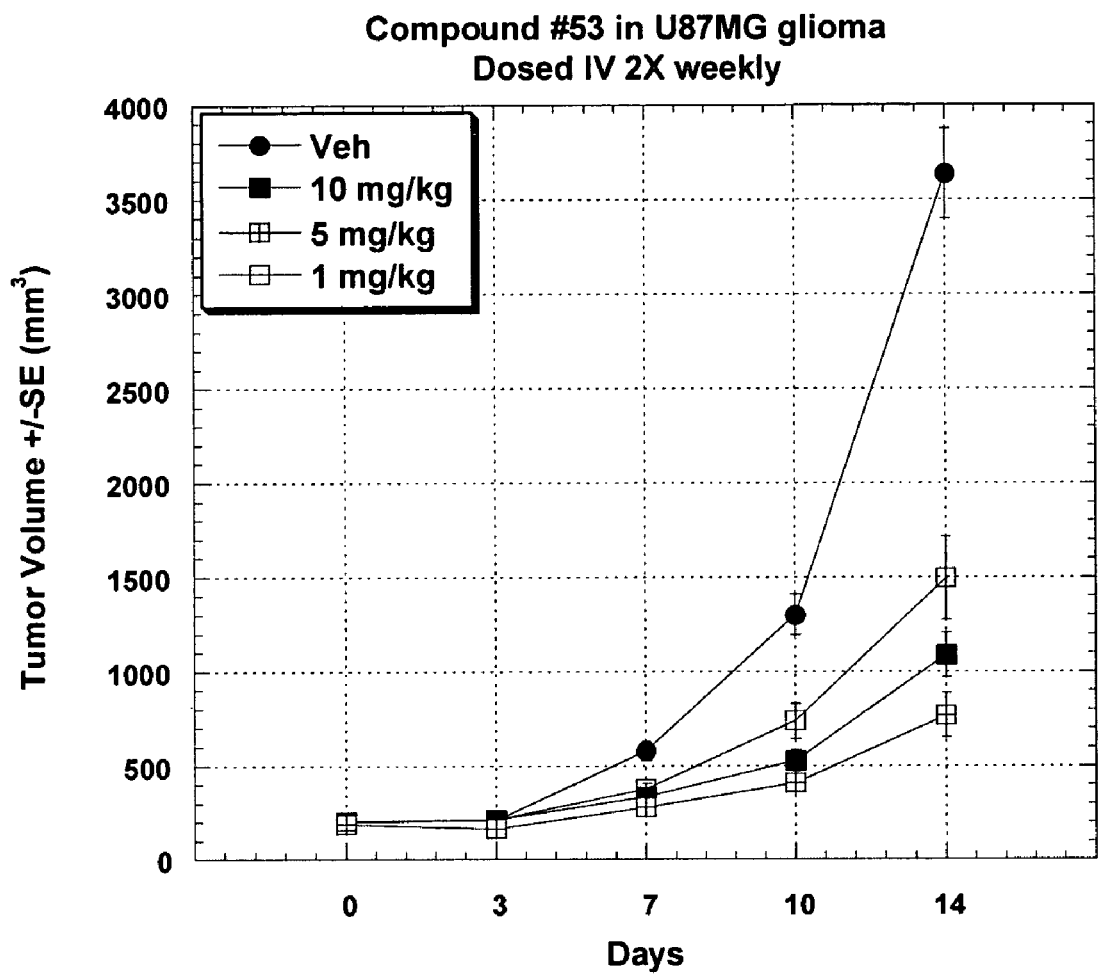
FIG. 9 shows a comparison of results obtained with different doses of compound 53 in U87MG glioma (dosed at 2× weekly IV).
Figure 10:
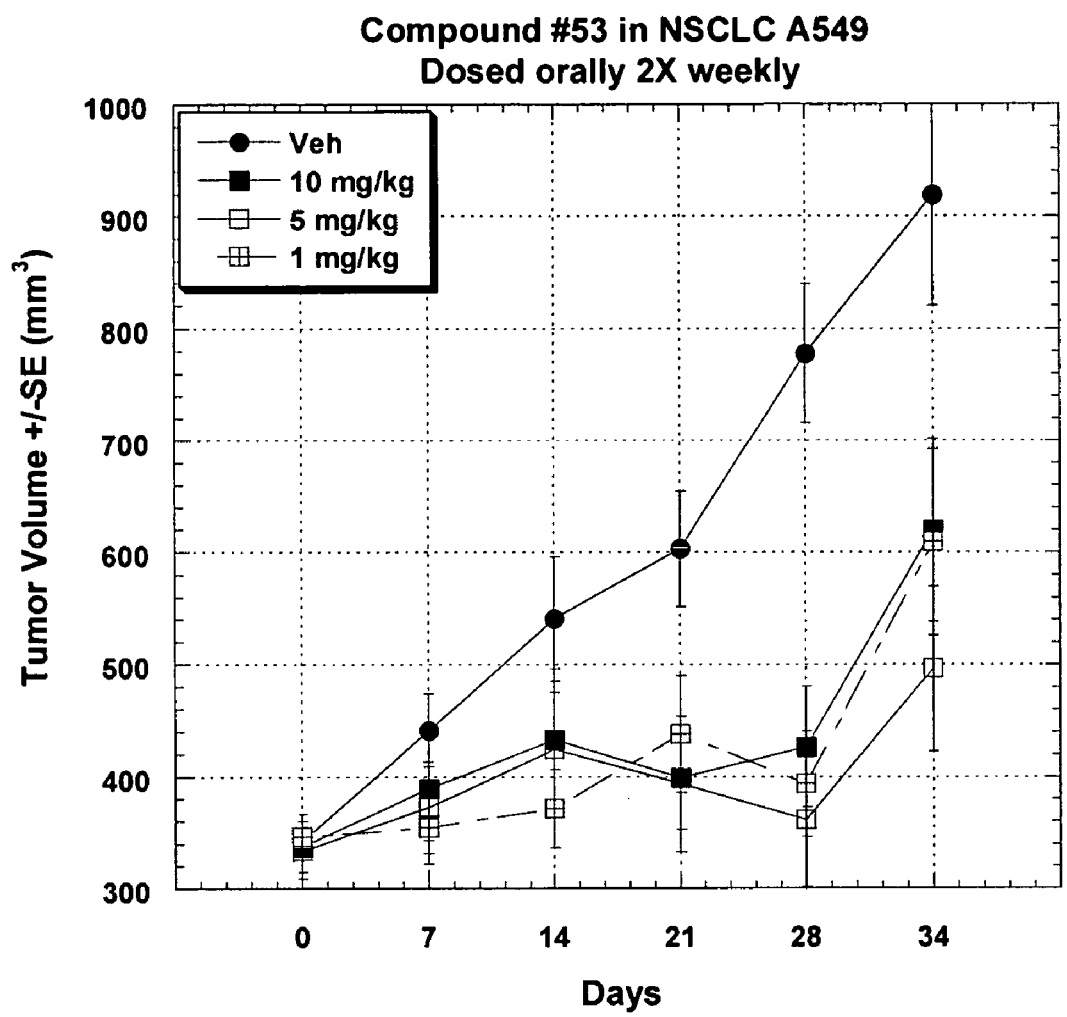
FIG. 10 shows a comparison of results obtained with different doses of compound 53 in NSCLC A549 (dosed orally 2× weekly).
Figure 11:
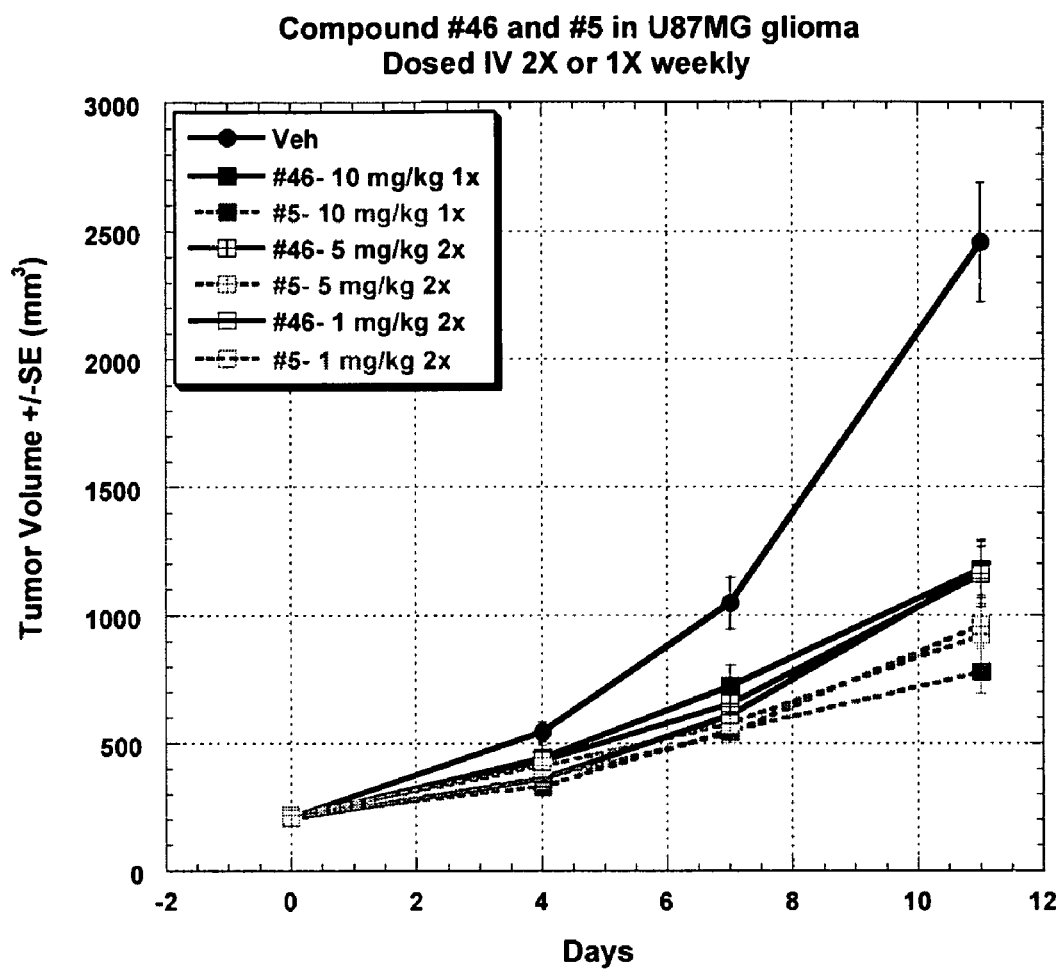
FIG. 11 shows a comparison of results obtained with different IV dosing schedules (1× and 2× weekly) and different doses of compound 46 and compound 5 in U87MG glioma.
Figure 12:
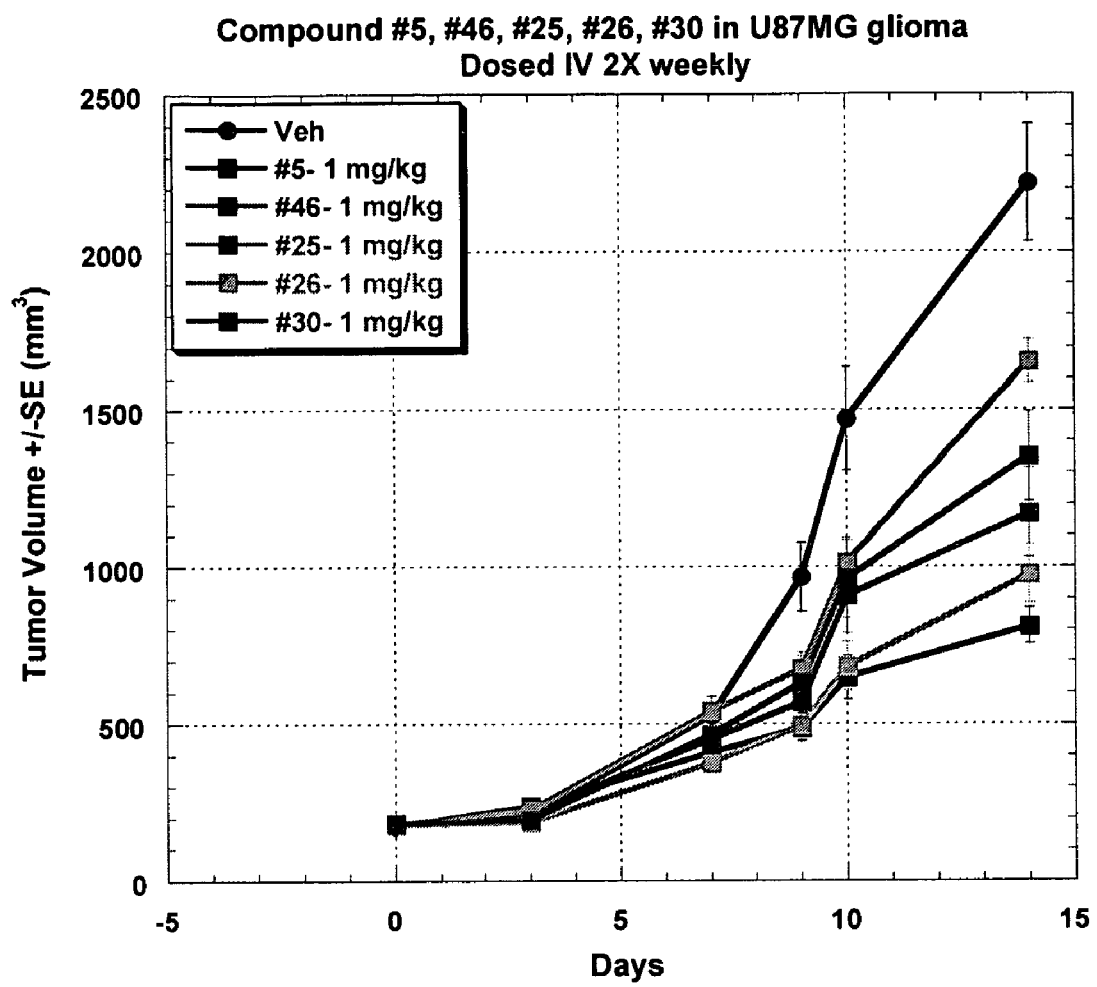
FIG. 12 shows in vivo activity and comparison of compounds 5, 46, 25 and 30 in U87MG glioma where the compounds were dosed 2× weekly, IV.
Figure 13:
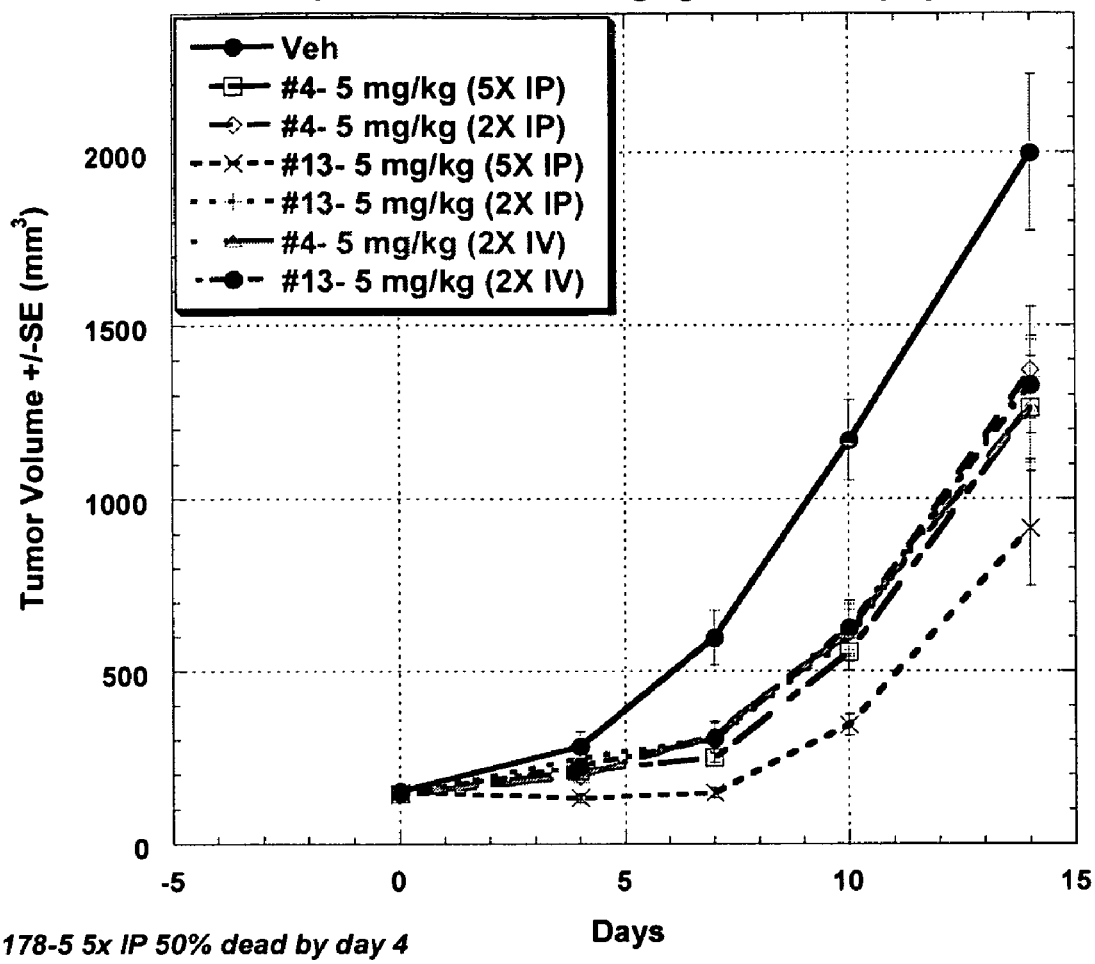
FIG. 13 shows in vivo activity of compounds 4 and 13 in U87MG glioma at 5 mg/kg IP 5× or 2× weekly, or IV 2× weekly.
Figure 14:
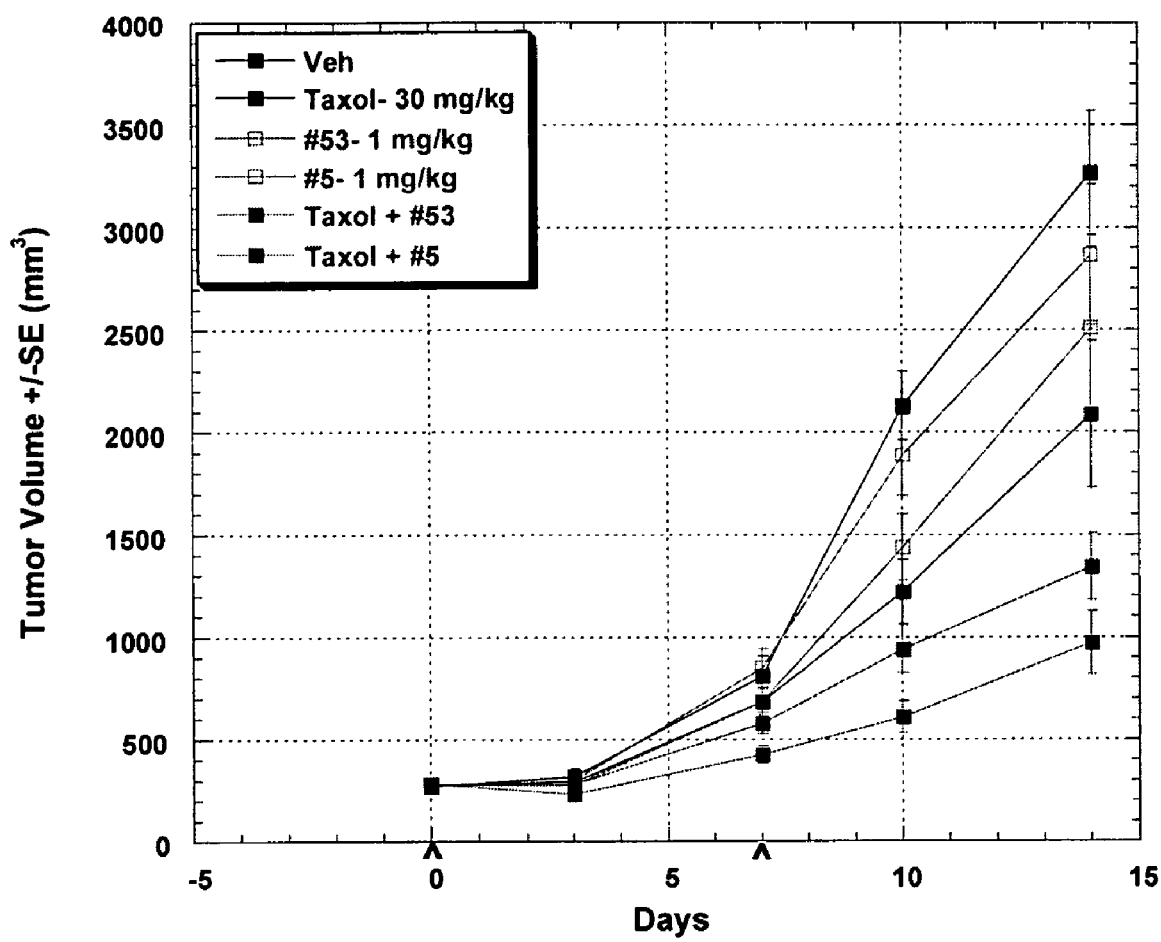
FIG. 14 shows the results of a combination therapy with compound 5 or 53 and Paclitaxel in U87MG glioma model (all dosed IV 1× weekly).
Figure 15:
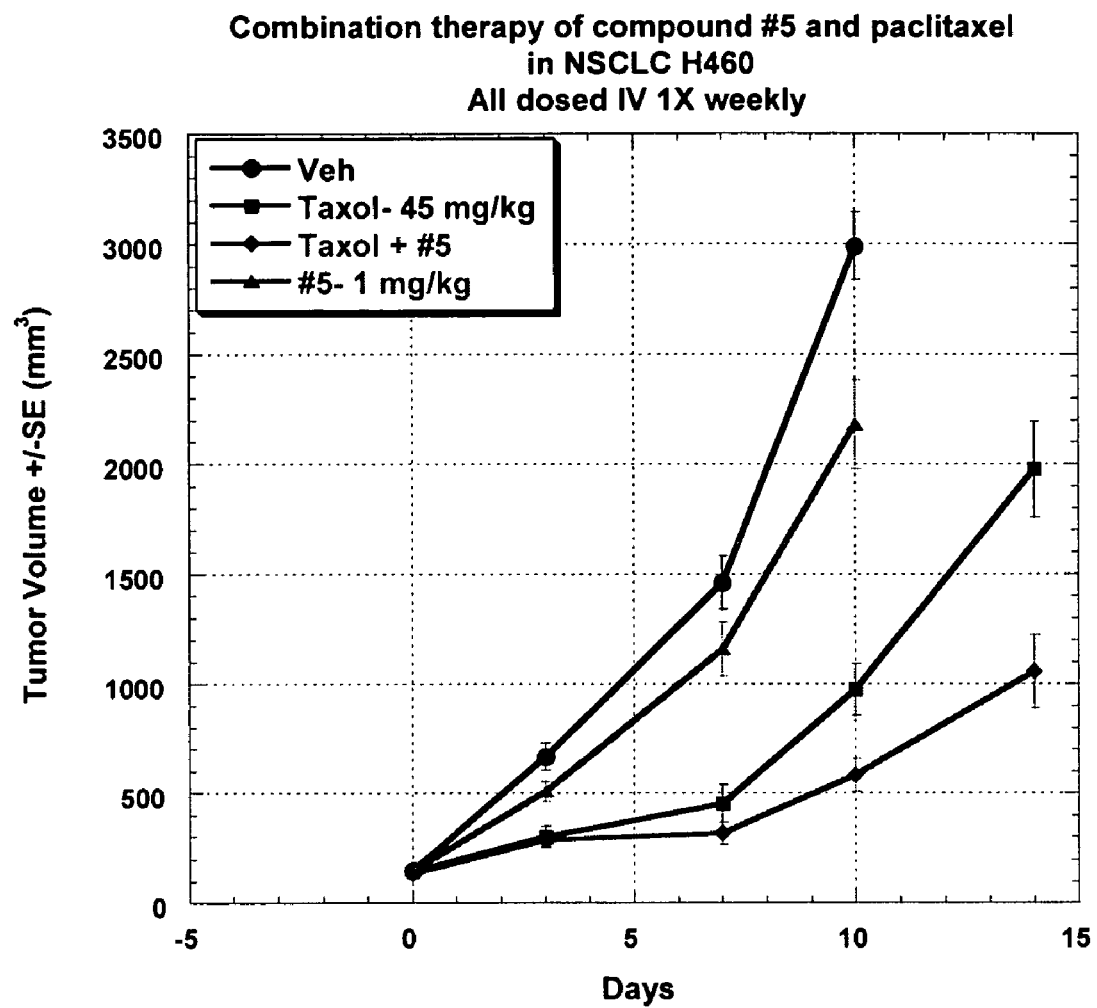
FIG. 15 shows the results of a combination therapy with compound 5 and Paclitaxel in NSCLC H460 model (dosed IV 1× weekly).
Figure 16A:
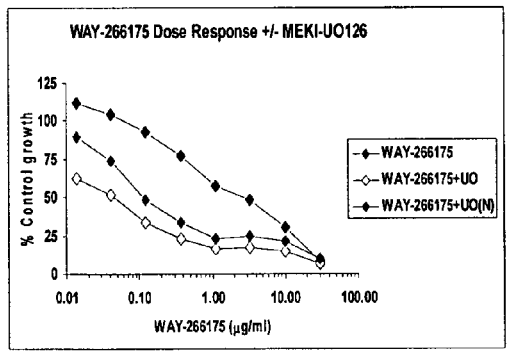
FIGS. 16A and B show that compound 4 in combination with MEK inhibitors synergistically inhibited growth of HCT116 colon tumor cells.
Figure 16B:
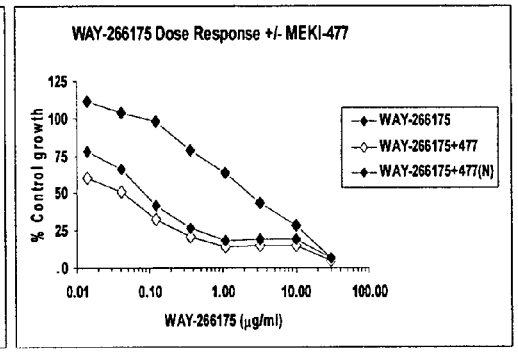
Figure 17A:
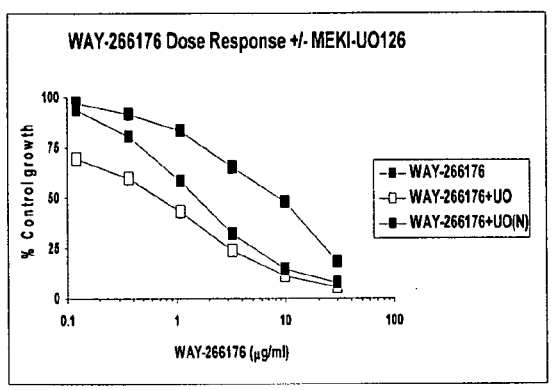
FIGS. 17A and B show that compound 5 in combination with MEK inhibitors synergistically inhibited growth of HCT116 colon tumor cells.
Figure 17B:
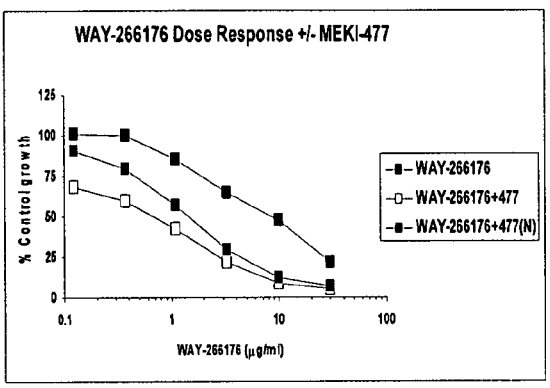

PEGylated compounds of the present invention can be made from a PEGylated 17-hydroxywortmannin compound in dichloromethane by adding an amine. See FIG. 3. Methods for preparing PEGylated 17-hydroxywortmannin and PEGylated wortmannin derivatives are depicted in FIGS. 4 and 5, respectively, and are described in prior application U.S. Ser. No. 10/828,474 filed Apr. 20, 2004.

For instance, as depicted in FIG. 4, a solution of 60 mg wortmannin (0.14 mmol from Aldrich) in 12 mL tetrahydrofuran (THF) is cooled in a 0° C. ice bath under nitrogen. 1M borane in THF solution (134 µL, 0.14 mmol from Aldrich) is added and the reaction mixture is stirred at 0° C. for 3.5 hours. The reaction is quenched with 1 mL water. After warming to room temperature, the reaction mixture is diluted with water and extracted with ethyl acetate. After work up, about 60 mg (90% pure 17-hydroxy-wortmannin by HPLC) solid is obtained. This solid (about 0.126 mmol 17-hydroxy-wortmannin) is dissolved in 15 mL methylene chloride, reacted with iodoacetic acid (24 mg, 0.13 mmol), dicyclohexylcarbodiimide (DCC) (27 mg, 0.13 mmol) and 4-N,N-dimethylaminopyridine (DMAP) (0.1 mg as catalyst). The reaction mixture is kept at room temperature for 1 hour. After work up, about 75 mg crude product (yellow solid) is obtained. Pure 17-dihydro-17-(1-iodoacetyl)-wortmannin is isolated by preparative HPLC. A total of 54 mg of white solid is obtained.

Also, as depicted in FIG. 4, 40 mg (0.067 mmol) 17-dihydro-17-(1-iodoacetyl)-wortmannin is dissolved in 15 mL acetonitrile and 10 mL 0.1 M sodium bicarbonate under nitrogen. A total of 345 mg M-PEG-SH-5000 (0.069 mmol) is added within 1 hour (4 batches). After stirring another hour at room temperature, the reaction mixture is extracted with methylene chloride and worked-up. About 320 mg crude product is obtained. A total of 209 mg pure water-soluble drug-polymer PEGylated wortmannin derivative is obtained from 260 mg of crude product after prep-HPLC.

In another embodiment, the present invention provides a method of inhibiting PI3K activity by providing one or more compounds of the present invention in a cell (in vivo or in vitro). Compounds of the present invention can be tested to determine the minimum concentration sufficient to inhibit PI3K, i.e., the minimum inhibitory concentration, $IC_{50}$. See Example 66. Tables 1 and 2 below show $IC_{50}$ results for exemplary compounds of the present invention. Unless otherwise indicated, $IC_{50}$ is measured in µg/ml. One skilled in the art would appreciate assays that would demonstrate the ability of compounds of the present invention to inhibit PI3K activity. For example, U.S. Pat. No. 5,378,725 provides an exemplary test system one may use to test the activity of the compounds. One skilled in the art would appreciate other assay systems. Further, one skilled in the art would appreciate mammal models to use in studying inhibition of PI3K activity. Such models include, but are not limited to human xenograft models in athymic mice. Similarly, one skilled in the art can use these models to determine the activity and toxicity of the compounds of the present invention.

In one in vivo protocol, Balb/c nu/nu (athymic) mice are housed in accordance with Association for Accreditation of Laboratory Animal Care (AALAACC) standards for at least one week prior to their experimental usage. The animals are housed in microisolator cages and handled only in a laminar flow hood. All food and water is autoclaved. Mice are inoculated on the left flank with a volume of 200 µL using a 25-26 gauge sterile needle and syringe with a suspension of cells. The cells are resuspended in full growth media and delivered at 10 million cells per mouse. When the resulting tumors reach the appropriate size for staging, the mice are regrouped to produce equivalent sized groups with n=10. Once staged, the mice are dosed 0.2 cc iv with the compounds. The compounds can be resuspended Phosphate Buffered Saline (PBS) right before injecting into the mouse. Treatment is typically 1× weekly or 2× weekly for the duration. In a few studies, treatment is administered as a daily×5 dosing schedule repeated every 2 weeks until the tumors reach 10% of the animal's weight. The growth of the solid tumor is monitored twice a week for the duration of the experiment. Tumor size is quantitated using sliding vernier calipers, and the mass is calculated using the formula L×W divided by 2 in mm. Conversion from cubic mm to mg is made assuming unit density. Tumors are not allowed to grow larger than 15% of the mouse's weight, at which point the mouse is euthanized.

FIGS. 6-15 show the results of in vivo assays conducted according to this protocol. Compounds were dissolved in phosphate buffer. The vehicle control was phosphate buffer with no compound. All doses were measured in mg/kg. For the PEGylated compounds, the dose amount was measured by the base compound without consideration for the weight of PEG. The cell lines A549 (human non-small cell lung cancer) and U87 (glioblastoma) were purchased from American Type Culture Collection (ATCC) (Rockville, Md.). The assay results demonstrate that compounds of the present invention inhibit tumor growth.

The present invention provides a method of inhibiting PI3K in mammals, particularly humans, comprising administering a PI3K-inhibiting amount of a compound of the present invention.

One embodiment provides a method of treating a PI3K-dependent condition comprising administering to a subject a PI3K-inhibiting amount of a compound of the present invention. PI3K-dependent conditions include biochemical processes relevant to pain, diabetes, inflammation, platelet aggregation, ischemic heart disease, sclerosis, restenosis, respiratory disorders, HIV, bone resorption, and particularly cancers such as non-small cell lung cancer and brain cancer.

Because PI3K plays a key role in mitogenesis and malignant transformation of cells, compounds that inhibit PI3K have proven useful as anti-tumor agents. Thus, one embodiment of the present invention provides methods of treating cancer by administering a compound of the present invention.

Treating cancer encompasses, but is not limited to inhibiting and/or reducing tumor cell proliferation, tumor cell growth, or tumorigenesis. One skilled in the art would appreciate assays that demonstrate the ability of compounds of the present invention to reduce cell proliferation. For example, cell lines are cultured with a compound of the present invention and then cell proliferation is measured by, for example, an MTS assay or a thymidine incorporation assay. One skilled in the art would appreciate other assays as well.

Exemplary cell proliferation assays demonstrate the minimum concentration of compound sufficient to inhibit tumor growth, i.e., the minimum inhibitory concentration, $IC_{50}$ (μg/ml). Results of cell proliferation assays for exemplary compounds are shown below in Tables 1 and 2. Cell lines LNCaP (human prostate carcinoma), MDA468 (human breast cancer cell), MDA435 (human breast adenocarcinoma), and DU145 (human prostate carcinoma/lymphocytic leukemia) were purchased from American Type Culture Collection (ATCC) (Rockville, Md.). Cells were cultured in RPMI Medium 1640 containing 10% fetal bovine serum (FBS) in a 37° C. incubator containing 5% $CO_2$. All cell culture reagents were purchased from Gibco-BRL (Grand Island, N.Y.). Cells were plated in 96-well culture plates at about 3000 cells per well. One day following plating, compounds or vehicle controls (buffer only) were added to cells. Proliferation assays were performed three days post initiation of treatment.

For a non-radioactive cell proliferation assay, viable cell densities are determined by measuring metabolic conversion (by viable cells) of the dye MTS tatrazolium dye, a cell proliferation assay known by one of skill in the art (MTS assay), a previously established cell proliferation assay. The assay is performed using an assay kit (Promega Corp., Madison, Wis.). The assay plates are incubated for 1-2 hours, and the results are read in a 96-well format plate reader by measuring absorbance at 490 nm. Effect of each compound is calculated as a percentage of control cell growth obtained from vehicle-treated cells grown in the same plate.

The PI3K/AKT/TOR pathway is critical for cell proliferation, growth, survival, and angiogensis. Accordingly, compounds of the present invention may also be useful to inhibit TOR activity. Similar in vivo and in vitro assays to those described above with reference to PI3K can be used to determine the minimum concentration of compound sufficient to inhibit TOR. A human TOR assay and a Rat1-IGF1 assay as described in Examples 67 and 68, respectively was performed with some embodiments of the invention. The results of these assays are shown below in Tables 1 and 2. The minimum concentration of compound sufficient to inhibit TOR, i.e., the minimum inhibitory concentration, $IC_{50}$ (μg/ml), for exemplary compounds is shown below in Tables 1 and 2.

TABLE 1

| Compound as pictured in Figure number | Assay data ($IC_{50}$, μg/ml) | | | | | | |
|---|---|---|---|---|---|---|---|
| | TOR | PI3K FP | Rat1-IGF1 | LNCaP | MDA468 | MDA435 | DU145 |
| 2 | >10 | 0.125 | | 0.1 | 1 | 6 | 1.4 |
| 1 | 10 | 0.09 | | 0.075 | 1 | 6 | 2 |
| 18 | 2.5 | 0.629 | | 0.11 | 0.4 | 6 | 1.5 |
| 16 | 8 | 1.994 | | 0.08 | 0.28 | 5.5 | 1.3 |
| 17 | 1.3 | 0.607 | | 0.14 | 0.5 | 7 | 3 |
| 3 | 4.8 | 0.228 | >0.1 | 3.5 | 5 | 15 | 12 |
| 4 | 16 | 0.596 | 0.1 | 0.09 | 0.3 | 6 | 1.5 |
| 5 | 1.4 | 0.007 | 0.02 | 0.4 | 1.8 | 15 | 10 |
| 6 | 0.66 | 0.07 | 0.02 | 0.55 | 2.01 | >15 | 13 |
| 7 | 0.49 | 0.025 | 0.02 | 0.88 | 2 | >15 | >15 |
| 8 | 4.3 | 0.244 | 0.1 | 0.09 | 0.6 | 5 | 2 |
| 9 | 47 | >2.5 | >0.1 | 9.5 | 10 | 15 | 13 |
| 10 | 0.54 | 0.053 | 0.02 | 1 | 1.8 | >15 | 15 |
| 11 | 0.98 | 0.053 | 0.02 | 0.8 | 1.8 | >15 | 15 |
| 12 | 1.8 | 0.2 | 0.1 | 2.8 | 6 | >15 | >15 |
| 13 | 0.36 | 0.036 | 0.05 | 0.8 | 2 | >15 | 15 |
| 14 | 0.44 | 0.043 | 0.02 | 0.58 | 2 | >15 | 15 |
| 15 | 1.45 | 0.102 | 0.02 | 0.9 | 2.3 | >15 | 15 |
| 17-OH-Wort | 0.076 | 0.0034 | <0.01 | 1 | 2.3 | >15 | 15 |
| 52 | 1.3 | 0.043 | | .25 | 3.85 | | |
| 49 | .83 | 0.044 | | 0.8 | 4.25 | | |
| 41 | .43 | 0.028 | | 1.45 | 5 | | |
| 42 | .85 | 0.014 | | 0.75 | 4.1 | | |
| 43 | 2.8 | 0.027 | | 0.42 | 3.4 | | |
| 55 | 1.75 | 0.081 | | 0.09 | 0.75 | | |
| 63 | 0.31 | | | | | | |
| 64 | 2.0 | 0.0065 | | 0.3 | | | |
| 65 | 0.58 | 1.55 | | | | | |

TABLE 2

Assay data (IC$_{50}$, µg/ml, except where noted)

| Compound as pictured in Figure number | TOR | PI3K IC$_{50}$ nM | Rat1-IGF1 | LNCaP | MDA468 | MDA435 | DU145 |
|---|---|---|---|---|---|---|---|
| 1 | | 179 | | | | | |
| 19 | >10 | 918 | >0.1(hint) | 0.07 | 1.2 | 6 | 1.7 |
| 20 | >10 | 440 | >0.1 | 0.06 | 0.62 | 5 | 1.1 |
| 21 | 2.2 | 22 | 0.1 | 0.16 | 3.9 | 11 | 12 |
| 22 | 0.97 | 52 | 0.1 | 0.29 | 3.5 | 18 | 17 |
| 23 | 0.46 | 33 | 0.1 | 0.28 | 4 | 17 | 17 |
| 24 | >10 | 5398 | >0.1 | 0.13 | 1.05 | 10.05 | 4 |
| 25 | 0.94 | 15 | 0.02 | 0.43 | 4.3 | 16 | 20.5 |
| 26 | 1.4 | 19 | 0.02 | 0.28 | 3.9 | 21 | 17 |
| 27 | 1.35 | 24 | 0.1 | 0.35 | 5 | 30 | 23 |
| 28 | >10 | 131 | >0.1(hint) | 0.12 | 3 | 11 | 8.5 |
| 29 | >10 | 373 | >0.1 | 1.8 | 15 | >30 | 30 |
| 30 | 0.77 | 46 | 0.02 | 0.41 | 4 | 21 | 21 |
| 31 | 0.68 | 9 | 0.1 | 0.4 | 4 | 23 | 21 |
| 32 | 0.15 | 39 | 0.1 | 0.5 | 4.1 | 22 | 20 |
| 33 | 0.39 | 78 | 0.1 | 0.5 | 4.3 | 18 | 20 |
| 34 | 0.59 | 91 | 0.1 | 0.48 | 6 | 22 | 25 |
| 35 | 8 | 1581 | 0.1 | 0.1 | 1.4 | 5.5 | 3 |
| 36 | 1.6 | 199 | 0.1 | 0.09 | 2.3 | 5 | 12 |
| 37 | 6.9 | 193 | 0.1 | 0.2 | 4 | 12 | 21 |
| 38 | 5.1 | 63 | 0.1 | 0.06 | 1.3 | 4 | 2.4 |
| 39 | 6.9 | 770 | 0.1 | 0.043 | 1.2 | 4 | 2.4 |
| 40 | >10 | 444 | >0.1(hint) | 0.085 | 0.75 | 5.5 | 1.85 |
| 4 | >10 | 1002 | NA | 0.05 | 0.51 | 3.5 | 1 |
| 5 | 0.7 | 7 | NA | 0.28 | 2 | 8.2 | 9.5 |
| 8 | 4.7 | 775 | NA | 0.12 | 0.9 | 3.1 | 1.3 |
| 13 | 0.46 | 53 | NA | 0.33 | 3.5 | 13 | 17 |
| 17-OH-Wort | 0.059 | 2 | <0.01 | 0.3 | 3 | 20 | 13 |
| Wortmannin | | 10 | | | | | |
| 51 | | 616.5 | >0.2 | 2.8 | 30 | | |
| 50 | | 7583.1 | >0.1(hint) | 0.25 | 2.5 | | |
| 44 | 0.59 | 60.2 | 0.02 | 0.37 | 3 | | |
| 45 | >10 | 369.2 | 0.1 | 0.65 | 5 | | |
| 46 | 0.48 | 5.1 | 0.02 | 0.65 | 3.3 | | |
| 47 | 0.34 | 63.3 | 0.05 | 0.9 | 5.8 | | |
| 48 | 0.43 | 36.1 | 0.02 | 0.5 | 3 | | |
| 60 | 0.2 | 7 | | 0.33 | 2 | | |

The present invention also provides pharmaceutical compositions comprising a compound of the present invention and a pharmaceutically acceptable carrier.

Pharmaceutical compositions of this invention may be administered alone or in combination with other therapeutically effective compounds or therapies for the treatment or prevention of a pathological condition or disorder mediated in a mammal. Likewise, the compounds of this invention may be provided as a single compound or in combination with other compounds.

Inhibition of PI3K might be expected to enhance therapeutic activity of other agents that modulate growth factor signaling, cytokine response and cell cycle control known in the art, such as, but not limited to cytokines, interferon, rapamycin, HER2/EGFR inhibitors, MEK inhibitors, interferon-α, Src kinase inhibitors and mTor inhibitors.

HER2 is human epidermal growth factor receptor 2 and is expressed on the surface of many human tumors, including breast cancers. A HER2 inhibitor preferably inhibits the signaling pathways that mediate cell proliferation and specifically inhibits HER2 tyrosine kinase and is therefore also useful as a therapeutic agent for suppressing the growth of HER2-expressing cancers. HER2 inhibitors are known in the art. An exemplary HER2 inhibitor is (E)-N-{4-[3-chloro-4-(2-pyridinyl methoxy)anilino]-3-cyano-7-ethoxy-6-quinolinyl}-4-(dimethylamino)-2-butenamide.

Human epidermal growth factor (EGF) is a polypeptide, which exerts biologic effects by binding to a specific cell membrane epidermal growth factor receptor (EGFR/ErbB-1). Many types of cancer cells display enhanced EGFR expression on their cell surface. Enhanced expression of the EGFR on cancer cells has been associated with excessive proliferation and metastasis. Too much of its ligand, EGF, has been identified with runaway cell growth, resulting in a variety of cancers including colorectal, head and neck, ovarian, prostate, breast, and lung. When EGF binds to EGFR, it triggers a chemical signaling process that encourages growth and division. An inhibitor of EGFR preferably interrupts either the interaction of EGF with its receptor EGFR or inhibits the internal chemical signaling process to stop the production of the chemical that gives the go-ahead for cell division. An exemplary EGFR inhibitor is 4-Dimethylamino-but-2-enoic acid [4-(3-chloro-4-fluoro-phenylamino)-3-cyano-7-ethoxy-quinolin-6-yl]-amide.

MEK is a family of enzymes known as MEK kinases, which are groups of MAP (mitogen-associated protein kinase) and Erk (extracellular signal-regulated) Kinases. These are enzymes that regulate phosphorylation of substrates in mammals. Preferable MEK inhibitors are those compounds which inhibit the MEK 1 and MEK 2 enzymes without substantial inhibition of other such enzymes. An exemplary MEK inhibitor is 4-({3-chloro-4-[(1-methyl-1H-imidazol-2-yl)thio]phenyl}amino)-6-methoxy-7-(4-pyrrolidin-1-ylpiperidin-1-yl)quinoline-3-carbonitrile. Another exemplary MEK inhibitor is a MAP kinase inhibitor known as UO126 or chemically known as 1,4-diamino-2,3,-dicyano-1,4-bis[2-aminophenylthio]butadiene.

Src is a protein tyrosine kinase (PTK) associated with cellular membranes and is involved in signal transduction and growth regulation pathways. It transmits cellular signals by transferring the gamma phosphate of ATP to the side chain of tyrosine residues on substrate proteins. To this date, nine members of the Src protein tyrosine kinase family have been discovered. The members are Src, Yes, Fyn, Fgr, Blk, Lck, Lyn, Hck, and Yrk. Fgr, Blk, Lck, Lyn, Hck, and Yrk are expressed and active primarily in hematopoietic cells. Alterations in the phosphorylation of Src substrates are key events in cellular signaling. Most normal cells contain very low levels and activity of Src and the enzyme is not required for the establishment or maintenance of cell viability. Src activity is greatly increased in many human cancers.

Changes in Src activity are associated with changes in the cell cycle and alterations in the regulation of Src activity have been associated with neoplasia. Inhibition of Src would have the effect of interrupting the signal transduction pathways in which it participates and would thereby reduce the rate of growth of cancer cells. Drugs directed to inhibit the Src family may have the advantage of limited or no systemic toxicity but high specificity for tumors shown to have elevated activity of one or more members of the Src family. Exemplary Src inhibitors are 4-(2,4-dichloro-5-methoxy-phenylamino)-5-methoxy-7-[3-(4-methyl-piperazin-1-yl)-propoxy]-quinoline-3-carbonitrile and 4-(2,4-dichloro-5-methoxyanilino)-7-{5-[(4-methyl-1-piperazinyl)methyl]-2-pyridinyl}-3-carbonitrile.

CCI-779 is an ester of rapamycin and inhibitor of mammalian target of rapamycin (mTOR) currently in Phase II clinical development for the treatment of patients with cancer. CCI-779 interacts with mTOR and inhibits its kinase activity, resulting in inhibition of the mTOR-regulated translational controllers p70(s6) kinase.

Figure 19A:
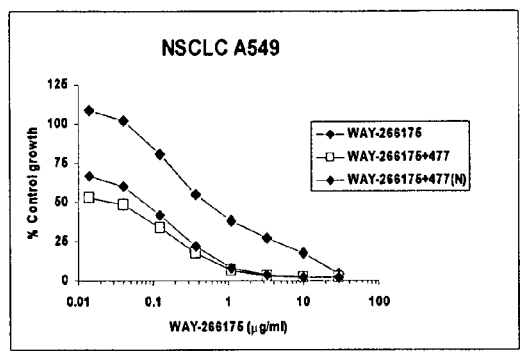
FIGS. 19A and B show that compound 4 in combination with an MEK inhibitor 2-(2-chloro-4-iodoanilino)-N-(cycloprorylmethoxy-3,4-difluobenzamide) demonstrated synergistic growth inhibition in non-small cell lung cancer (NSCLC) cell lines.
Figure 19B:
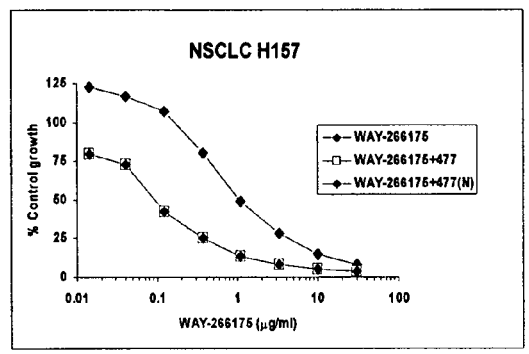
Figure 20A:
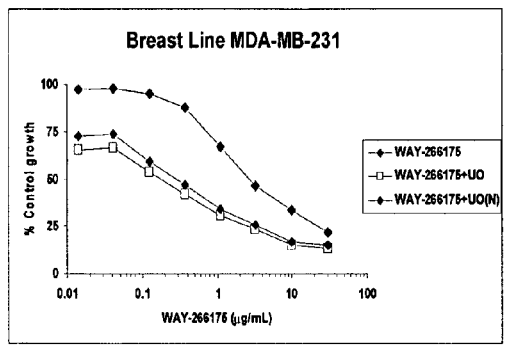
FIG. 20A shows that compound 4 in combination with an MEK inhibitor 2-(2-chloro-4-iodoanilino)-N-(cycloprorylmethoxy-3,4-difluobenzamide) demonstrated synergistic growth inhibition in MDA231 breast tumor cells.
Figure 20B:
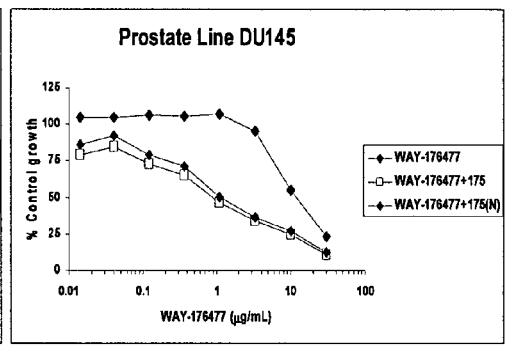
FIG. 20B shows that compound 4 in combination with an MEK inhibitor 2-(2-chloro-4-iodoanilino)-N-(cycloprorylmethoxy-3,4-difluobenzamide) demonstrated synergistic growth inhibition in DU145 prostrate tumor cells.
Figure 21:
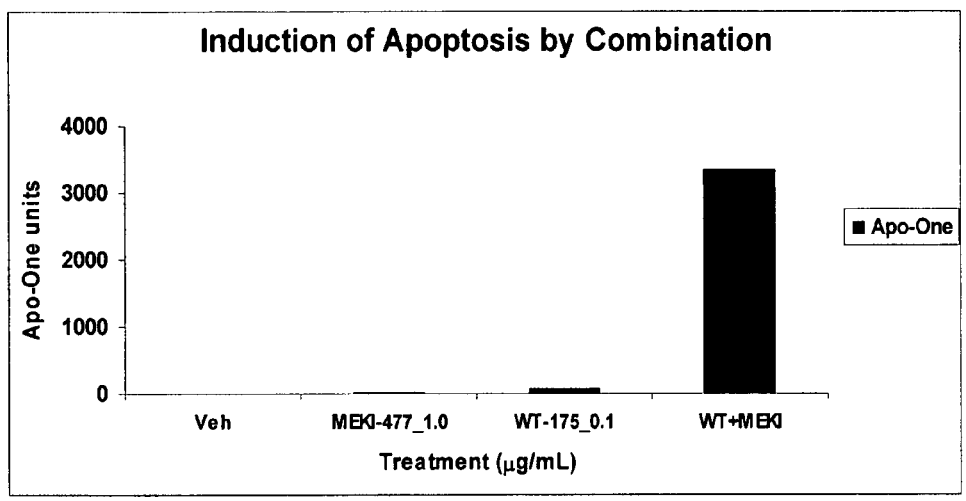
FIG. 21 shows synergistic induction of apoptosis in HCT116 cells by combination treatment of compound 4 with MEK inhibitor 2-(2-chloro-4-iodoanilino)-N-(cycloproryl-methoxy-3,4-difluobenzamide).
Figure 22:
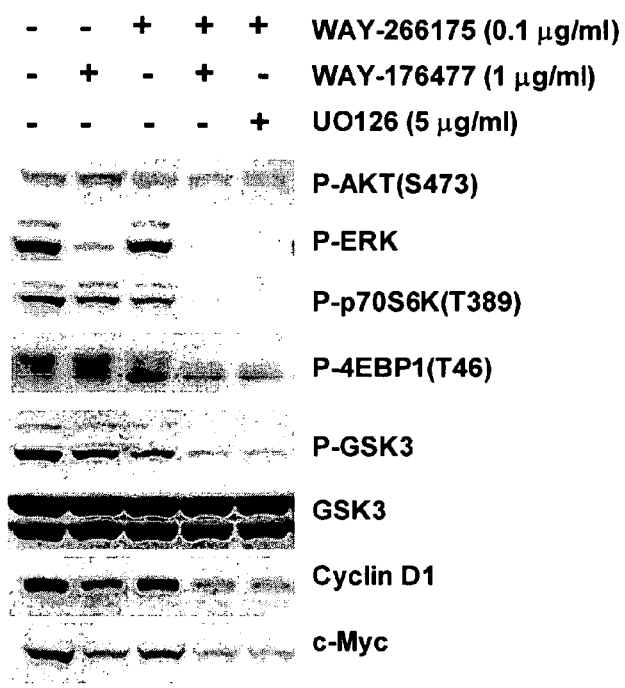
FIG. 22 provides Western blotting analysis of HCT116 cells on various molecular pathway markers of PI3K, MEK and cell cycle control. Cells were treated with single or combination agents for 16 hours.
Figure 23:
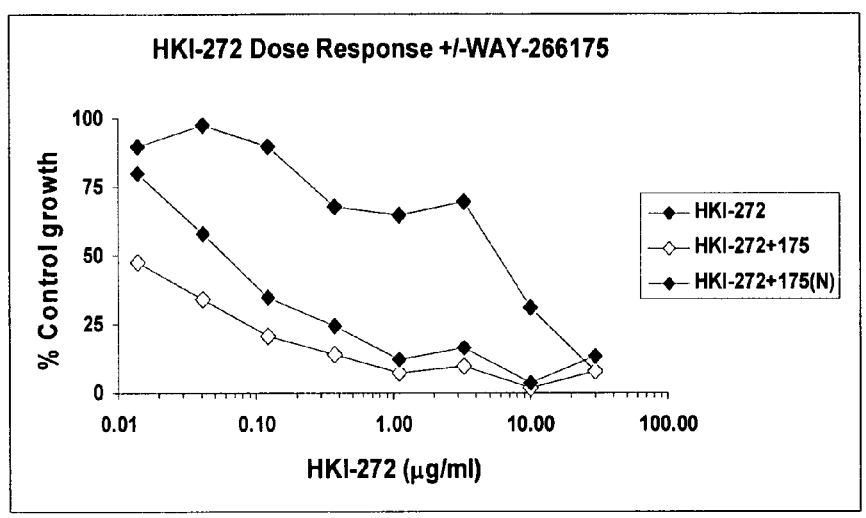
FIG. 23 shows that HER2/neu inhibitor (E)-N-{4-[3-chloro-4-(2-pyridinyl methoxy)anilino]-3-cyano-7-ethoxy-6-quinolinyl}-4-(dimethylamino)-2-butenamide (referred to as "HKI-272") in combination with compound 4 (0.1 µg/ml) synergistically inhibited growth of HER2/Neu-overexpressing MDA361-DYT2 breast tumor cells.

Compounds of the present invention confer a synergistic growth inhibition in several tumor models when combined with inhibitors of various cell growth or cell cycle modulators, tyrosine kinases or cytokines. The present inventors have discovered that a synergistic antitumor activity can be achieved by compounds of the present invention when combined with inhibitors of MEK, Her2/Neu and mTOR. Specifically, compounds of the present invention have shown synergistic anticancer activity by combined inhibitions of PI3K and MEK in colon (see FIGS. 16-18, 21, 22 and 26) lung (see FIG. 19), prostate (see FIG. 20) and breast cancer cell lines (see FIGS. 20, 23, 25, and 27). See also example 69.

In response to treatment by 17-hydroxywortmanin and compounds of the present invention, PI3K pathway markers are well inhibited in both sensitive and resistant cells. It is noted that cell cycle proteins cyclin DI and c-Myc are only efficiently inhibited in sensitive cells. It is generally observed that specific inhibitors of PI3K or MEK do not cross-inhibit each other's pathway markers. As suggested by recent literature (Mirza A M, et al., *Mol Cell Biol.* 2004 December; 24(24): 10868-81; Xing D, et al., *Proc Natl Acad Sci* USA. 2005 May 10; 102(19):6936-41; Gera J F, et al., *J Biol Chem.* January 23; 279(4):2737-46; and Shi Y, et al., *J Biol Chem.* 2005 Mar. 25; 280(12):10964-73), many critical cellular functions, e.g., expression of cyclin D1 and c-Myc, are regulated by transcription and translation involving both cooperative and independent signaling pathways of PI3K and Ras/MEK. The present inventors found that constitutive phosphorylation and activation of ERK (a substrate of MEK) in many cell models correlated with a reduced sensitivity to compound of the present invention. Combination inhibition of PI3K and Ras/MEK pathways seem therefore particularly attractive for broad anticancer applications as both pathways are essential in cellular growth and survival.

Figure 24:
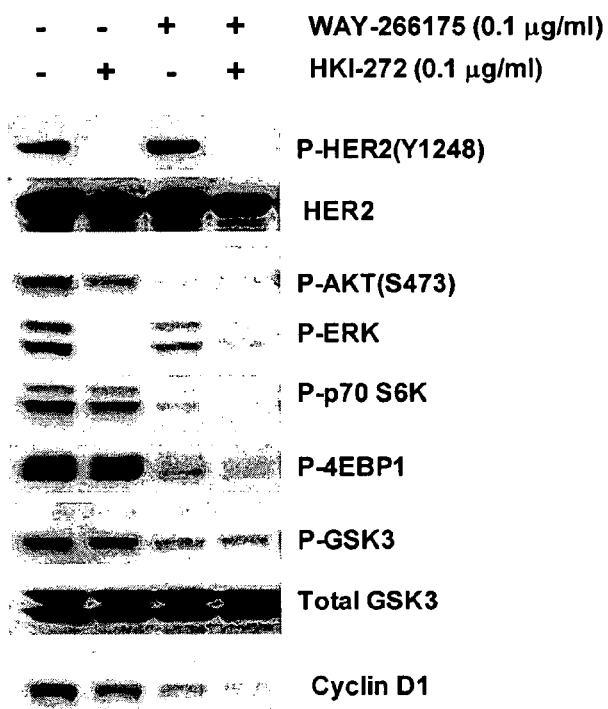
FIG. 24 provides Western blot analysis of MDA361-DYT2 on various molecular pathway markers of PI3K, HER2/Neu, ERK and cell cycle control. Cells were treated for 16 hr.
Figure 25:
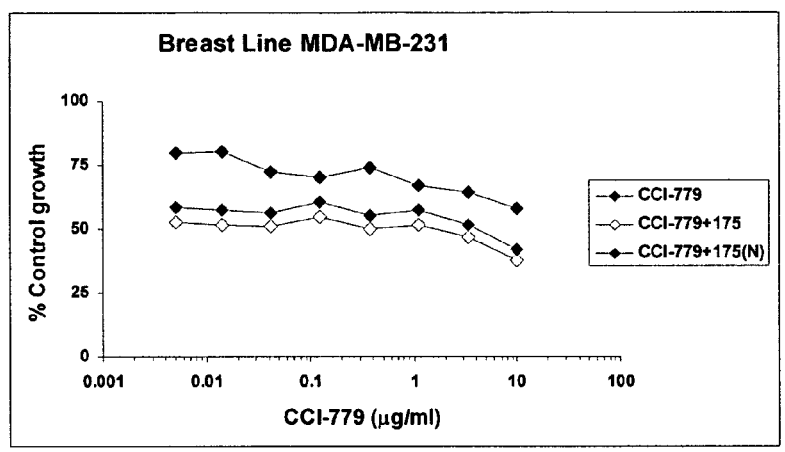
FIG. 25 shows that mTOR inhibitor CCI-779 in combination with compound 4 (0.1 µg/ml) synergistically inhibited growth of MDA-MB-231 breast cells.
Figure 26A:
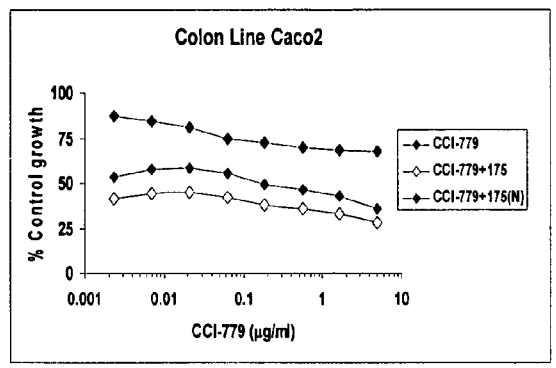
FIGS. 26A and B show that mTOR inhibitor CCI-779 in combination with compound 4 (0.1 µg/ml) synergistically inhibited growth of colon tumor cell lines.
Figure 26B:
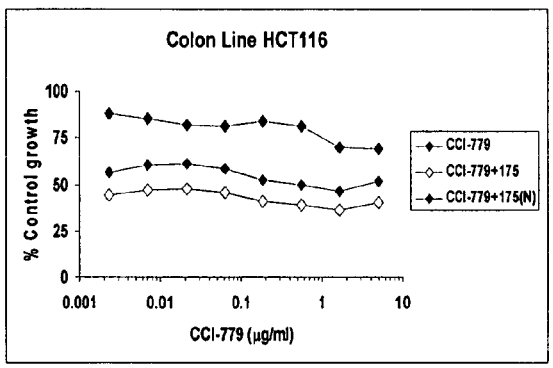

Compounds of the present invention also provide synergistic anticancer activity when combined with a HER2/Neu inhibitor in a HER2/Neu positive breast cancer line. Recent reports (Bianco R, et al., *Oncogene.* 2003 May 8; 22(18): 2812-22 and Nagata Y, et al., *Cancer Cell.* 2004 August; 6(2): 117-27) indicated that constitutive PI3K signaling caused by PTEN-deficiency confers resistance to an EGFR kinase inhibitor and the HER2 antibody Herceptin, and that such resistance in both cases could be overcome by inhibition of PI3K with the known inhibitor LY294002. The present inventors have found that the breast tumor line MDA361-DYT2 expresses a high level of Her2/Neu but it is resistant to the Her2/Neu kinase inhibitor HKI-272 (also known as: (E)-N-{4-[3-chloro-4-(2-pyridinyl methoxy)anilino]-3-cyano-7-ethoxy-6-quinolinyl}-4-(dimethylamino)-2-butenamide) in vitro and in vivo. Although treatment of MDA361-DYT2 with 0.1 μg/ml of HKI-272 completely inhibited phosphorylated forms of Her2/Neu and ERK, it had little effect on AKT pathway markers indicating a constitutive activation of the PI3K/AKT pathway. Thus, combination inhibition of PI3K (with a compound of the present invention) and a Her2/Neu inhibitor may provide synergistic efficacy in Herceptin and/or HKI-272 resistant breast tumors. See FIGS. 23 and 24.

Compounds of the present invention also provide synergistic anticancer activity when combined with an mTOR inhibitor in breast and colon tumor cell lines. The PI3K and mTOR are two major components in the PI3K/AKT/mTOR pathway that is frequently deregulated in cancer. PI3K and mTOR are regulated by a diverse set of overlapping as well as independent signals of growth factors, nutrients and energy supply. Deregulated PI3K and mTOR may act synergistically in promoting tumor growth and survival. Consistent with this notion, the tumor suppressor PTEN (cellular repressor of PI3K) and TSC2 (cellular repressor of mTOR) were shown to synergistically suppress the severity of a subset of tumors specific to loss of each of these genes (Manning B D, et al., *Genes Dev.* 2005 Jul. 18.). In malignant glioma cells, combination of TOR inhibition by Rapamycin and PI3K/AKT inhibition resulted a synergistic antitumor effect via an augmented autophagy (Takeuchi H, et al., *Cancer Res.* 2005 Apr. 15; 65(8):3336-46). In a new report, combination treatment by Rapamycin and the PI3K inhibitor LY294002 overcame Rapa-induced eIF4E phosphorylation in H157 lung tumor cells, thereby enhancing antitumor activity (Sun S Y, et al., *Cancer Res.* 2005 Aug. 15; 65(16):7052-8). It has been previously observed that superior antitumor in vivo efficacy was achieved by combination of minimal doses of PI3K inhibitor PEG-17-hydroxywortmanin and mTOR inhibitor Peg-Rapa (Yu K, et al., *Cancer Biol Ther.* 2005 May 28; 4(5):538-45). In the current combination experiments, compound 4 in combination with the mTOR inhibitor CCI-779 conferred an additive inhibition in PTEN-negative (CCI-779 sensitive) tumor cells and synergistic inhibition in colon tumor cells that were otherwise less sensitive to the single agent treatment by CCI-779 or by other 17-hydroxywortmanning (17-HWT) analogs.

Compounds 4 and 5 of the present invention in combination with structurally distinct MEK inhibitors UO126 (which is also known as 1,4-diamino-2,3-dicyano-1,4-bis[2-aminophenylthio]butadiene) and (2-(2-chloro-4-iodoanilino)-N-(cycloprorylmethoxy-3,4-difluobenzamide) demonstrated broad synergistic growth inhibition in colon carcinoma cell lines (HCT116, HT29, SW620, SW480, LS-174T, Caco2 and Lovo), in NSCLC cell lines (A549 and H157), prostate line DU145 and breast line MDA231.

In the HCT 116 model, synergistic growth inhibition by the combination was achieved by induction of apoptosis. Western analysis on HCT116 colon line showed modulation of signaling molecules consistent with synergistic antitumor activity.

Compound 4 in combination with the Her2/Neu inhibitor HKI-272 demonstrated synergistic growth inhibition in Her2/Neu-overexpressing-MDA361-DYT2 line that is resistant to HKI-272. Western analysis showed modulation of biochemical markers consistent with synergistic antitumor activity.

Compound 4 in combination with the mTOR inhibitor CCI-779 demonstrated additive growth inhibition in PTEN-negative breast tumor cells and synergistic growth inhibition in CCI-779 resistant breast and colon tumor cell lines.

Wortmannin derivatives synergize with interferon-α (Intron-A) in causing tumor regression and enhancing anticancer activity of pegylated-rapamycin, a specific inhibitor of mTOR kinase. Yu, K., et al., *Cancer Biol. Ther.* (2005) 28:4 (5).

Accordingly, the present invention provides a method of inhibiting tumor cell growth or treating cancer comprising administering a compound of the present invention in combination with an inhibitor a growth factor signaling cascade, a cytokine response, etc., including, but not limited to an inhibitor of MEK, Her2/Neu, mTor, Src, cyotkines and interferon-α (Intron-A).

A cellular inhibition of PI3K or AKT leads to a reduction in survival, a critical process underlying the anticancer activity of many standard cancer therapies. However, in many cases, tumor cells rapidly develop chemo-resistance. One cellular mechanism of resistance relates to constitutive elevation of PI3K/AKT pathway. Thus, combination treatment of cytotoxics (such as, but not limited to, irinotecan, 5-FU, taxol, cisplatin, adriamycin, oxaliplatin, and cyclophasphamide) with an inhibitor of PI3K may further augment efficacy in an initial therapy and may also help in a restoration of chemo-sensitivity in recurring therapies. Wortmannin derivatives can potentiate paclitaxel anticancer efficacy in lung cancer and in glioma.

The pharmaceutical compositions of the present invention may contain one or more excipients. Excipients are added to the composition for a variety of purposes.

Diluents increase the bulk of a solid pharmaceutical composition, and may make a pharmaceutical dosage form containing the composition easier for the patient and caregiver to handle. Diluents for solid compositions include, for example, microcrystalline cellulose (e.g. Avicel®), microfine cellulose, lactose, starch, pregelatinized starch, calcium carbonate, calcium sulfate, sugar, dextrates, dextrin, dextrose, dibasic calcium phosphate dihydrate, tribasic calcium phosphate, kaolin, magnesium carbonate, magnesium oxide, maltodextrin, mannitol, polymethacrylates (e.g. Eudragit®), potassium chloride, powdered cellulose, sodium chloride, sorbitol and talc.

Solid pharmaceutical compositions that are compacted into a dosage form, such as a tablet, may include excipients whose functions include helping to bind the active ingredient and other excipients together after compression. Binders for solid pharmaceutical compositions include acacia, alginic acid, carbomer (e.g. carbopol), carboxymethylcellulose sodium, dextrin, ethyl cellulose, gelatin, guar gum, hydrogenated vegetable oil, hydroxyethyl cellulose, hydroxypropyl cellulose (e.g. Klucel®), hydroxypropyl methyl cellulose (e.g. Methocel®), liquid glucose, magnesium aluminum silicate, maltodextrin, methylcellulose, polymethacrylates, povidone (e.g. Kollidon®, Plasdone®), pregelatinized starch, sodium alginate and starch.

The dissolution rate of a compacted solid pharmaceutical composition in the patient's stomach may be increased by the addition of a disintegrant to the composition. Disintegrants include alginic acid, carboxymethylcellulose calcium, carboxymethylcellulose sodium (e.g. Ac-Di-Sol®, Primellose®), colloidal silicon dioxide, croscarmellose sodium, crospovidone (e.g. Kollidon®, Polyplasdone®), guar gum, magnesium aluminum silicate, methyl cellulose, microcrystalline cellulose, polacrilin potassium, powdered cellulose, pregelatinized starch, sodium alginate, sodium starch glycolate (e.g. Explotab®) and starch.

Glidants can be added to improve the flowability of a non-compacted solid composition and to improve the accuracy of dosing. Excipients that may function as glidants include colloidal silicon dioxide, magnesium trisilicate, powdered cellulose, starch, talc and tribasic calcium phosphate.

When a dosage form such as a tablet is made by the compaction of a powdered composition, the composition is subjected to pressure from a punch and dye. Some excipients and active ingredients have a tendency to adhere to the surfaces of the punch and dye, which can cause the product to have pitting and other surface irregularities. A lubricant can be added to the composition to reduce adhesion and ease the release of the product from the dye. Lubricants include magnesium stearate, calcium stearate, glyceryl monostearate, glyceryl palmitostearate, hydrogenated castor oil, hydrogenated vegetable oil, mineral oil, polyethylene glycol, sodium benzoate, sodium lauryl sulfate, sodium stearyl fumarate, stearic acid, talc and zinc stearate.

Flavoring agents and flavor enhancers make the dosage form more palatable to the patient. Common flavoring agents and flavor enhancers for pharmaceutical products that may be included in the composition of the present invention include maltol, vanillin, ethyl vanillin, menthol, citric acid, fumaric acid, ethyl maltol and tartaric acid.

Solid and liquid compositions may also be dyed using any pharmaceutically acceptable colorant to improve their appearance and/or facilitate patient identification of the product and unit dosage level.

In liquid pharmaceutical compositions of the present invention, the compound of formula I and any other solid excipients are dissolved or suspended in a liquid carrier such as water, vegetable oil, alcohol, polyethylene glycol, propylene glycol or glycerin.

Liquid pharmaceutical compositions may contain emulsifying agents to disperse uniformly throughout the composition an active ingredient or other excipient that is not soluble in the liquid carrier. Emulsifying agents that may be useful in liquid compositions of the present invention include, for example, gelatin, egg yolk, casein, cholesterol, acacia, tragacanth, chondrus, pectin, methyl cellulose, carbomer, cetostearyl alcohol and cetyl alcohol.

Liquid pharmaceutical compositions of the present invention may also contain a viscosity enhancing agent to improve the mouth-feel of the product and/or coat the lining of the gastrointestinal tract. Such agents include acacia, alginic acid bentonite, carbomer, carboxymethylcellulose calcium or sodium, cetostearyl alcohol, methyl cellulose, ethylcellulose, gelatin guar gum, hydroxyethyl cellulose, hydroxypropyl cellulose, hydroxypropyl methyl cellulose, maltodextrin, polyvinyl alcohol, povidone, propylene carbonate, propylene glycol alginate, sodium alginate, sodium starch glycolate, starch tragacanth and xanthan gum.

Sweetening agents such as sorbitol, saccharin, sodium saccharin, sucrose, aspartame, fructose, mannitol and invert sugar may be added to improve the taste.

Preservatives and chelating agents such as alcohol, sodium benzoate, butylated hydroxy toluene, butylated hydroxyanisole and ethylenediamine tetraacetic acid may be added at levels safe for ingestion to improve storage stability.

According to the present invention, a liquid composition may also contain a buffer such as guconic acid, lactic acid, citric acid or acetic acid, sodium guconate, sodium lactate, sodium citrate or sodium acetate. Selection of excipients and the amounts used may be readily determined by the formulation scientist based upon experience and consideration of standard procedures and reference works in the field.

The solid compositions of the present invention include powders, granulates, aggregates and compacted compositions. The dosages include dosages suitable for oral, buccal, rectal, parenteral (including subcutaneous, intramuscular, and intravenous), inhalant and ophthalmic administration. The most suitable administration in any given case will depend on the nature and severity of the condition being treated. The dosages may be conveniently presented in unit dosage form and prepared by any of the methods well-known in the pharmaceutical arts.

Dosage forms include solid dosage forms like tablets, powders, capsules, suppositories, sachets, troches and lozenges, as well as liquid syrups, suspensions and elixirs.

The dosage form of the present invention may be a capsule containing the composition, for example, a powdered or granulated solid composition of the invention, within either a hard or soft shell. The shell may be made from gelatin and optionally contain a plasticizer such as glycerin and sorbitol, and an opacifying agent or colorant.

The active ingredient and excipients may be formulated into compositions and dosage forms according to methods known in the art.

A composition for tableting or capsule filling may be prepared by wet granulation. In wet granulation, some or all of the active ingredients and excipients in powder form are blended and then further mixed in the presence of a liquid, typically water, that causes the powders to clump into granules. The granulate is screened and/or milled, dried and then screened and/or milled to the desired particle size. The granulate may then be tableted, or other excipients may be added prior to tableting, such as a glidant and/or a lubricant.

A tableting composition may be prepared conventionally by dry blending. For example, the blended composition of the actives and excipients may be compacted into a slug or a sheet and then comminuted into compacted granules. The compacted granules may subsequently be compressed into a tablet.

As an alternative to dry granulation, a blended composition may be compressed directly into a compacted dosage form using direct compression techniques. Direct compression produces a more uniform tablet without granules. Excipients that are particularly well suited for direct compression tableting include microcrystalline cellulose, spray dried lactose, dicalcium phosphate dihydrate and colloidal silica. The proper use of these and other excipients in direct compression tableting is known to those in the art with experience and skill in particular formulation challenges of direct compression tableting.

A capsule filling of the present invention may include any of the aforementioned blends and granulates that were described with reference to tableting, however, they are not subjected to a final tableting step.

Methods of administration of a pharmaceutical composition encompassed by the invention are not specifically restricted, and can be administered in various preparations depending on the age, sex, and symptoms of the patient. For example, tablets, pills, solutions, suspensions, emulsions, granules and capsules may be orally administered. Injection preparations may be administered individually or mixed with injection transfusions such as glucose solutions and amino acid solutions intravenously. If necessary, the injection preparations are administered singly intramuscularly, intracutaneously, subcutaneously or intraperitoneally. Suppositories may be administered into the rectum.

The amount of the compound of formula I contained in a pharmaceutical composition according to the present invention is not specifically restricted, however, an effective amount is a dose that is sufficient to treat, ameliorate, or reduce the targeted symptoms. The dosage of a pharmaceutical composition according to the present invention will depend on the method of use, the age, sex, and condition of the patient.

Having described the invention, the invention is further illustrated by the following non-limiting examples.

EXAMPLES

Example 1

Preparation of (1E,4S,4aR,5R,6aS,7S,9aR)-1-[(diethylamino)methylene]-7,11-dihydroxy-4-(methoxymethyl)-4a,6a-dimethyl-2,10-dioxo-1,2,4,4a,5,6,6a,7,8,9,9a,10-dodecahydroindeno[4,5-h]isochromen-5-yl acetate To a solution of 50 mg (0.116 mmol) 17-hydroxywortmannin in 1 mL $CH_2Cl_2$ is added 22.5 mL (0.217 mmol) diethylamine. The reaction mixture is stirred at room temperature for 2 hours 30 minutes and then concentrated in vacuo to give an orange paste. The residue is dissolved in ethyl actate (EtOAc) and precipitated with hexane. The precipitate is washed two times with hexane to give 45 mg (77%) product as an orange solid. HRMS (ESI) m/z calcd for $C_{27}H_{37}NO_8$ 503.25206, found: 504.25747 $(M+H)^{+1}$.

Example 2

Preparation of (1E,4S,4aR,5R,6aS,7S,9aR)-7,11-dihydroxy-4-(methoxymethyl)-4a,6a-dimethyl-2,10-dioxo-1-(Pyrrolidin-1-ylmethylene)-1,2,4,4a,5,6,6a,7,8,9,9a,10-dodecahydroindeno[4,5-h]isochromen-5-yl acetate To a solution of 50 mg (0.116 mmol) 17-hydroxywortmannin in 1 mL methylene chloride ($CH_2Cl_2$) is added 12.1 mL (0.145 mmol) pyrrolidine. The reaction mixture is stirred at room temperature for 2 hours and then concentrated in vacuo. The residue is dissolved in EtOAc and precipitated with hexane. The precipitate is washed two times with hexane to give 40 mg (68.7%) product as a yellow solid. HRMS (ESI) m/z calcd for $C_{27}H_{35}NO_8$ 501.2364, found: 502.24250 $(M+H)^{+1}$.

Example 3

Preparation of (1E,4S,4aR,5R,6aS,7S,9aR)-1-(anilinomethylene)-7,11-dihydroxy-4-(methoxymethyl)-4a,6a-dimethyl-2,10-dioxo-1,2,4,4a,5,6,6a,7,8,9,9a,10-dodecahydroindeno[4,5-h]isochromen-5-yl acetate To a solution of 50 mg (0.116 mmol) 17-hydroxywortmannin in 1 mL $CH_2Cl_2$ is added 26.2 mL (0.287 mmol) aniline. The reaction mixture is stirred at room temperature for 1 week and then concentrated in vacuo. The residue is dissolved in EtOAc and triturated with hexane to give a yellow powder. The yellow powder is purified by silica gel chromatography, (hexane/EtOAc) to give an oil. The oil is triturated with hexane to give 26 mg (42.8%) product as an orange powder. HRMS (ESI) m/z calcd for $C_{29}H_{33}NO_8$ 523.22074, found: 524.22692 $(M+H)^{+1}$.

Example 4

Preparation of (1E,4S,4aR,5R,6aS,7S)-1-{[tert-butyl(2-hydroxyethyl)amino]methylene}-7,11-dihydroxy-4-(methoxymethyl)-4a,6a-dimethyl-2,10-dioxo-1,2,4,4a,5,6,6a,7,8,9,9a,10-dodecahydroindeno[4,5-h]isochromen-5-yl acetate To a solution of 50 mg (0.12 mmol) 17-hydroxywortmannin in 0.5 mL $CH_2Cl_2$ is added 28.1 mg (0.24 mmol) 2-(tert-butylamino)-ethanol. The reaction mixture is stirred at room temperature overnight. $CH_2Cl_2$ is removed in vacuo. The residue is triturated with diethyl ether ($Et_2O$) to give 32 mg (48.7%) product as an orange powder. MS (ESI) m/z 548.3 (M+1).

Example 5

Preparation of (1E,4S,4aR,5R,6aS,7S)-1-{[[3-(dimethylamino)propyl](methyl)amino]methylene}-7,11-dihydroxy-4-(methoxymethyl)-4a,6a-dimethyl-2,10-dioxo-1,2,4,4a,5,6,6a,7,8,9,9a,10-dodecahydroindeno[4,5-h]isochromen-5-yl acetate To a solution of 50 mg (0.12 mmol) 17-hydroxywortmannin in 0.5 mL $CH_2Cl_2$ is added 27.9 mg (0.24 mmol) N,N,N'-trimethyl-1,3-propanediamine. The reaction mixture is stirred at room temperature overnight. $CH_2Cl_2$ is removed in vacuo. The residue is triturated with $Et_2O$ to give 24 mg (36.6%) product as an orange powder. MS (ESI) m/z 547.3 (M+1).

Example 6

Preparation of (1E,4S,4aR,5R,6aS,7S)-7,11-dihydroxy-4-(methoxymethyl)-4a,6a-dimethyl-1-{[methyl(1-methylpyrrolidin-3-yl)amino]methylene}-2,10-dioxo-1,2,4,4a,5,6,6a,7,8,9,9a,10-dodecahydroindeno[4,5-h]isochromen-5-yl acetate To a solution of 50 mg (0.12 mmol) 17-hydroxywortmannin in 0.5 mL $CH_2Cl_2$ is added 27.4 mg (0.24 mmol) N,N'-dimethyl-3-aminopyrrolidine. The reaction mixture is stirred at room temperature overnight. $CH_2Cl_2$ is removed in vacuo. The residue is triturated with $Et_2O$ to give 25 mg (38%) product as an orange powder.

Example 7

Preparation of (1E,4S,4aR,5R,6aS,7S)-1-[(4-cyclohexylpiperazin-1-yl)methylene]-7,11-dihydroxy-4-(methoxymethyl)-4a,6a-dimethyl-2,10-dioxo-1,2,4,4a,5,6,6a,7,8,9,9a,10-dodecahydroindeno[4,5-h]isochromen-5-yl acetate To a solution of 50 mg (0.12 mmol) 17-hydroxywortmannin in 0.5 mL $CH_2Cl_2$ is added 40.4 mg (0.24 mmol) 1-cyclohexylpiperazine. The reaction mixture is stirred at room temperature overnight. $CH_2Cl_2$ is removed in vacuo. The residue is triturated with $Et_2O$ to give 16 mg (22%) product as an orange powder. MS (ESI) m/z 599.35 (M+1).

Example 8

Preparation of (1E,4S,4aR,5R,6aS,7S)-1-{[butyl(methyl)amino]methylene}-7,11-dihydroxy-4-(methoxymethyl)-4a,6a-dimethyl-2,10-dioxo-1,2,4,4a,5,6,6a,7,8,9,9a,10-dodecahydroindeno[4,5-h]isochromen-5-yl acetate To a solution of 50 mg (0.12 mmol) 17-hydroxywortmannin in 0.5 mL $CH_2Cl_2$ is added 20.9 mg (0.24 mmol) N-methylbutylamine. The reaction mixture is stirred at room temperature overnight. $CH_2Cl_2$ is removed in vacuo. The residue is triturated with $Et_2O$ to give 38 mg (61.2%) product as an orange powder. MS (ESI) m/z 518.25 (M+1).

Example 9

Preparation of (1E,4S,4aR,5R,6aS,7S)-1-{[cyclohexyl(methyl)amino]methylene}-7,11-dihydroxy-4-(methoxymethyl)-4a,6a-dimethyl-2,10-dioxo-1,2,4,4a,5,6,6a,7,8,9,9a,10-dodecahydroindeno[4,5-h]isochromen-5-yl acetate To a solution of 50 mg (0.12 mmol) 17-hydroxywortmannin in 0.5 mL $CH_2Cl_2$ is added 27.2 mg (0.24 mmol) cyclohexyl-methyl-amine. The reaction mixture is stirred at room temperature overnight. $CH_2Cl_2$ is removed in vacuo. The residue is triturated with $Et_2O$ to give 30 mg (46%) product as an orange powder. MS (ESI) m/z 544.25 (M+1).

Example 10

Preparation of (1E,4S,4aR,5R,6aS,7S)-1-[(4-benzylpiperazin-1-yl)methylene]-7,11-dihydroxy-4-(methoxymethyl)-4a,6a-dimethyl-2,10-dioxo-1,2,4,4a,5,6,6a,7,8,9,9a,10-dodecahydroindeno[4,5-h]isochromen-5-yl acetate To a solution of 50 mg (0.12 mmol) 17-hydroxywortmannin in 0.5 mL $CH_2Cl_2$ is added 42.3 mg (0.24 mmol) 1-benzyl-piperazine. The reaction mixture is stirred at room temperature overnight. $CH_2Cl_2$ is removed in vacuo. The residue is triturated with $Et_2O$ to give 13 mg (17.8%) product as an orange powder. MS (ESI) m/z 607.2 (M+1).

Example 11

Preparation of (1E,4S,4aR,5R,6aS,7S)-7,11-dihydroxy-4-(methoxymethyl)-4a,6a-dimethyl-2,10-dioxo-1-(piperidin-1-ylmethylene)-1,2,4,4a,5,6,6a,7,8,9,9a,10-dodecahydroindeno[4,5-h]isochromen-5-yl acetate To a solution of 50 mg (0.12 mmol) 17-hydroxywortmannin in 0.5 mL $CH_2Cl_2$ is added 20.4 mg (0.24 mmol) piperidine. The reaction mixture is stirred at room temperature overnight. $CH_2Cl_2$ is removed in vacuo. The residue is triturated with $Et_2O$ to give 33 mg (53.3%) product as an orange powder. MS (ESI) m/z 516.25 (M+1).

Example 12

Preparation of (1E,4S,4aR,5R,6aS,7S)-1-(3,4-dihydroisoquinolin-2(1H)-ylmethylene)-7,11-dihydroxy-4-(methoxymethyl)-4a,6a-dimethyl-2,10-dioxo-1,2,4,4a,5,6,6a,7,8,9,9a,10-dodecahydroindeno[4,5-h]isochromen-5-yl acetate To a solution of 50 mg (0.12 mmol) 17-hydroxywortmannin in 0.5 mL $CH_2Cl_2$ is added 32 mg (0.24 mmol) 1,2,3,4-tetrahydroisoquinoline. The reaction mixture is stirred at room temperature overnight. $CH_2Cl_2$ is removed in vacuo. The residue is triturated with $Et_2O$ to give 9 mg (13.3%) product as an orange powder. MS (ESI) m/z 564.25 (M+1).

Example 13

Preparation of (1E,4S,4aR,5R,6aS,7S)-7,11-dihydroxy-4-(methoxymethyl)-4a,6a-dimethyl-2,10-dioxo-1-[(4-phenylpiperazin-1-yl)methylene]-1,2,4,4a,5,6,6a,7,8,9,9a,10-dodecahydroindeno[4,5-h]isochromen-5-yl acetate To a solution of 50 mg (0.12 mmol) 17-hydroxywortmannin in 0.5 mL $CH_2Cl_2$ is added 38.9 mg (0.24 mmol) 1-phenylpiperazine. The reaction mixture is stirred at room temperature overnight. $CH_2Cl_2$ is removed in vacuo. The residue is triturated with $Et_2O$ to give 16 mg (22.5%) product as an orange powder. MS (ESI) m/z 593.3 (M+1).

Example 14

Preparation of (1E,4S,4aR,5R,6aS,7S)-7,11-dihydroxy-4-(methoxymethyl)-4a,6a-dimethyl-1-[(4-methylpiperazin-1-yl)methylene]-2,10-dioxo-1,2,4,4a,5,6,6a,7,8,9,9a,10-dodecahydroindeno[4,5-h]isochromen-5-yl acetate To a solution of 50 mg (0.12 mmol) 17-hydroxywortmannin in 0.5 mL $CH_2Cl_2$ is added 24 mg (0.24 mmol) 1-methylpiperazine. The reaction mixture is stirred at room temperature overnight. $CH_2Cl_2$ is removed in vacuo. The residue is triturated with $Et_2O$ to give 19 mg (29.8%) product as an orange powder. MS (ESI) m/z 531.2 (M+1).

Example 15

Preparation of (1E,4S,4aR,5R,6aS,7S)-7,11-dihydroxy-4-(methoxymethyl)-4a,6a-dimethyl-2,10-dioxo-1-[(4-phenylpiperidin-1-yl)methylene]-1,2,4,4a,5,6,6a,7,8,9,9a,10-dodecahydroindeno[4,5-h]isochromen-5-yl acetate To a solution of 50 mg (0.12 mmol) 17-hydroxywortmannin in 0.5 mL $CH_2Cl_2$ is added 38.7 mg (0.24 mmol) 4-phenylpiperidine. The reaction mixture is stirred at room temperature overnight. $CH_2Cl_2$ is removed in vacuo. The residue is triturated with $Et_2O$ to give 14 mg (19.7%) product as an orange powder. MS (ESI) m/z 592.25 (M+1).

Example 16

Preparation of (1E,4S,4aR,5R,6aS,7S)-7-(formyloxy)-1-hydroxy-4-(methoxymethyl)-4a,6a-dimethyl-2,10-dioxo-1-(pyrrolidin-1-ylmethylene)-1,2,4,4a,5,6,6a,7,8,9,9a,10-dodecahydroindeno[4,5-h]isochromen-5-yl acetate 17-formylwortmannin (150 mg, 0.33 mmol) is dissolved in $CH_2Cl_2$ (1.5 mL) and is treated with 0.4 mmol of pyrrolidine for 30 min. Purification on silica gel eluting with $CH_2Cl_2$-MeOH (methylene chloride-methanol) (15:1) affords the product as a yellow-orange solid (yield is near quantitative). MS (El) analysis: 556 ($M^+$+1).

Example 17

Preparation of (1E,4S,4aR,5R,6aS,7S)-1-[(diallylamino)methylene]-7-(formyloxy)-11-hydroxy-4-(methoxymethyl)-4a,6a-dimethyl-2,10-dioxo-1,2,4,4a,5,6,6a,7,8,9,9a,10-dodecahydroindeno[4,5-h]isochromen-5-yl acetate 17-formylwortmannin (150 mg, 0.33 mmol) is dissolved in $CH_2Cl_2$ (1.5 mL) and is treated with 0.4 mmol of diallylamine for 30 min. Purification on silica gel eluting with $CH_2Cl_2$—MeOH (15:1) affords the product as a yellow-orange solid (yield is near quantitative). MS (EI) analysis: 530 ($M^+$+1).

Example 18

Preparation of (1E,4S,4aR,5R,6aS,7S)-1-[(diethylamino)methylene]-7-(formyloxy)-11-hydroxy-4-(methoxymethyl)-4a,6a-dimethyl-2,10-dioxo-1,2,4,4a,5,6,6a,7,8,9,9a,10-dodecahydroindeno[4,5-h]isochromen-5-yl acetate 17-formylwortmannin (150 mg, 0.33 mmol) is dissolved in $CH_2Cl_2$ (1.5 mL) and is treated with 0.4 mmol of diethylamine for 30 min. Purification on silica gel eluting with $CH_2Cl_2$—MeOH (15:1) affords the product as yellow-orange solids (yield is near quantitative). MS (EI): m/z 532 ($M^+$+1).

Example 19

Preparation of Acetic acid 4-{[bis-(2-hydroxy-ethyl)-amino]-methylene}-6,17-dihydroxy-1-methoxymethyl-10,13-dimethyl-3,7-dioxo-1,3,4,7,10,11,12,13,14,15,16,17-dodecahydro-2-oxa-cyclopenta[a]phenanthren-11-yl ester To a solution of 100 mg (0.23 mmol) 17-hydroxywortmannin in 2 mL $CH_2Cl_2$ is added diethanolamine (45 μL, 0.46 mmol). The reaction mixture is stirred at room temperature for 12 hours and then concentrated in vacuo. The residue is dissolved in EtOAc and precipitated with hexane. The precipitate is washed two times with hexane to give the product as a yellow solid. MS (ESI) m/z 537 (M+H).

Example 20

Preparation of Acetic acid 4-[(tert-butyl-methyl-amino)-methylene]-6,17-dihydroxy-1-methoxymethyl-10,13-dimethyl-3,7-dioxo-1,3,4,7,10,11,12,13,14,15,16,17-dodecahydro-2-oxa-cyclopenta[a]phenanthren-11-yl ester To a solution of 100 mg (0.23 mmol) 17-hydroxywortmannin in 2 mL $CH_2Cl_2$ is added N-tert-butylmethylamine (55 µL, 0.46 mmol). The reaction mixture is stirred at room temperature for 12 hours and then concentrated in vacuo. The residue is dissolved in EtOAc and precipitated with hexane. The precipitate is washed two times with hexane to give the product as a yellow solid. MS (ESI) m/z 519 (M+H).

Example 21

Preparation of Acetic acid 4-{[bis-(3-dimethylamino-propyl)-amino]-methylene}-6,17-dihydroxy-1-methoxymethyl-10,13-dimethyl-3,7-dioxo-1,3,4,7,10,11,12,13,14,15,16,17-dodecahydro-2-oxa-cyclopenta[a]phenanthren-11-yl ester To a solution of 100 mg (0.23 mmol) 17-hydroxywortmannin in 2 mL $CH_2Cl_2$ is added 3,3'-iminobis(N,N-dimethylpropylamine) (104 µL, 0.46 mmol). The reaction mixture is stirred at room temperature for 12 hours and then concentrated in vacuo. The residue is dissolved in EtOAc and precipitated with hexane. The precipitate is washed two times with hexane to give the product as a yellow solid. MS (ESI) m/z 619 (M+H).

Example 22

Preparation of 1-(11-Acetoxy-6,17-dihydroxy-1-methoxymethyl-10,13-dimethyl-3,7-dioxo-1,7,10,11,12,13,14,15,16,17-decahydro-2-oxa-cyclopenta[a]phenanthren-4-ylidenemethyl)-piperidine-4-carboxylic acid methyl ester To a solution of 100 mg (0.23 mmol) 17-hydroxywortmannin in 2 mL $CH_2Cl_2$ is added methyl isonipecotate (63 µL, 0.46 mmol). The reaction mixture is stirred at room temperature for 12 hours and then concentrated in vacuo. The residue is dissolved in EtOAc and precipitated with hexane. The precipitate is washed two times with hexane to give the product as a yellow solid. MS (ESI) m/z 575 (M+H).

Example 23

Preparation of 1-(11-Acetoxy-6,17-dihydroxy-1-methoxymethyl-10,13-dimethyl-3,7-dioxo-1,7,10,11,12,13,14,15,16,17-decahydro-2-oxa-cyclopenta[a]phenanthren-4-ylidenemethyl)-piperidine-4-carboxylic acid To a solution of 100 mg (0.23 mmol) 17-hydroxywortmannin and triethylamine (65 µL, 0.46 mmol) in 2 mL $CH_2Cl_2$ is added isonipecotic acid (60 mg, 0.46 mmol). The reaction mixture is stirred at room temperature for 12 hours and then concentrated in vacuo. The residue is dissolved in EtOAc and precipitated with hexane. The precipitate is washed two times with hexane to give the product as a yellow solid. MS (ESI) m/z 561 (M+H).

Example 24

Preparation of 4-[(11-Acetoxy-6,17-dihydroxy-1-methoxymethyl-10,13-dimethyl-3,7-dioxo-1,7,10,11,12,13,14,15,16,17-decahydro-2-oxa-cyclopenta[a]phenanthren-4-ylidenemethyl)-methyl-amino]-2,5-dimethyl-hex-2-enoic acid methyl ester To a solution of 100 mg (0.23 mmol) 17-hydroxywortmannin in 2 mL $CH_2Cl_2$ is added 2,5-dimethyl-4-methylamino-hex-2-enoic acid methyl ester (86 mg, 0.46 mmol). The reaction mixture is stirred at room temperature for 12 hours and then concentrated in vacuo. The residue is dissolved in EtOAc and precipitated with hexane. The precipitate is washed two times with hexane to give the product as a yellow solid. MS (ESI) m/z 630 (M+).

Example 25

Preparation of Acetic acid 6,17-dihydroxy-1-methoxymethyl-4-[({3-[4-(4-methoxy-phenyl)-piperazin-1-yl]-propyl}-methyl-amino)-methylene]-10,13-dimethyl-3,7-dioxo-1,3,4,7,10,11,12,13,14,15,16,17-dodecahydro-2-oxa-cyclopenta[a]phenanthren-11-yl ester To a solution of 100 mg (0.23 mmol) 17-hydroxywortmannin and triethylamine (65 µL, 0.46 mmol) in 2 mL $CH_2Cl_2$ is added {3-[4-(4-methoxy-phenyl)-piperazin-1-yl]-propyl}-methyl-amine hydrochloride (123 mg). The reaction mixture is stirred at room temperature for 12 hours and then concentrated in vacuo. The residue is dissolved in EtOAc and precipitated with hexane. The precipitate is washed two times with hexane to give the product as a yellow solid. MS (ESI) m/z 695 (M+H).

Example 26

Preparation of Acetic acid 6,17-dihydroxy-1-methoxymethyl-10,13-dimethyl-4-({methyl-[3-(4-methyl-piperazin-1-yl)-propyl]-amino}-methylene)-3,7-dioxo-1,3,4,7,10,11,12,13,14,15,16,17-dodecahydro-2-oxa-cyclopenta[a]phenanthren-11-yl ester To a solution of 100 mg (0.23 mmol) 17-hydroxywortmannin in 2 mL $CH_2Cl_2$ is added methyl-[3-(4-methyl-piperazine-1-yl)propyl]amine (80 mg, 0.46 mmol). The reaction mixture is stirred at room temperature for 12 hours and then concentrated in vacuo. The residue is dissolved in EtOAc and precipitated with hexane. The precipitate is washed two times with hexane to give the product as a yellow solid. MS (ESI) m/z 603 (M+H).

Example 27

Preparation of Acetic acid 6,17-dihydroxy-1-methoxymethyl-10,13-dimethyl-4-{[methyl-(3-morpholin-4-yl-propyl)-amino]-methylene}-3,7-dioxo-1,3,4,7,10,11,12,13,14,15,16,17-dodecahydro-2-oxa-cyclopenta[a]phenanthren-11-yl ester To a solution of 100 mg (0.23 mmol) 17-hydroxywortmannin in 2 mL $CH_2Cl_2$ is added methyl-(3-morpholin-4-yl-propyl)amine (74 mg, 0.46 mmol). The reaction mixture is stirred at room temperature for 12 hours and then concentrated in vacuo. The residue is dissolved in EtOAc and precipitated with hexane. The precipitate is washed two times with hexane to give the product as a yellow solid. MS (ESI) m/z 590 (M+H).

Example 28

Preparation of Acetic acid 4-{[(2-benzenesulfonyl-ethyl)-(3-diethylamino-propyl)-amino]-methylene}-6,17-dihydroxy-1-methoxymethyl-10,13-dimethyl-3,7-dioxo-1,3,4,7,10,11,12,13,14,15,16,17-dodecahydro-2-oxa-cyclopenta[a]phenanthren-11-yl ester To a solution of 100 mg (0.23 mmol) 17-hydroxywortmannin in 2 mL $CH_2Cl_2$ is added N'-(2-benzenesulfonyl-ethyl)-N,N-diethyl-propane-1,3-diamine (139 mg, 0.46 mmol). The reaction mixture is stirred at room temperature for 12 hours and then concentrated in vacuo. The residue is dissolved in EtOAc and precipitated with hexane. The precipitate is washed two times with hexane to give the product as a yellow solid. MS (ESI) m/z 730 (M+H).

Example 29

Preparation of Acetic acid 4-{[(1-aza-bicyclo[3.3.1]non-5-ylmethyl)-benzyl-amino]-methylene}-6,17-dihydroxy-1-methoxymethyl-10,13-dimethyl-3,7-dioxo-1,3,4,7,10,11,12,13,14,15,16,17-dodecahydro-2-oxa-cyclopenta[a]phenanthren-11-yl ester To a solution of 100 mg (0.23 mmol) 17-hydroxywortmannin and triethylamine (65 µL, 0.46 mmol) in 2 mL $CH_2Cl_2$ is added (1-aza-bicyclo[3.3.1]non-5-ylmethyl)-benzyl-amine hydrochloride (114 mg). The reaction mixture is stirred at room temperature for 12 hours and then concentrated in vacuo. The residue is dissolved in EtOAc and precipitated with hexane. The precipitate is washed two times with hexane to give the product as a yellow solid. MS (ESI) m/z 676 (M+H).

Example 30

Preparation of Acetic acid 6,17-dihydroxy-1-methoxymethyl-10,13-dimethyl-4-[4-(3-morpholin-4-yl-propyl)-piperazin-1-ylmethylene]-3,7-dioxo-1,3,4,7,10,11,12,13,14,15,16,17-dodecahydro-2-oxa-cyclopenta[a]phenanthren-11-yl ester To a solution of 100 mg (0.23 mmol) 17-hydroxywortmannin in 2 mL $CH_2Cl_2$ is added 1-(3-morpholinopropyl)piperazine (99 mg, 0.46 mmol). The reaction mixture is stirred at room temperature for 12 hours and then concentrated in vacuo. The residue is dissolved in EtOAc and precipitated with hexane. The precipitate is washed two times with hexane to give the product as a yellow solid. MS (ESI) m/z 645 (M+H).

Example 31

Preparation of Acetic acid 4-{[(2-dimethylamino-ethyl)-methyl-amino]-methylene}-6,17-dihydroxy-1-methoxymethyl-10,13-dimethyl-3,7-dioxo-1,3,4,7,10,11,12,13,14,15,16,17-dodecahydro-2-oxa-cyclopenta[a]phenanthren-11-yl ester To a solution of 100 mg (0.23 mmol) 17-hydroxywortmannin in 2 mL $CH_2Cl_2$ is added N,N,N'-trimethylethylenediamine (47 mg, 0.46 mmol). The reaction mixture is stirred at room temperature for 12 hours and then concentrated in vacuo. The residue is dissolved in EtOAc and precipitated with hexane. The precipitate is washed two times with hexane to give the product as a yellow solid. MS (ESI) m/z 534 (M+H).

Example 32

Preparation of Acetic acid 4-[4-(3-dimethylamino-propyl)-piperazin-1-ylmethylene]-6,17-dihydroxy-1-methoxymethyl-10,13-dimethyl-3,7-dioxo-1,3,4,7,10,11,12,13,14,15,16,17-dodecahydro-2-oxa-cyclopenta[a]phenanthren-11-yl ester To a solution of 100 mg (0.23 mmol) 17-hydroxywortmannin in 2 mL $CH_2Cl_2$ is added 1-(3-dimethylaminopropyl)piperazine (80 mg, 0.46 mmol). The reaction mixture is stirred at room temperature for 12 hours and then concentrated in vacuo. The residue is dissolved in EtOAc and precipitated with hexane. The precipitate is washed two times with hexane to give the product as a yellow solid. MS (ESI) m/z 603 (M+H).

Example 33

Preparation of Acetic acid 6,17-dihydroxy-1-methoxymethyl-10,13-dimethyl-4-[4-(2-morpholin-4-yl-ethyl)-piperazin-1-ylmethylene]-3,7-dioxo-1,3,4,7,10,11,12,13,14,15,16,17-dodecahydro-2-oxa-cyclopenta[a]phenanthren-11-yl ester To a solution of 100 mg (0.23 mmol) 17-hydroxywortmannin in 2 mL $CH_2Cl_2$ is added 1-(2-morpholinoethyl)piperazine (93 mg, 0.46 mmol). The reaction mixture is stirred at room temperature for 12 hours and then concentrated in vacuo. The residue is dissolved in EtOAc and precipitated with hexane. The precipitate is washed two times with hexane to give the product as a yellow solid. MS (ESI) m/z 631 (M+H).

Example 34

Preparation of Acetic acid 6,17-dihydroxy-1-methoxymethyl-10,13-dimethyl-4-[4-(1-methyl-piperidin-4-yl)-piperazin-1-ylmethylene]-3,7-dioxo-1,3,4,7,10,11,12,13,14,15,16,17-dodecahydro-2-oxa-cyclopenta[a]phenanthren-11-yl ester To a solution of 100 mg (0.23 mmol) 17-hydroxywortmannin in 2 mL $CH_2Cl_2$ is added 1-(1-methylpiperidin-4-yl)piperazine (85 mg, 0.46 mmol). The reaction mixture is stirred at room temperature for 12 hours and then concentrated in vacuo. The residue is dissolved in EtOAc and precipitated with hexane. The precipitate is washed two times with hexane to give the product as a yellow solid. MS (ESI) m/z 615 (M+H).

Example 35

Preparation of [(11-Acetoxy-6,17-dihydroxy-1-methoxymethyl-10,13-dimethyl-3,7-dioxo-1,7,10,11,12,13,14,15,16,17-decahydro-2-oxa-cyclopenta[a]phenanthren-4-ylidenemethyl)-methyl-amino]-acetic acid tert-butyl ester To a solution of 100 mg (0.23 mmol) 17-hydroxywortmannin and triethylamine (65 µL, 0.46 mmol) in 2 mL $CH_2Cl_2$ is added sarcosine tert butyl ester hydrochloride (84 mg, 0.46 mmol). The reaction mixture is stirred at room temperature for 12 hours and then concentrated in vacuo. The residue is dissolved in EtOAc and precipitated with hexane. The precipitate is washed two times with hexane to give the product as a yellow solid. MS (ESI) m/z 577 (M+H).

Example 36

Preparation of Acetic acid 4-{[(2,3-dihydroxy-propyl)-methyl-amino]-methylene}-6,17-dihydroxy-1-methoxymethyl-10,13-dimethyl-3,7-dioxo-1,3,4,7,10,11,12,13,14,15,16,17-dodecahydro-2-oxa-cyclopenta[a]phenanthren-11-yl ester To a solution of 100 mg (0.23 mmol) 17-hydroxywortmannin and triethylamine (65 µL, 0.46 mmol) in 2 mL CH$_2$Cl$_2$ is added 3-methylamino-1,2-propanediol hydrochloride (49 mg, 0.46 mmol). The reaction mixture is stirred at room temperature for 12 hours and then concentrated in vacuo. The residue is dissolved in EtOAc and precipitated with hexane. The precipitate is washed two times with hexane to give the product as a yellow solid. MS (ESI) m/z 537 (M+H).

Example 37

Preparation of 4-[(11-Acetoxy-6,17-dihydroxy-1-methoxymethyl-10,13-dimethyl-3,7-dioxo-1,7,10,11,12,13,14,15,16,17-decahydro-2-oxa-cyclopenta[a]phenanthren-4-ylidenemethyl)-methyl-amino]-butyric acid To a solution of 100 mg (0.23 mmol) 17-hydroxywortmannin and triethylamine (65 µL, 0.46 mmol) in 2 mL CH$_2$Cl$_2$ is added 4-(methylamino)butyric acid hydrochloride (71 mg, 0.46 mmol). The reaction mixture is stirred at room temperature for 12 hours and then concentrated in vacuo. The residue is dissolved in EtOAc and precipitated with hexane. The precipitate is washed two times with hexane to give the product as a yellow solid. MS (ESI) m/z 549 (M+H).

Example 38

Preparation of 1-(11-Acetoxy-6,17-dihydroxy-1-methoxymethyl-10,13-dimethyl-3,7-dioxo-1,7,10,11,12,13,14,15,16,17-decahydro-2-oxa-cyclopenta[a]phenanthren-4-ylidenemethyl)-azetidine-2-carboxylic acid To a solution of 100 mg (0.23 mmol) 17-hydroxywortmannin and triethylamine (65 µL, 0.46 mmol) in 2 mL CH$_2$Cl$_2$ is added L-azetidine-2-carboxylic acid (47 mg, 0.46 mmol). The reaction mixture is stirred at room temperature for 12 hours and then concentrated in vacuo. The residue is dissolved in EtOAc and precipitated with hexane. The precipitate is washed two times with hexane to give the product as a yellow solid. MS (ESI) m/z 533 (M+H).

Example 39

Preparation of 1-(11-Acetoxy-6,17-dihydroxy-1-methoxymethyl-10,13-dimethyl-3,7-dioxo-1,7,10,11,12,13,14,15,16,17-decahydro-2-oxa-cyclopenta[a]phenanthren-4-ylidenemethyl)-pyrrolidine-2-carboxylic acid methyl ester To a solution of 100 mg (0.23 mmol) 17-hydroxywortmannin in 2 mL CH$_2$Cl$_2$ is added L-proline methyl ester (60 mg, 0.46 mmol). The reaction mixture is stirred at room temperature for 12 hours and then concentrated in vacuo. The residue is dissolved in EtOAc and precipitated with hexane. The precipitate is washed two times with hexane to give the product as a yellow solid. MS (ESI) m/z 561 (M+H).

Example 40

Preparation of Acetic acid 4-{[benzyl-(2-cyano-ethyl)-amino]-methylene}-6,17-dihydroxy-1-methoxymethyl-10,13-dimethyl-3,7-dioxo-1,3,4,7,10,11,12,13,14,15,16,17-dodecahydro-2-oxa-cyclopenta[a]phenanthren-11-yl ester To a solution of 100 mg (0.23 mmol) 17-hydroxywortmannin in 2 mL CH$_2$Cl$_2$ is added 3-benzylamino-propionitrile (73 µL, 0.46 mmol). The reaction mixture is stirred at room temperature for 12 hours and then concentrated in vacuo. The residue is dissolved in EtOAc and precipitated with hexane. The precipitate is washed two times with hexane to give the product as a yellow solid. MS (ESI) m/z 592 (M+H).

Example 41

Preparation of Acetic acid 4-{[(2-diethylamino-ethyl)-methyl-amino]-methylene}-6,17-dihydroxy-1-methoxymethyl-10,13-dimethyl-3,7-dioxo-1,3,4,7,10,11,12,13,14,15,16,17-dodecahydro-2-oxa-cyclopenta[a]phenanthren-11-yl ester To a solution of 100 mg (0.23 mmol) 17-hydroxywortmannin in 2 mL CH$_2$Cl$_2$ is added N,N-Diethyl-N'-methyl-ethane-1,2-diamine (45 µL, 0.28 mmol). The reaction mixture is stirred at room temperature for 12 hours and then concentrated in vacuo. The residue is dissolved in EtOAc and precipitated with hexane. The precipitate is washed two times with hexane to give the product as a yellow solid. MS (ESI) m/z 561 (M+H).

Example 42

Preparation of Acetic acid 4-{[(2-diethylamino-ethyl)-ethyl-amino]-methylene}-6,17-dihydroxy-1-methoxymethyl-10,13-dimethyl-3,7-dioxo-1,3,4,7,10,11,12,13,14,15,16,17-dodecahydro-2-oxa-cyclopenta[a]phenanthren-11-yl ester To a solution of 100 mg (0.23 mmol) 17-hydroxywortmannin in 2 mL CH$_2$Cl$_2$ is added N,N-Diethyl-N'-ethyl-ethane-1,2-diamine (50 µL). The reaction mixture is stirred at room temperature for 12 hours and then concentrated in vacuo. The residue is dissolved in EtOAc and precipitated with hexane. The precipitate is washed two times with hexane to give the product as a yellow solid. MS (ESI) m/z 575 (M+H).

Example 43

Preparation of Acetic acid 4-{[benzyl-(2-dimethylamino-ethyl)-amino]-methylene}-6,17-dihydroxy-1-methoxymethyl-10,13-dimethyl-3,7-dioxo-1,3,4,7,10,11,12,13,14,15,16,17-dodecahydro-2-oxa-cyclopenta[a]phenanthren-11-yl ester To a solution of 100 mg (0.23 mmol) 17-hydroxywortmannin in 2 mL CH$_2$Cl$_2$ is added N,N-Dimethyl-N'-benzyl-ethane-1,2-diamine (62 µL). The reaction mixture is stirred at room temperature for 12 hours and then concentrated in vacuo. The residue is dissolved in EtOAc and precipitated with hexane. The precipitate is washed two times with hexane to give the product as a yellow solid. MS (ESI) m/z 609 (M+H).

Example 44

Preparation of Acetic acid 6,17-dihydroxy-1-methoxymethyl-10,13-dimethyl-3,7-dioxo-4-(4-oxo-piperidin-1-ylmethylene)-1,3,4,7,10,11,12,13,14,15,16,17-dodecahydro-2-oxa-cyclopenta[a]phenanthren-11-yl ester To a 17-OH wortmannin solution {25 mg in 2 ml THF/H$_2$O (4:1), 0.058 mmol), 16 mg of potassium carbonate (0.116 mmol) and 9.5 mg (0.06 mmol) of 4-piperidone monohydrate hydrochloride (98% purity) are added. This reaction solution is stirred at room temperature under nitrogen atmosphere. After 1 hr, the solution is poured into 10 ml methylene chloride and the organic layer is separated and washed with brine (3 ml). After solvents are evaporated under vacuum, the residual solid is dissolved in 4 ml ethyl acetate and ~2 ml hexane is added to give a precipitate. After filtration, the solid is washed with 2 ml hexane, and dried under vacuum to give 22 mg of the title compound as an orange powder (1). UV λmax (CH$_3$CN/H$_2$O): 250 nm, 320 nm, 397 nm; Positive ESI-MS: m/z 563 [M+Na]$^+$, 530 [M+H]$^+$.

Example 45

Preparation of 4-{[(2-Dimethylamino-ethyl)-ethylamino]-methylene}-6,17-dihydroxy-1-methoxymethyl-10,13-dimethyl-10,11,12,13,14,15,16,17-octahydro-1H,4H-2-oxa-cyclopenta[a]phenanthrene-3,7-dione 11-Deacetoxy-17-OH-wortmannin (20 mg, 0.053 mmol) is dissolved in 2 ml methylene chloride and stirred at room temperature under nitrogen atmosphere as N,N-dimethyl-N'-ethyl-ethylenediamine (0.053 mmol, 8.4 µl) is added. The reaction turns orange immediately. After 30 min, the solvent is evaporated and the solid is recrystallized from ethyl acetate/hexane (3:1). After filtration, the solid is washed with hexane and dried under vacuum to yield 18 mg of the title compound as an orange powder. UV λmax (CH$_3$CN/H$_2$O): 250 nm, 320 nm, 397 nm; Positive ESI-MS: m/z 489 [M+H]$^+$.

Example 46

Preparation of Acetic acid 4-{[(2-dimethylamino-ethyl)-ethyl-amino]-methylene}-6,17-dihydroxy-1-methoxymethyl-10,13-dimethyl-3,7-dioxo-1,3,4,7,10,11,12,13,14,15,16,17-dodecahydro-2-oxa-cyclopenta[a]phenanthren-11-yl ester 17-Hydroxywortmannin (129 mg, 0.3 mmol) is dissolved in 5 ml methylene chloride and stirred at room temperature under nitrogen atmosphere as N,N-dimethyl-N'-ethyl-ethylenediamine (0.31 mmol, 56 µl) is added. The reaction solution turns orange immediately. After 30 min, the solvent is evaporated and the solid is recrystallized from ethyl acetate/hexane (3:1). After filtration, the solid is washed with hexane and dried under vacuum to yield 115 mg of the title compound as an orange powder. UV λmax (CH$_3$CN/H$_2$O): 250 nm, 320 nm, 397 nm; Positive ESI-MS: m/z 547 [M+H]$^+$.

Example 47

Preparation of Acetic acid 4-[1,4']bipiperidinyl-1'-ylmethylene-6,17-dihydroxy-1-methoxymethyl-10,13-dimethyl-3,7-dioxo-1,3,4,7,10,11,12,13,14,15,16,17-dodecahydro-2-oxa-cyclopenta[a]phenanthren-11-yl ester 17-Hydroxywortmannin (30 mg, 0.069 mmol) is dissolved in 2 ml methylene chloride and stirred at room temperature under nitrogen atmosphere as 4-piperidinopiperidine (0.069 mmol, 11.6 mg) is added. The reaction solution turns orange immediately. After 30 min, the solvent is evaporated and the solid is recrystallized from ethyl acetate/hexane (2:1). After filtration, the solid is washed with hexane and dried under vacuum to yield about 30 mg the title compound as an orange powder. UV λmax (CH$_3$CN/H$_2$O): 250 nm, 320 nm, 397 nm; Positive ESI-MS: m/z 599 [M+H]$^+$.

Example 48

Preparation of Acetic acid 6,17-dihydroxy-1-methoxymethyl-10,13-dimethyl-4-morpholin-4-ylmethylene-3,7-dioxo-1,3,4,7,10,11,12,13,14,15,16,17-dodecahydro-2-oxa-cyclopenta[a]phenanthren-11-yl ester 17-Hydroxywortmannin (50 mg, 0.116 mmol) is dissolved in 2 ml methylene chloride and stirred at room temperature under nitrogen atmosphere as morpholine (0.12 mmol, 10 µl) is added. The reaction solution turns orange immediately. After 30 min, the solvent is evaporated and the solid is washed with hexane (2×3 ml) and dried under vacuum to yield 50 mg of the title compound as an orange powder. UV λmax (CH$_3$CN/H$_2$O): 250 nm, 320 nm, 397 nm; Positive ESI-MS: m/z 540 [M+Na]$^+$, 518 [M+H]$^+$.

Example 49

Preparation of Propionic acid 4-{[(2-dimethylamino-ethyl)-methyl-amino]-methylene}-6,17-dihydroxy-1-methoxymethyl-10,13-dimethyl-3,7-dioxo-1,3,4,7,10,11,12,13,14,15,16,17-dodecahydro-2-oxa-cyclopenta[a]phenanthren-11-yl ester To a solution of β-11-O-Desacetyl-11-O-propionyl-17-dihydrowortmannin (which can be prepared according to Creemer, L. C.; Kirst, H. A.; Vlahos, C. J.; Schultz, R. M. *J Med Chem.* 1996, 39, 5021-5024) (100 mg) in dichloromethane (4 mL) is added N,N,N-trimethylethylenediamine (32 µL). The reaction mixture is stirred at room temperature and then concentrated under reduced pressure. The residue is triturated with hexanes and ethyl acetate to give a hard orange foam (0.12 g, 100%). MS (ES$^+$): 547.2 (M+H)$^+$.

Example 50

Preparation of (1E,4S,4aR,5R,6aS,7S,9aR)-1-[(diethylamino)methylene]-5,7,11-trihydroxy-4-(methoxymethyl)-4a,6a-dimethyl-4a,5,6,6a,7,8,9,9a-octahydroindeno[4,5-h]isochromene-2,10(1H,4H)-dione To a solution of 17-hydroxywortmannin (1100 mg) in methanol (5 mL) is added diethylamine (0.72 mL). After 48 hours the reaction mixture is concentrated under vacuum. The residue is dissolved in EtOAc and precipitated with hexane. A yellow powder is obtained (0.29 mg). MS: 462.2 (M+H)$^+$.

Example 51

Preparation of (1Z,4S,4aR,5R,6aS,7S)-7,11-dihydroxy-4-(methoxymethyl)-4a,6a-dimethyl-2,10-dioxo-1-{12-oxo-16-[(3aR,4R,6aS)-2-oxohexahydro-1H-thieno[3,4-d]imidazol-4-yl]-5,8-dioxa-2,11-diazahexadec-1-ylidene}-1,2,4,4a,5,6,6a,7,8,9,9a,10-dodecahydroindeno[4,5-h]isochromen-5-yl acetate To a solution of 27.9 mg (0.0649 mmol) 17-hydroxywortmannin in 0.2 mL CHCl$_2$ and 0.2 mL CH$_3$CN is added 25.5 mg (0.0681 mmol) ((+)-biotinyl-3,6-dioxaoctanediamine. The reaction mixture is stirred at room temperature for 4 h. The reaction mixture is filtered and $CH_2Cl_2$ is removed in vacuo to give a yellow foam (19 mg, 36%). MS (ESI) m/z 805.8 (M+1).

Example 52

Preparation of Acetic acid 4-butylsulfanylmethylene-6,17-dihydroxy-1-methoxymethyl-10,13-dimethyl-3,7-dioxo-1,3,4,7,10,11,12,13,14,15,16,17-dodecahydro-2-oxa-cyclopenta[a]phenanthren-11-yl ester To a solution of 17-dihydrowortmannin (0.21 g, 0.49 mmol) in dichloromethane (2 mL) is added n-butanethiol (90 μL), followed by one drop of triethylamine. After stirring at room temperature for 19 hours, an additional drop of triethylamine is added. After stirring for three days, the reaction mixture is concentrated under reduced pressure. The residue is purified by flash chromatography (ethyl acetate/hexanes) to provide a yellow-orange solid (82 mg, 40%). MS (ES+): 521.1 $(M+H)^+$.

Example 53

Preparation of 7-Pegylated di-(1E,4S,4aR,5R,6aS,7S)-1-{[[3-(dimethylamino)propyl](methyl)amino]methylene}-7,11-dihydroxy-4-(methoxymethyl)-4a,6a-dimethyl-2,10-dioxo-1,2,4,4a,5,6,6a,7,8,9,9a,10-dodecahydroindeno[4,5-h]isochromen-5-yl acetate To a solution of bis 17-hydroxywortmanninPeg5000 (10 g, see FIG. 66, also described at pages 30 and 33 of prior application U.S. Ser. No. 10/828,474 filed Apr. 20, 2004, herein incorporated by reference) in 30 mL $CH_2Cl_2$ is added N,N,N'-trimethyl-1,3-propanediamine (0.98 mL, 6.68 mmol). The reaction mixture is stirred at room temperature for 24 hours and then concentrated in vacuo. The residue is treated with $Et_2O$. The resulting solid is collected by filtration and dried in vacuo to give a yellow solid (10.1 g). MS (ESI) m/z 6069 (M+) for $X=(CH_2OCH_2)_{107}$.

Example 54

Preparation of 7-Pegylated (1E,4S,4aR,5R,6aS,7S,9aR)-1-[(diethylamino)methylene]-7,11-dihydroxy-4-(methoxymethyl)-4a,6a-dimethyl-2,10-dioxo-1,2,4,4a,5,6,6a,7,8,9,9a,10-dodecahydroindeno[4,5-h]isochromen-5-yl acetate To a solution of 17-pegylated-17-hydroxywortmannin (3 g) in 12 mL $CH_2Cl_2$ is added 200 μL diethylamine. The reaction mixture is stirred at room temperature overnight. $CH_2Cl_2$ is removed in vacuo. The residue is triturated with $Et_2O$ to give 2.8 g of the product as a yellow powder.

Example 55

Preparation of the PEGylated Compound Pictured in FIG. 1

Step A:
To a solution of mPEG5000-$NH_2$ (purchased from Nektar, 3.0 g, 0.60 mmol) in dichloromethane (15 mL) is added di-t-butyldicarbonate (0.28 mL, 1.2 mmol), followed by triethylamine (0.4 mL). The mixture is stirred at room temperature and then concentrated under reduced pressure to give mPEG5000-NHBoc as a white solid (3.0 g).

Step B:
To a 0° C. solution of mPEG5000-NHBoc (0.60 mmol) in dimethylformamide (30 mL) is added iodomethane (0.4 mL), followed by sodium hydride (60% dispersion in mineral oil, 0.12 g). After an overnight stir at room temperature, the reaction mixture is quenched with water and evaporated to dryness under reduced pressure. The residue is purified by flash chromoatography to give mPEG5000-N($CH_3$)Boc as a pale yellow solid.

Step C:
To a solution of mPEG5000-N($CH_3$)Boc (2.4 g) in dichloromethane (100 mL) is added trifluoroacetic acid (2.5 mL). The reaction mixture is stirred overnight at room temperature and then concentrated under reduced pressure to give mPEG5000-NH$CH_3$ as a TFA (trifluoroacetic) salt.

Step D:
To a suspension of mPEG5000-NH$CH_3$, TFA salt (2.5 g, 0.5 mmol) in dichloromethane is added triethylamine (0.3 mL), followed by 17-hydroxywortmannin (0.13 g, 0.3 mmol). After stirring overnight, additional quantities of 17-hydroxywortmannin (0.12 g, 0.3 mmol) and triethylamine (5 drops) are added. After stirring at room temperature, the mixture is concentrated under reduced pressure and the resulting residue is purified by flash chromatography (methanol/chloroform) to give the 17-hydroxywortmannin, mPEG5000NH$CH_3$ adduct as golden flakes (2.0 g). MS: 5321.0.

Example 56

Preparation of (1Z,4S,4aR,5R,6aS,7S)-1-{[t-butylamino]methylene}-7,11-dihydroxy-4-(methoxymethyl)-4a,6a-dimethyl-2,10-dioxo-1,2,4,4a,5,6,6a,7,8,9,9a,10-dodecahydroindeno[4,5-h]isochromen-5-yl acetate To a solution of 100 mg (0.23 mmol) 17-hydroxywortmannin in 2 mL $CH_2Cl_2$ is added 49 μL (0.46 mmol) tertbutylamine. The reaction mixture is stirred at room temperature overnight. $CH_2Cl_2$ is removed in vacuo. The residue is triturated with $Et_2O$ to give 58 mg (50%) product as an orange powder. MS (ESI) m/z 504 (M+1).

Example 57

Preparation of (1Z,4S,4aR,5R,6aS,7S)-1-{[3-dimethylamino-propylamino]methylene}-7,11-dihydroxy-4-(methoxymethyl)-4a,6a-dimethyl-2,10-dioxo-1,2,4,4a,5,6,6a,7,8,9,9a,10-dodecahydroindeno[4,5-h]isochromen-5-yl acetate To a solution of 100 mg (0.23 mmol) 17-hydroxywortmannin in 2 mL $CH_2Cl_2$ is added 58 μL (0.46 mmol) N,N-dimethyl-1,3-propanediamine. The reaction mixture is stirred at room temperature overnight. $CH_2Cl_2$ is removed in vacuo. The residue is triturated with $Et_2O$ to give 74 mg (60%) product as an orange powder. MS (ESI) m/z 533 (M+1).

Example 58

Preparation of (1Z,4S,4aR,5R,6aS,7S)-7,11-dihydroxy-1-{[(2-mercaptoethyl)amino]methylene}-4-(methoxymethyl)-4a,6a-dimethyl-2,10-dioxo-1,2,4,4a,5,6,6a,7,8,9,9a,10-dodecahydroindeno[4,5-h]isochromen-5-yl acetate To a solution of 100 mg (0.23 mmol) 17-hydroxywortmannin in 2 mL $CH_2Cl_2$ is added 32 mg (0.278 mmol) 2-aminoethanethiol hydrochloride and triethylamine (45 μL, 0.325 mmol). The reaction mixture is stirred at room temperature for 4 h. Water is added and the $CH_2Cl_2$ is removed, filtered through a plug of Kimwipe tissue and concentrated in vacuo to give a yellow foam. MS (ESI) m/z 508.5 (M+1).

Example 59

Preparation of (1Z,4S,4aR,5R,6aS,7S,9aR)-1-[(ethylamino)methylene]-7,11-dihydroxy-4-(methoxymethyl)-4a,6a-dimethyl-2,10-dioxo-1,2,4,4a,5,6,6a,7,8,9,9a,10-dodecahydroindeno[4,5-h]isochromen-5-yl acetate To a solution of 100 mg (0.23 mmol) 17-hydroxywortmannin in 2 mL $CH_2Cl_2$ is added 100 mg of ethylamine hydrochloride and 100 μL triethylamine. The reaction mixture is stirred at room temperature for 24 h. Water is added and the $CH_2Cl_2$ is removed, filtered through $K_2CO_3$ and concentrated in vacuo. The residue is dissolved in EtOAc and precipitated with hexanes to give a yellow powder (32 mg, 29%). MS (ESI) m/z 476.22813 (M+1).

Example 60

Preparation of (1E,4S,4aR,5R,6aS,7S)-1-{[[3-(dimethylamino)propyl](methyl)amino]methylene}-5,7,11-trihydroxy-4-(methoxymethyl)-4a,6a-dimethyl-4a,5,6,6a,7,8,9,9a-octahydroindeno[4,5-h]isochromene-2,10(1H,4H)-dione To a solution of 50 mg (0.13 mmol) 11-desacetyl-17-hydroxywortmannin in 2 mL $CH_2Cl_2$ is added 38 μL of N,N,N'-trimethylpropanediamine (0.26 mmol). The reaction mixture is stirred at room temperature for 24 h. The $CH_2Cl_2$ is removed in vacuo. The residue is dissolved in EtOAc and precipitated with hexanes to give a yellow powder (35 mg, 53%). MS (ESI) m/z 505.29083 (M+1).

Example 61

Preparation of (1Z,4S,4aR,5R,6aS,7S,9aR)-7,11-dihydroxy-1-(hydroxymethylene)-4-(methoxymethyl)-4a,6a-dimethyl-2,10-dioxo-1,2,4,4a,5,6,6a,7,8,9,9a,10-dodecahydroindeno[4,5-h]isochromen-5-yl acetate 17-hydroxy-wortmannin (20 mg, 0.047 mmol) is dissolved in 4 mL acetonitrile and 2 mL water with 0.5 mL triethylamine. The reaction mixture is stirred at room temperature overnight. The title compound is isolated by preparative HPLC using Nova-Pak HRC 18, 60A, 6 um, 19×300 mm column (Waters) at UV 254 nm (Mobile Phase A is 100 ml acetonitrile with 900 ml water, and 0.2 ml trifluoroacetic acid. Mobile Phase B is 900 ml acetonitrile with 100 ml water and 0.2 ml trifluoroacetic acid. The gradient is 0-5 min at 20% B and 80% A, 5-35 min from 20% B to 70% B at flow rate 20 mL/min). The fraction at 12 min peak is collected and extracted with $CH_2Cl_2$. The organic layer is dried over anhydrous sodium sulfate and rotavaped to dryness. A total of 5 mg of yellow solid is obtained by precipitation from 1 mL $CH_2Cl_2$ and 3 mL heptane and drying using nitrogen gas and then a speecdvac. LC/MS shows [M+H] 449.31 and [M−H] 447.26.

Example 62

Preparation of (1E,4S,4aR,5R,6aS,7S,9aR)-1-({tert-butyl[2-(dimethylamino)ethyl]amino}methylene)-7,11-dihydroxy-4-(methoxymethyl)-4a,6a-dimethyl-2,10-dioxo-1,2,4,4α,5,6,6α,7,8,9,9α,10-dodecahydroindeno[4,5-h]isochrom en-5-yl acetate Step A:
A solution of t-butylethanolamine (12 g, 100 mmol) in chloroform (100 mL) is cooled to −10° C. in a sodium chloride/ice bath. Following the addition of thionyl chloride (10 mL in 10 mL chloroform), the cooling bath is removed and replaced with an oil bath. The reaction mixture is heated at reflux for six hours and then allowed to cool to room temperature. The precipitated material is collected and washed with acetone to give 2-(t-butylamino)ethylchloride hydrochloride as a white solid.

MS (ES$^+$): m/z (M+H)=136.2, 138.2.

Step B:
2-(t-Butylamino)ethylchloride hydrochloride (1.2 g, 7.0 mmol) is dissolved in aqueous dimethylamine solution (40% by weight, 22 mL) in a sealed tube. The mixture is heated in a 140° C. oil bath for six hours, allowed to cool to room temperature, and then is saturated with solid potassium carbonate. The mixture is extracted thrice with ethyl acetate. The combined extracts are dried over anhydrous sodium sulfate, decanted, and concentrated under reduced pressure to give N-t-butyl,N',N'-dimethylethylenediamine as a light brown liquid (0.57 g, 56%). The crude material is carried on to the following step without further purification.

MS (ES$^+$): m/z (M+H)=145.3.

Step C:
To a solution of crude N-t-butyl,N',N'-dimethylethylenediamine (0.57 g, 4.0 mmol) in dichloromethane (20 mL) is added dropwise benzylchloroformate (0.85 mL, 6.0 mmol) at room temperature. The reaction mixture is stirred overnight at room temperature. Following an aqueous work-up, the crude product is purified by semi-preparative reverse-phase HPLC (employing a gradient elution of 5% acetonitrile/95% water/0.1% trifluoroacetic acid to 100% acetonitrile over 40 minutes) to give N-benzyloxycarbonyl-N-t-butyl,N'N'-dimethylethylenediamine trifluoroacetic acid as a clear, colorless oil (0.47 g, 29%). MS (ES+): m/z (M+H)=279.15.

Step D:
A solution of N-benzyloxycarbonyl-N-t-butyl,N',N'-dimethylethylenediamine trifluroacetic acid (0.47 g, 1.2 mmol) in ethanol (15 mL) is degassed with dry ice. Palladium on carbon (10%, 100 mg) is added, followed by concentrated hydrochloric acid (300 μL). The mixture is shaken on a Parr hydrogenator at 50 psi hydrogen for 20 hours, filtered through a pad of diatomaceous earth, and concentrated under reduced pressure to give N-t-butyl,N',N'-dimethylethylenediamine dihydrochloride as a white powder (0.22 g, 85%).

MS (ES$^+$): m/z (M+H)=145.3.

Step E:
To a suspension of N-t-butyl,N',N'-dimethylethylenediamine dihydrochloride (0.12 g, 0.55 mmol) in dichloromethane (5 mL) is added triethylamine (220 μL, 1.7 mmol). 17-Hydroxywortmannin (0.12 g, 0.28 mmol) is added and the reaction mixture is stirred overnight at room temperature and then concentrated under reduced pressure. The residue is dissolved in DMSO/acetonitrile/water (1:1:0.5) and purified by semi-preparative reverse-phase HPLC (employing a gradient elution of 5% acetonitrile/95% water to 100% acetonitrile over 40 minutes). The collected material is triturated with ethyl acetate and collected by filtration to give (1E,4S,4α,5R,6αS,7S,9αR)-1-({tert-butyl[2-(dimethylamino)ethyl]amino}methylene)-7,11-dihydroxy-4-(methoxymethyl)-4α,6α-dimethyl-2,10-dioxo-1,2,4,4α,5,6,6α,7,8,9,9α,10-dodecahydroindeno[4,5-h]isochrom en-5-yl acetate as a pale yellow powder. HRMS (ES$^+$): m/z (M+H)=575.33233.

Example 63

Preparation of: Butanoic acid 4-{[(2-dimethylaminopropyl)-methyl-amino]-methylene}-6,17-dihydroxy-1-methoxymethyl-10,13-dimethyl-3,7-dioxo-1,3,4,7,10,11,12,13,14,15,16,17-dodecahydro-2-oxa-cyclopenta[a]phenanthren-11-yl ester In a manner analogous to that described in example 48, β-11-O-desacetyl-11-O-butanoyl-17-dihydrowortmannin (80 mg, 0.17 mmol) in dichloromethane (2 mL) was treated with N,N,N-trimethylpropylenediamine (58 μL). The reaction mixture was stirred overnight at room temperature and then concentrated under reduced pressure. The residue was purified by reverse-phase HPLC (employing a gradient elution of 5% acetonitrile/95% water to 95% acetonitrile over 40 minutes) to give the title compound as a hard, orange foam (47 mg, 48%). MS (ES$^+$): m/z (M+H)=575.4

Example 64

Preparation of Acetic acid 4-{[(2-dimethylamino-propyl)-ethyl-amino]-methylene}-6,17-dihydroxy-1-methoxymethyl-10,13-dimethyl-3,7-dioxo-1,3,4,7,10,11,12,13,14,15,16,17-dodecahydro-2-oxa-cyclopenta[a]phenanthren-11-yl ester N,N-dimethylaminopropyl chloride hydrochloride (1.6 g, 10 mmol) was added to ethylamine (70% by weight aqueous solution, 24 mL, 300 mmol) in a sealed vessel. The suspension was heated in an oil bath at 140° C. for 8 hours. After cooling to room temperature, the mixture was saturated with solid potassium carbonate and extracted thrice with ethyl acetate. The combined extracts were washed once with saturated aqueous sodium chloride solution, dried over anhydrous magnesium sulfate, filtered, and concentrated under reduced pressure to give the crude N-ethyl-N,N-dimethylpropane-1,3-diamine (500 mg, 38%). MS (ES$^+$): m/z (M+H)=131.3 A solution of the crude N'-ethyl-N,N-dimethylpropane-1,3-diamine (0.50 g, 3.8 mmol) in dichloromethane (20 mL) was treated with benzylchloroformate (0.82 mL, 5.7 mmol) and then was allowed to stir at room temperature for two hours. After concentrating the reaction mixture under reduced pressure, the residue was purified by reverse-phase HPLC (employing a gradient elution of 5% acetonitrile/95% water/0.1% trifluoroacetic acid to 95% acetonitrile over 45 minutes) to give (3-dimethylaminopropyl)-ethyl-carbamic acid benzyl ester trifluoroacetate (840 mg, 58%) as a clear, colorless syrup MS (ES$^+$): m/z (M+H)=265.4

To a solution of the (3-dimethylaminopropyl)-ethyl-carbamic acid benzyl ester trifluoroacetate (0.84 g, 2.2 mmol) in ethanol (30 mL) and concentrated hydrochloric acid (0.5 mL, 6 mmol) was added palladium on carbon (10%, 50 mg). The suspension was shaken under 50 psi hydrogen. When the consumption of hydrogen was observed to have ceased, the mixture was filtered through a pad of diatomaceous earth and then concentrated under reduced pressure to give N'-ethyl-N,N-dimethylpropane-1,3-diamine dihydrochloride (400 mg, 89%) as a white solid. MS (ES$^+$): m/z (M+H)=131.3 To a suspension of the N'-ethyl-N,N-dimethylpropane-1,3-diamine dihydrochloride (0.26 g, 1.3 mmol) in dichloromethane (5 mL) was added triethylamine (0.51 mL, 3.9 mmol). After stirring for 10 minutes, the mixture was treated with 17-hydroxywortmannin (0.28 g, 0.65 mmol). After stirring overnight at room temperature, the mixture was concentrated under reduced pressure and then purified by reverse-phase HPLC (employing a gradient elution of 5% acetonitrile/95% water to 95% acetonitrile over 45 minutes). The title compound was obtained as a rust-colored solid (11.6 mg). MS (ES$^+$): m/z (M+H)=561.4.

Example 65

Preparation of (1E,4S,4aR,5R,6aS,7S,9aR)-1-({4-[2-(2,5-dioxo-2,5-dihydro-1H-pyrrol-1-yl)ethyl]piperazin-1-yl}methylene)-7,11-dihydroxy-4-(methoxymethyl)-4a,6a-dimethyl-2,10-dioxo-1,2,4,4a,5,6,6a,7,8,9,9a,10-dodecahydroindeno[4,5-h]isochromen-5-yl acetate To a solution of (3-dimethylaminopropyl)-ethyl-carbamic acid benzyl ester trifluoroacetate (0.84 g, 2.2 mmol) in ethanol (30 mL) and concentrated hydrochloric acid (0.5 mL, 6 mmol) was added palladium on carbon (10%, 50 mg). The suspension was shaken under 50 psi hydrogen. When the consumption of hydrogen was observed to have ceased, the mixture was filtered through a pad of diatomaceous earth and then concentrated under reduced pressure to give N'-ethyl-N,N-dimethylpropane-1,3-diamine dihydrochloride (400 mg, 89%) as a white solid. MS (ES$^+$): m/z (M+H)=131.3 to a suspension of the N'-ethyl-N,N-dimethylpropane-1,3-diamine dihydrochloride (0.26 g, 1.3 mmol) in dichloromethane (5 mL) was added triethylamine (0.51 mL, 3.9 mmol). After stirring for 10 minutes, the mixture was treated with 17-hydroxywortmannin (0.28 g, 0.65 mmol). After stirring overnight at room temperature, the mixture was concentrated under reduced pressure and then purified by reverse-phase HPLC (employing a gradient elution of 5% acetonitrile/95% water to 95% acetonitrile over 45 minutes). The title compound was obtained as a rust-colored solid (11.6 mg). MS(ES$^+$): m/z (M+H)=561.4.

Example 66

Fluorescence Polarization Assay for PI3K

This assay is used to determine the IC50 of compounds of the present invention as it identifies inhibitors of PI3 kinase by measuring inhibition.

Materials

Reaction Buffer: 20 mM Hepes, pH 7.5, 2 mM MgCl$_2$, 0.05% CHAPS, and 0.01% BME (added fresh)

Stop/Detection Buffer: 100 mM Hepes, pH 7.5, 4 mM EDTA, 0.05% CHAPS

ATP 20 mM in water

PIP2 (diC8, cat# P-4508) 1 mM in water (MW=856.5)

GST-GRP 1.75 mg/mL or 1.4 mg/mL in 10% glycerol

Red detector (TAMRA) 2.5 μM

Plate: Nunc 384 well black polypropylene fluorescence plate

Methods

The assay is run by placing 5 μL of diluted enzyme per well, then 5 μL of diluted compound (or 9.5 μL enzyme then 0.5 μL compound in DMSO) is added and mixed. Then, 10 μL substrate is added to start the reaction. The samples are incubated 30-60 minutes, then the reaction is stopped by adding 20 μL stop/detector mix.

PI3K is diluted with reaction buffer (e.g., 5 μL or 7.5 μL PI3K into 620 μL reaction buffer), and 5 μL of diluted enzyme is used per well. 5 μL reaction buffer or drug diluted in buffer (e.g., 4 μL/100 so final DMSO is 1% in reaction) is added to each. The samples are mixed by pipetting up and down. Alternatively, the enzyme can be diluted to 1215 μL. In this case 9.8 μL is added per well and 0.2 μL compound is added in DMSO.

To prepare 1 mL of substrate solution, 955 μL reaction buffer, 40 μL PIP2, and 2.5 μL ATP are mixed. 10 μL of substrate is added to each well to start the reaction. This results in 20 μM PIP2, and 25 μM ATP per reaction.

Stop/detector mix is prepared by mixing 4 μL Red detector and 1.6 μL or 2.0 μL GST-GRP with 1 mL Stop buffer, which results in 10 nM probe and 70 nM GST-GRP). 20 μL of the stop/detector mix is added to each well to stop the reaction. The plates are read after 30-90 minutes keeping the red probe solutions dark.

For the zero time point, stop/detector mix is added to the enzyme just before adding substrate. For an extra control, stop/detector mix is added to buffer (no enzyme) and substrate or to just buffer (no substrate).

Pooled PI3K preparations had a protein concentration of 0.25 mg/mL. The recommended reaction has 0.06 µL per 20 µL (0.015 µg/20 µL) or 0.01125 µg/15 µL or 0.75 µg/mL.

Plates are read on machines with filters for Tamra. The units are mP with no enzyme controls reading app 190-220 mP units. Fully active enzyme reduces fluorescence polarization down to 70-100 mP after 30 minutes. An active cpd raises the mP values halfway to control or to 120-150 mP units. Results are presented in Tables 1 and 2.

Example 67 mTOR Kinase Assay Methods

Human TOR assays (See Toral-Barza, et al. *Biochem Biophys. Res. Commun.* 2005 Jun. 24; 332(1):304-10) with purified enzyme are performed in 96-well plates by DELFIA format as follows. Enzymes are first diluted in kinase assay buffer (10 mM Hepes (pH 7.4), 50 mM NaCl, 50 mM b-glycerophosphate, 10 mM MnCl2, 0.5 mM DTT, 0.25 mM microcystin LR, and 100 mg/mL BSA). To each well, 12 mL of the diluted enzyme is mixed briefly with 0.5 mL test inhibitor or control vehicle dimethylsulfoxide (DMSO). The kinase reaction is initiated by adding 12.5 mL kinase assay buffer containing ATP and His6-S6K to give a final reaction volume of 25 mL containing 800 ng/mL FLAG-TOR, 100 mM ATP and 1.25 mM His6-S6K. The reaction plate is incubated for 2 hours (linear at 1-6 hours) at room temperature with gentle shaking and then terminated by adding 25 mL Stop buffer (20 mM Hepes (pH 7.4), 20 mM EDTA, 20 mM EGTA). The DELFIA detection of the phosphorylated (Thr-389) His6-S6K is performed at room temperature using a monoclonal anti-P(T389)-p70S6K antibody (1A5, Cell Signaling) labeled with Europium-N1-ITC (Eu) (10.4 Eu per antibody, PerkinElmer). The DELFIA Assay buffer and Enhancement solution can be purchased from PerkinElmer. 45 mL of the terminated kinase reaction mixture is transferred to a MaxiSorp plate (Nunc) containing 55 mL PBS. The His6-S6K is allowed to attach for 2 hours after which the wells are aspirated and washed once with PBS. 100 mL of DELFIA Assay buffer with 40 ng/mL Eu-P(T389)-S6K antibody is added. The antibody binding is continued for 1 hour with gentle agitation. The wells are then aspirated and washed 4 times with PBS containing 0.05% Tween-20 (PBST). 100 mL of DELFIA Enhancement solution is added to each well and the plates are read in a PerkinElmer Victor model plate reader. Data obtained is used to calculate enzymatic activity and enzyme inhibition by potential inhibitors.

Example 68

Rat1-IGF1 Assay Methods for in vitro IGF-1 Induction Experiments

Rat1 cells are plated in 6-well culture plates and serum-starved for 24 hours. Serum-starved cells are treated either with control vehicle or with various concentrations of 17-HWT for 2 hours, stimulated by IGF-1 (100 ng/mL) for 30 minutes. Total cellular lysates are prepared using NuPAGE-LDS sample buffer (Invitrogen), sonicated and then clarified by centrifugation. Equal amounts of proteins are subject to immunoblotting analysis using NuPAGE electrophoresis system and probed with phosphor-AKT (S473), total AKT antibodies (Signaling Technology).

Example 69

Tumor Cell Growth Assays

Human tumor cell are all obtained from ATCC, and are cultured using standard cell culture methods. Cells are plated in 96-well culture plates at 1000 to 3000 cells per well. One day following plating, cells are treated with various doses of PI3K inhibitor Compound 4 or Compound 5 alone or with a low constant dose of MEK inhibitor 2-(2-chloro-4-iodoanilino)-N-(cycloprorylmethoxy-3,4-difluobenzamide) (1 µg/ml) or UO126 (5 µg/ml). UO126 is also known as 1,4-diamino-2,3-dicyano-1,4-bis[2-aminophenylthio]butadiene. In some experiments, cells are treated alone with various doses of the MEK inhibitor (2-(2-chloro-4-iodoanilino)-N-(cycloprorylmethoxy-3,4-difluobenzamide)), or HER2/neu inhibitor HKI-272, or mTOR inhibitor CCI-779, or with a low constant dose of Compound 4 (0.1 µg/ml). In all combination assays, the single and combination treatments are performed in the same 96-well plate along with control wells treated with vehicle (DMSO) or alone with the same dose of second drug included in combination. In addition, a control combination is also performed on the same assay plate in which the low dose drug used in experimental combinations is combined with itself to assess assay variability. Three days after drug treatment, viable cell densities are determined by metabolic conversion (by viable cells) of the dye MTS, an established cell proliferation assay. The assays are performed using an assay kit purchased from Promega Corp. (Madison, Wis.) following the protocol supplied with the kit. The MTS assay results are read in a 96-well plate reader by measuring absorbance at 490 nm. The effect of each treatment is calculated as percent of control growth relative to the vehicle DMSO-treated cells grown in the same culture plate.

Data Analysis and Calculation of Synergy

For each combination growth inhibition experiment, dose response curves of the drug alone and the combination are generated. To assess synergy, the combination dose curve is normalized by the value obtained with the second drug alone using the formula [% growth (combination)/% growth (second drug alone)]×100 to generate a normalized combination dose curve. If a normalized dose curve overlaps the curve of the single drug, the combination activity is determined as additive growth inhibition. If a normalized dose curve exhibits greater inhibitions relative to the corresponding single treatments, the combination activity is determined as synergistic growth inhibition. In each experiment, data from the control combination demonstrated fully additive growth inhibition curves.

Western Blot Analysis

Cells are plated in 6-well culture plates. 24 hr later, cells are treated with indicated single agents or combined agents for 16 hr in full growth media. Protein lysates are prepared for Western blot analysis as previously described in Yu, K., et al., *Endocr. Relat. Cancer.* 2001 September :8(3) 249-58.

Apoptosis Assay

Cells are plated in a 96-well plate at a density of 3000 cells per well. 24 hr later cells are treated with single agent or combination as indicated. Apoptosis is measured at 24 hr and 48 hr post drug treatment by Apo-ONE Caspase-3/7 assay kit (cat # G7791, Promega Corp.) following the protocol provided by the vendor. Assay mix is added to cells and incubated at room temperature for 3 hours with gentle mixing using a plate shaker. The fluorescence of each well is read using the Victor Wallac Plate Reader. Each experimental plate contains blank wells (without cells) as background fluorescence that is subtracted from all wells to obtain experimental values. Data are expressed as relative fluorescent units (RFLU) or as Apo-ONE units.

We claim:
1. A compound selected from the group consisting of:
(1E,4S,4aR,5R,6aS,7S,9aR)-1-[(diethylamino)methylene]-7,11-dihydroxy-4-(methoxymethyl)-4a,6a-dimethyl-2,10-dioxo-1,2,4,4a,5,6,6a,7,8,9,9a,10-dodecahydroindeno[4,5-h]isochromen-5-yl acetate;
(1E,4S,4aR,5R,6aS,7S,9aR)-7,11-dihydroxy-4-(methoxymethyl)-4a,6a-dimethyl-2,10-dioxo-1-(Pyrrolidin-1-ylmethylene)-1,2,4,4a,5,6,6a,7,8,9,9a,10-dodecahydroindeno[4,5-h]isochromen-5-yl acetate;
(1E,4S,4aR,5R,6aS,7S,9aR)-1-(anilinomethylene)-7,11-dihydroxy-4-(methoxymethyl)-4a,6a-dimethyl-2,10-dioxo-1,2,4,4a,5,6,6a,7,8,9,9a,10-dodecahydroindeno[4,5-h]isochromen-5-yl acetate;
(1E,4S,4aR,5R,6aS,7S)-1-{[tert-butyl(2-hydroxyethyl)amino]methylene}-7,11-dihydroxy-4-(methoxymethyl)-4a,6a-dimethyl-2,10-dioxo-1,2,4,4a,5,6,6a,7,8,9,9a,10-dodecahydroindeno[4,5-h]isochromen-5-yl acetate;
(1E,4S,4aR,5R,6aS,7S)-1-{[[3-(dimethylamino)propyl](methyl)amino]methylene}-7,11-dihydroxy-4-(methoxymethyl)-4a,6a-dimethyl-2,10-dioxo-1,2,4,4a,5,6,6a,7,8,9,9a,10-dodecahydroindeno[4,5-h]isochromen-5-yl acetate;
(1E,4S,4aR,5R,6aS,7S)-7,11-dihydroxy-4-(methoxymethyl)-4a,6a-dimethyl-1-{[methyl(1-methylpyrrolidin-3-yl)amino]methylene}-2,10-dioxo-1,2,4,4a,5,6,6a,7,8,9,9a,10-dodecahydroindeno[4,5-h]isochromen-5-yl acetate;
(1E,4S,4aR,5R,6aS,7S)-1-[(4-cyclohexylpiperazin-1-yl)methylene]-7,11-dihydroxy-4-(methoxymethyl)-4a,6a-dimethyl-2,10-dioxo-1,2,4,4a,5,6,6a,7,8,9,9a,10-dodecahydroindeno[4,5-h]isochromen-5-yl acetate;
(1E,4S,4aR,5R,6aS,7S)-1-{([butyl(methyl)amino]methylene}-7,11-dihydroxy-4-(methoxymethyl)-4a,6a-dimethyl-2,10-dioxo-1,2,4,4a,5,6,6a,7,8,9,9a,10-dodecahydroindeno[4,5-h]isochromen-5-yl acetate;
(1E,4S,4aR,5R,6aS,7S)-1-{[cyclohexyl(methyl)amino]methylene}-7,11-dihydroxy-4-(methoxymethyl)-4a,6a-dimethyl-2,10-dioxo-1,2,4,4a,5,6,6a,7,8,9,9a,10-dodecahydroindeno[4,5-h]isochromen-5-yl acetate;
(1E,4S,4aR,5R,6aS,7S)-1-[(4-benzylpiperazin-1-yl)methylene]-7,11-dihydroxy-4-(methoxymethyl)-4a,6a-dimethyl-2,10-dioxo-1,2,4,4a,5,6,6a,7,8,9,9a,10-dodecahydroindeno[4,5-h]isochromen-5-yl acetate;
(1E,4S,4aR,5R,6aS,7S)-7,11-dihydroxy-4-(methoxymethyl)-4a,6a-dimethyl-2,10-dioxo-1-(piperidin-1-ylmethylene)-1,2,4,4a,5,6,6a,7,8,9,9a,10-dodecahydroindeno[4,5-h]isochromen-5-yl acetate;
(1E,4S,4aR,5R,6aS,7S)-1-(3,4-dihydroisoquinolin-2(1H)-ylmethylene)-7,11-dihydroxy-4-(methoxymethyl)-4a,6a-dimethyl-2,10-dioxo-1,2,4,4a,5,6,6a,7,8,9,9a,10-dodecahydroindeno[4,5-h]isochromen-5-yl acetate;
(1E,4S,4aR,5R,6aS,7S)-7,11-dihydroxy-4-(methoxymethyl)-4a,6a-dimethyl-2,10-dioxo-1-[(4-phenylpiperazin-1-yl)methylene]-1,2,4,4a,5,6,6a,7,8,9,9a,10-dodecahydroindeno [4,5-h]isochromen-5-yl acetate;
(1E,4S,4aR,5R,6aS,7S)-7,11-dihydroxy-4-(methoxymethyl)-4a,6a-dimethyl-1-[(4-methylpiperazin-1-yl)methylene]-2,10-dioxo-1,2,4,4a,5,6,6a,7,8,9,9a,10-dodecahydroindeno [4,5-h]isochromen-5-yl acetate;

(1E,4S,4aR,5R,6aS,7S)-7,11-dihydroxy-4-(methoxymethyl)-4a,6a-dimethyl-2,10-dioxo-1-[(4-phenylpiperidin-1-yl)methylene]-1,2,4,4a,5,6,6a,7,8,9,9a,10-dodecahydroindeno [4,5-h]isochromen-5-yl acetate;
(1E,4S,4aR,5R,6aS,7S)-7-(formyloxy)-11-hydroxy-4-(methoxymethyl)-4a,6a -dimethyl-2,10-dioxo-1-(pyrrolidin-1-ylmethylene)-1,2,4,4a,5,6,6a,7,8,9,9a,10-dodecahydroindeno[4,5-h]isochromen-5-yl acetate;
(1E,4S,4aR,5R,6aS,7S)-1-[(diethylamino)methylene]-7-(formyloxy)-11-hydroxy-4-(methoxymethyl)-4a,6a-dimethyl-2,10-dioxo-1,2,4,4a,5,6,6a,7,8,9,9a,10-dodecahydroindeno[4,5-h]isochromen-5-yl acetate;
(1E,4S,4aR,5R,6aS,7S)-1-[(diethylamino)methylene]-7-(formyloxy)-11-hydroxy-4-(methoxymethyl)-4a,6a-dimethyl-2,10-dioxo-1,2,4,4a,5,6,6a,7,8,9,9a,10-dodecahydroindeno[4,5-h]isochromen-5-yl acetate;
Acetic acid 4-{[bis-(2-hydroxy-ethyl)-amino]-methylene}-6,17-dihydroxy-1-methoxymethyl-10,13-dimethyl-3,7-dioxo-1,3,4,7,10,11,12,13,14,15,16,17-dodecahydro-2-oxa-cyclopenta[a]phenanthren-11-yl ester;
Acetic acid 4-[(tert-butyl-methyl-amino)-methylene]-6,17-dihydroxy-1-methoxymethyl-10,13-dimethyl-3,7-dioxo-1,3,4,7,10,11,12,13,14,15,16,17-dodecahydro-2-oxa-cyclopenta[a]phenanthren-11-yl ester;
Acetic acid 4-{[bis-(3-dimethylamino-propyl)-amino]-methylene}-6,17-dihydroxy-1-methoxymethyl-10,13-dimethyl-3,7-dioxo-1,3,4,7,10,11,12,13,14,15,16,17-dodecahydro-2-oxa-cyclopenta[a]phenanthren-11-yl ester;
1-(11-Acetoxy-6,17-dihydroxy-1-methoxymethyl-10,13-dimethyl-3,7-dioxo-1,7,10,11,12,13,14,15,16,17-decahydro-2-oxa-cyclopenta[a]phenanthren-4-ylidenemethyl)-piperidine-4-carboxylic acid methyl ester;
1-(11-Acetoxy-6,17-dihydroxy-1-methoxymethyl-10,13-dimethyl-3,7-dioxo-1,7,10,11,12,13,14,15,16,17-decahydro-2-oxa-cyclopenta[a]phenanthren-4-ylidenemethyl)-piperidine-4-carboxylic acid;
4-[(11-Acetoxy-6,17-dihydroxy-1-methoxymethyl-10,13-dimethyl-3,7-dioxo-1,7,10,11,12,13,14,15,16,17-decahydro-2-oxa-cyclopenta[a]phenanthren-4-ylidenemethyl)-methyl-amino]-2,5-dimethyl-hex-2-enoic acid methyl ester;
Acetic acid 6,17-dihydroxy-1-methoxymethyl-4-[({3-[4-(4-methoxy-phenyl)-piperazin-1-yl]-propyl}-methyl-amino)-methylene]-10,13-dimethyl-3,7-dioxo-1,3,4,7,10,11,12,13,14,15,16,17-dodecahydro-2-oxa-cyclopenta[a]phenanthren-11-yl ester;
Acetic acid 6,17-dihydroxy-1-methoxymethyl-10,13-dimethyl-4-({methyl-[3-(4-methyl-piperazin-1-yl)-propyl]-amino}-methylene)-3,7-dioxo-1,3,4,7,10,11,12,13,14,15,16,17-dodecahydro-2-oxa-cyclopenta[a]phenanthren-11-yl ester;
Acetic acid 6,17-dihydroxy-1-methoxymethyl-10,13-dimethyl-4-{[methyl-(3-morpholin-4-yl-propyl)-amino]-methylene}-3,7-dioxo-1,3,4,7,10,11,12,13,14,15,16,17-dodecahydro-2-oxa-cyclopenta[a]phenanthren-11-yl ester;
Acetic acid 4-{[(2-benzenesulfonyl-ethyl)-(3-diethylamino-propyl)-amino]-methylene}-6,17-dihydroxy-1-methoxymethyl-10,13-dimethyl-3,7-dioxo-1,3,4,7,10,11,12,13,14,15,16,17-dodecahydro-2-oxa-cyclopenta[a]phenanthren-11-yl ester;
Acetic acid 4-{[(1-aza-bicyclo[3,3,1]non-5-ylmethyl)-benzyl-amino]-methylene}-6,17-dihydroxy-1-methoxymethyl-10,13-dimethyl-3,7-dioxo-1,3,4,7,10,11, 12,13,14,15,16,17-dodecahydro-2-oxa-cyclopenta[a] phenanthren-11-yl ester;

Acetic acid 6,17-dihydroxy-1-methoxymethyl-10,13-dimethyl-4-[4-(3-morpholin-4-yl-propyl)-piperazin-1-ylmethylene]-3,7-dioxo-1,3,4,7,10,11,12,13,14,15,16, 17-dodecahydro-2-oxa-cyclopenta[a]phenanthren-11-yl ester;

Acetic acid 4-{[(2-dimethylamino-ethyl)-methyl-amino]-methylene}-6,17-dihydroxy-1-methoxymethyl-10,13-dimethyl-3,7-dioxo-1,3,4,7,10,11,12,13,14,15,16,17-dodecahydro-2-oxa-cyclopenta[a]phenanthren-11-yl ester;

Acetic acid 4-[4-(3-dimethylamino-propyl)-piperazin-1-ylmethylene]-6,17-dihydroxy-1-methoxymethyl-10, 13-dimethyl-3,7-dioxo-1,3,4,7,10,11,12,13,14,15,16, 17-dodecahydro-2-oxa-cyclopenta[a]phenanthren-11-yl ester;

Acetic acid 6,17-dihydroxy-1-methoxymethyl-10,13-dimethyl-4-[4-(2-morpholin-4-yl-ethyl)-piperazin-1-ylmethylene]-3,7-dioxo-1,3,4,7,10,11,12,13,14,15,16, 17-dodecahydro-2-oxa-cyclopenta[a]phenanthren-11-yl ester;

Acetic acid 6,17-dihydroxy-1-methoxymethyl-10,13-dimethyl-4[4-(1-methyl-piperidin-4-yl)-piperazin-1-ylmethylene]-3,7-dioxo-1,3,4,7,10,11,12,13,14,15,16, 17-dodecahydro-2-oxa-cyclopenta[a]phenanthren-11-yl ester;

[(11-Acetoxy-6,17-dihydroxy-1-methoxymethyl-10,13-dimethyl-3,7-dioxo-1,7,10,11,12,13,14,15,16,17-decahydro-2-oxa-cyclopenta[a]phenanthren-4-ylidenemethyl)-methyl-amino]-acetic acid tert-butyl ester;

Acetic acid 4{[(2,3-dihydroxy-propyl)-methyl-amino]-methylene}-6,17-dihydroxy-1-methoxymethyl-10,13-dimethyl-3,7-dioxo-1,3,4,7,10,11,12,13,14,15,16,17-dodecahydro-2-oxa-cyclopenta[a]phenanthren-11-yl ester;

4-[(11-Acetoxy-6,17-dihydroxy-1-methoxymethyl-10, 13-dimethyl-3,7-dioxo-1,7,10,11,12,13,14,15,16,17-decahydro-2-oxa-cyclopenta[a]phenanthren-4-ylidenemethyl)-methyl-amino]-butyric acid;

1-(11-Acetoxy-6,17-dihydroxy-1-methoxymethyl-10,13-dimethyl-3,7-dioxo-1,7,10,11,12,13,14,15,16,17-decahydro-2-oxa-cyclopenta[a]phenanthren-4-ylidenemethyl)-azetidine-2-carboxylic acid;

1-(11-Acetoxy-6,17-dihydroxy-1-methoxymethyl-10,13-dimethyl-3,7-dioxo-1,7,10,11,12,13,14,15,16,17-decahydro-2-oxa-cyclopenta[a]phenanthren-4-ylidenemethyl)-pyrrolidine-2-carboxylic acid methyl ester;

Acetic acid 4-{[benzyl-(2-cyano-ethyl)-amino]-methylene}-6,17-dihydroxy-1-methoxymethyl-10,13-dimethyl-3,7-dioxo-1,3,4,7,10,11,12,13,14,15,16,17-dodecahydro-2-oxa-cyclopenta[a]phenanthren-11-yl ester;

Acetic acid 4-{[(2-diethylamino-ethyl)-methyl-amino]-methylene}-6,17-dihydroxy-1-methoxymethyl-10,13-dimethyl-3,7-dioxo-1,3,4,7,10,11,12,13,14,15,16,17-dodecahydro-2-oxa-cyclopenta[a]phenanthren-11-yl ester;

Acetic acid 4-{[(2-diethylamino-ethyl)-ethyl-amino]-methylene}-6,17-dihydroxy-1-methoxymethyl-10,13-dimethyl-3,7-dioxo-1,3,4,7,10,11,12,13,14,15,16,17-dodecahydro-2-oxa-cyclopenta[a]phenanthren-11-yl ester;

Acetic acid 4-{[benzyl-(2-dimethylamino-ethyl)-amino]-methylene}-6,17-dihydroxy-1-methoxymethyl-10,13-dimethyl-3,7-dioxo-1,3,4,7,10,11,12,13,14,15,16,17-dodecahydro-2-oxa-cyclopenta[a]phenanthren-11-yl ester;

Acetic acid 6,17-dihydroxy-1-methoxymethyl-10,13-dimethyl-3,7-dioxo-4-(4-oxo-piperidin-1-ylmethylene)-1,3,4,7,10,11,12,13,14,15,16,17-dodecahydro-2-oxa-cyclopenta[a]phenanthren-11-yl ester;

4-{[(2-Dimethylamino-ethyl)-ethyl-amino]-methylene}-6,17-dihydroxy-1-methoxymethyl-10,13-dimethyl-10, 11,12,13,14,15,16,17-octahydro-1H,4H-2-oxa-cyclopenta[a]phenanthrene-3,7-dione;

Acetic acid 4-{[(2-dimethylamino-ethyl)-ethyl-amino] methylene}-6,17-dihydroxy-1-methoxymethyl-10,13-dimethyl-3,7-dioxo-1,3,4,7,10,11,12,13,14,15,16,17-dodecahydro-2-oxa-cyclopenta[a]phenanthren-11-yl ester;

Acetic acid 4-[1,4']bipiperidinyl-1'-ylmethylene-6,17-dihydroxy-1-methoxymethyl-10,13-dimethyl-3,7-dioxo-1,3,4,7,10,11,12,13,14,15,16,17-dodecahydro-2-oxa-cyclopenta[a]phenanthren-11-yl ester;

Acetic acid 6,17-dihydroxy-1-methoxymethyl-10,13-dimethyl-4-morpholin-4-ylmethylene-3,7-dioxo-1,3,4, 7,10,11,12,13,14,15,16,17-dodecahydro-2-oxa-cyclopenta[a]phenanthren-11-yl ester;

Propionic acid 4-{[(2-dimethylamino-ethyl)-methyl-amino]-methylene}-6,17-dihydroxy-1-methoxymethyl-10,13-dimethyl-3,7-dioxo-1,3,4,7,10,11,12,13, 14,15,16,17-dodecahydro-2-oxa-cyclopenta[a] phenanthren-11-yl ester;

(1E,4S,4aR,5R,6aS,7S,9aR)-1-[(diethylamino)methylene]-5,7,11-trihydroxy-4-(methoxymethyl)-4a,6a-dimethyl-4a,5,6,6a,7,8,9,9a-octahydroindeno[4,5-h]isochromene-2,10(1H,4H)-dione;

Acetic acid 4-butylsulfanylmethylene-6,17-dihydroxy-1-methoxymethyl-10,13-dimethyl-3,7-dioxo-1,3,4,7,10, 11,12,13,14,15,16,17-dodecahydro-2-oxa-cyclopenta [a]phenanthren-11-yl ester;

7-Pegylated di-(1E,4S,4aR,5R,6aS,7S)-1-{[[3-(dimethylamino)propyl](methyl)amino]methylene}-7,11-dihydroxy-4-(methoxymethyl)-4a,6a-dimethyl-2,10-dioxo-1,2,4,4a,5,6,6a,7,8,9,9a,10-dodecahydroindeno[4,5-h] isochromen-5-yl acetate;

(1E,4S,4aR,5R,6aS,7S)-1-{[[3-(dimethylamino)propyl](methyl)amino]methylene}-5,7,11-trihydroxy-4-(methoxymethyl)-4a,6a-dimethyl-4a,5,6,6a,7,8,9,9a-octahydroindeno[4,5-h]isochromene-2,10(1H,4H)-dione;

(1E,4S,4αR,5R,6αS,7S,9αR)-1-({tert-butyl[2-(dimethylamino)ethyl]amino}methylene)-7,11-dihydroxy-4-(methoxymethyl)-4, α6α-dimethyl-2,10-dioxo-1,2,4, 4α,5,6,6α,7,8,9,9α,10-dodecahydroindeno[4,5-h] isochromen-5-yl acetate;

Butanoic acid 4-{[(2-dimethylamino-propyl)-methyl-amino]-methylene}-6,17-dihydroxy-1-methoxymethyl-10,13-dimethyl-3,7-dioxo-1,3,4,7,10,11,12,13, 14,15,16,17-dodecahydro-2-oxa-cyclopenta[a] phenanthren-11-yl ester;

Acetic acid 4-{[(2-dimethylamino-propyl)-ethyl-amino] methylene}-6,17-dihydroxy-1-methoxymethyl-10,13-dimethyl-3,7-dioxo-1,3,4,7,10,11,12,13,14,15,16,17-dodecahydro-2-oxa-cyclopenta[a]phenanthren-11-yl ester (1E,4S,4aR,5R,6aS,7S,9aR)-1-({4-[2-(2,5-dioxo-2,5-dihydro-1H-pyrrol-1-yl)ethyl]piperazin-1-yl}methylene)-7,11-dihydroxy-4-(methoxymethyl)-4a, 6a-dimethyl-2,10-dioxo-1,2,4,4a,5,6,6a,7,8,9,9a,10-dodecahydroindeno[4,5-h]isochromen-5-yl acetate;

(1Z,4S,4aR,5R,6aS,7S)-7,11-dihydroxy-4-(methoxymethyl)-4a,6a-dimethyl-2,10-dioxo-1{12-oxo-16-[(3aR,4R,6aS)-2-oxohexahydro-1H-thieno[3,4-d]imidazol-4-yl]-5,8-dioxa-2,11-diazahexadec-1-ylidene}-1,2,4,4a,5,6,6a,7,8,9,9a,10-dodecahydroindeno[4,5-h]isochromen-5-yl acetate;

7-Pegylated (1E,4S,4aR,5R,6aS,7S,9aR)-1-[(diethylamino)methylene]-7,11-dihydroxy-4-(methoxymethyl)-4a,6a-dimethyl-2,10-dioxo-1,2,4,4a,5,6,6a,7,8,9,9a,10-dodecahydroindeno[4,5-h]isochromen-5-yl acetate;

(1Z,4S,4aR,5R,6aS,7S)-1-{[t-butylamino]methylene}-7,11-dihydroxy-4-(methoxymethyl)-4a,6a-dimethyl-2,10-dioxo-1,2,4,4a,5,6,6a,7,8,9,9a,10-dodecahydroindeno[4,5-h]isochromen-5-yl acetate;

(1Z,4S,4aR,5R,6aS,7S)-7,11-dihydroxy-1-{[(2-mercaptoethyl)amino]methylene}-4-(methoxymethyl)-4a,6a-dimethyl-2,10-dioxo-1,2,4,4a,5,6,6a,7,8,9,9a,10-dodecahydroindeno[4,5-h]isochromen-5-yl acetate;

(1Z,4S,4aR,5R,6aS,7S,9aR)-1-[(ethylamino)methylene]-7,11-dihydroxy-4-in-(methoxymethyl)-4a,6a-dimethyl-2,10-dioxo-1,2,4,4a,5,6,6a,7,8,9,9a,10-dodecahydroindeno[4,5-h]isochromen-5-yl acetate;

and salts, solvates, and hydrates thereof.

2. The compound of claim 1 selected from the group consisting of:

(1E,4S,4aR,5R,6aS,7S,9aR)-1-[(diethylamino)methylene]-7,11-dihydroxy-4-(methoxymethyl)-4a,6a-dimethyl-2,10-dioxo-1,2,4,4a,5,6,6a,7,8,9,9a,10-dodecahydroindeno[4,5-h]isochromen-5-yl acetate;

(1E,4S,4aR,5R,6aS,7S,9aR)-7,11-dihydroxy-4-(methoxymethyl)-4a,6a-dimethyl-2,10-dioxo-1-(Pyrrolidin-1-ylmethylene)-1,2,4,4a,5,6,6a,7,8,9,9a,10-dodecahydroindeno[4,5-h]isochromen-5-yl acetate;

(1E,4S,4aR,5R,6aS,7S,9aR)-1-(anilinomethylene)-7,11-dihydroxy-4-(methoxymethyl)-4a,6a-dimethyl-2,10-dioxo-1,2,4,4a,5,6,6a,7,8,9,9a,10-dodecahydroindeno[4,5-h]isochromen-5-yl acetate;

(1E,4S,4aR,5R,6aS,7S)-1-{[tert-butyl(2-hydroxyethyl)amino]methylene}-7,11-dihydroxy-4-(methoxymethyl)-4a,6a-dimethyl-2,10-dioxo-1,2,4,4a,5,6,6a,7,8,9,9a,10-dodecahydroindeno[4,5-h]isochromen-5-yl acetate;

(1E,4S,4aR,5R,6aS,7S)-1-{[[3-(dimethylamino)propyl](methyl)amino]methylene}-7,11-dihydroxy-4-(methoxymethyl)-4a,6a-dimethyl-2,10-dioxo-1,2,4,4a,5,6,6a,7,8,9,9a,10-dodecahydroindeno[4,5-h]isochromen-5-yl acetate;

(1E,43,4aR,5R,6aS,7S)-7,11-dihydroxy-4-(methoxymethyl)-4a,6a-dimethyl-1-{[methyl(1-methylpyrrolidin-3-yl)amino]methylene}-2,10-dioxo-1,2,4,4a,5,6,6a,7,8,9,9a,10-dodecahydroindeno[4,5-h]isochromen-5-yl acetate;

(1E,4S,4aR,5R,6aS,7S)-1-[(4-cyclohexylpiperazin-1-yl)methylene]-7,11-dihydroxy-4-(methoxymethyl)-4a,6a-dimethyl-2,10-dioxo-1,2,4,4a,5,6,6a,7,8,9,9a,10-dodecahydroindeno[4,5-h]isochromen--5-yl acetate;

(1E,4S,4aR,5R,6aS,7S)-1-{[butyl(methyl)amino]methylene}-7,11-dihydroxy-4-(methoxymethyl)-4a,6a-dimethyl-2,10-dioxo-1,2,4,4a,5,6,6a,7,8,9,9a,10-dodecahydroindeno[4,5-h]isochromen-5-yl acetate;

(1E,4S,4aR,5R,6aS,7S)-1-{[cyclohexyl(methyl)amino]methylene}-7,11-dihydroxy-4-(methoxymethyl)-4a6a-dimethyl-2,10-dioxo-1,2,4,4a,5,6,6a,7,8,9,9a,10-dodecahydroindeno[4,5-h]isochromen-5-yl acetate;

(1E,4S,4aR,5R,6aS,7S)-1-[(4-benzylpiperazin-1-yl)methylene]-7,11-dihydroxy-4-(methoxymethyl)-4a,6a-dimethyl-2,10-dioxo-1,2,4,4a,5,6,6a,7,6,9,9a,10-dodecahydroindeno[4,5-h]isochromen-5-yl acetate;

(1E,4S,4aR,5R,6aS,7S)-7,11-dihydroxy-4-(methoxymethyl)-4a,6a-dimethyl-2,10-dioxo-1-(piperidin-1-ylmethylene)-1,2,4,4a,5,6,6a,7,8,9,9a,10dodecahydroindeno[4,5-h]isochromen-5-yl acetate;

(1E,4S,4aR,5R,6aS,7S)-1-(3,4-dihydroisoquinolin-2(1H)-ylmethylene)-7,11-dihydroxy-4-(methoxymethyl)-4a,6a-dimethyl-2,10-dioxo-1,2,4,4a,5,6,6a,7,8,9,9a,10-dodecahydroindeno[4,5-h]isochromen-5-yl acetate;

(1E,4S,4aR,5R,6aS,7S)-7,11-dihydroxy-4-(methoxymethyl)-4a,6a-dimethyl-2,10-dioxo-1-[(4-phenylpiperazin-1-yl)methylene]-1,2,4,4a,5,6,6a,7,8,9,9a,10-dodecahydroindeno [4,5-h]isochromen-5-yl acetate;

(1E,4S,4aR,5R,6aS,7S)-7,11-dihydroxy-4-(methoxymethyl)-4a,6a-dimethyl-1-[(4-methylpiperazin-1-yl)methylene]-2,10-dioxo-1,2,4,4a,5,6,6a,7,8,9,9a,10-dodecahydroindeno [4,5-h]isochromen-5-yl acetate;

(1E,4S,4aR,5R,6aS,7S)-7,11-dihydroxy-4-(methoxymethyl)-4a,6a-dimethyl-2,10-dioxo-1-[(4-phenylpiperidin-1-yl)methylene]-1,2,4,4a,5,6,6a,7,8,9,9a,10-dodecahydroindeno [4,5-h]isochromen-5-yl acetate;

(1E,4S,4aR,5R,6aS,7S)-7-(formyloxy)-11-hydroxy-4-(methoxymethyl)-4a,6a-dimethyl-2,10-dioxo-1-(pyrrolidin-1-ylmethylene)-1,2,4,4a,5,6,6a,7,8,9,9a,10-dodecahydroindeno[4,5-h]isochromen-5-yl acetate;

(1E,4S,4aR,5R,6aS,7S)-1-[(diallylamino)methylene]-7-(formyloxy)-11-hydroxy-4-(methoxymethyl)-4a,6a-dimethyl-2,10dioxo-1,2,4,4a,5,6,6a,7,8,9,9a,10-dodecahydroindeno[4,5-h]isochromen-5-yl acetate;

(1E,4S,4aR,5R,6aS,7S)-1-[(diethylamino)methylene]-7-(formyloxy)-11-hydroxy-4-(methoxymethyl)-4a,6a-dimethyl-2,10-dioxo-1,2,4,4a,5,6,6a,7,8,9,9a,10-dodecahydroindeno[4,5-h]isochromen-5-yl acetate;

Acetic acid 4-{[bis-(2-hydroxy-ethyl)-amino]-methylene}-6,17-dihydroxy-1-methoxymethyl-10,13-dimethyl-3,7-dioxo-1,3,4,7,10,11,12,13,14,15,16,17-dodecahydro-2-oxa-cyclopenta[a]phenanthren-11-yl ester;

Acetic acid 4-[(tert-butyl-methyl-amino)-methylene]-6,17-dihydroxy-1-methoxymethyl-10,13-dimethyl-3,7-dioxo-1,3,4,7,10,11,12,13,14,15,16,17-dodecahydro-2-oxa-cyclopenta[a]phenanthren-11-yl ester;

Acetic acid 4-{[bis-(3-dimethylamino-propyl)-amino]-methylene}-6,17-dihydroxy-1-methoxymethyl-10,13-dimethyl-3,7-dioxo-1,3,4,7,10,11,12,13,14,15,16,17-dodecahydro-2-oxa-cyclopenta[a]phenanthren-11-yl ester;

1-(11-Acetoxy-6,17-dihydroxy-1-methoxymethyl-10,13-dimethyl-3,7-dioxo-1,7,10,11,12,13,14,15,16,17-decahydro-2-oxa-cyclopenta[a]phenanthren-4-ylidenemethyl)-piperidine-4-carboxylic acid methyl ester;

1-(11-Acetoxy-6,17-dihydroxy-1-methoxymethyl-10,13-dimethyl-3,7-dioxo-1,7,10,11,12,13,14,15,16,17-decahydro-2-oxa-cyclopenta[a]phenanthren-4-ylidenemethyl)-piperidine-4-carboxylic acid;

4-[(11-Acetoxy-6,17-dihydroxy-1-methoxymethyl-10,13-dimethyl-3,7-dioxo-1,7,10,11,12,13,14,15,16,17-decahydro-2-oxa-cyclopenta[a]phenanthren-4-ylidenemethyl)-methyl-amino]-2,5-dimethyl-hex-2-enoic acid methyl ester;

Acetic acid 6,17-dihydroxy-1-methoxymethyl-4-[({3-[4-(4-methoxy-phenyl)-piperazin-1-yl]-propyl}-methyl-amino)-methylene]-10,13-dimethyl-3,7-dioxo-1,3,4,7,10,11,12,13,14,15,16,17-dodecahydro-2-oxa-cyclopenta[a]phenanthren-11-yl ester;

Acetic acid 6,17-dihydroxy-1-methoxymethyl-10,13-dimethyl-4-({methyl-[3-(4-methyl-piperazin-1-yl)-propyl]-amino}-methylene)-3,7-dioxo-1,3,4,7,10,11,12,13,14,15,16,17-dodecahydro-2-oxa-cyclopenta[a]phenanthren-11-yl ester;

Acetic acid 6,17-dihydroxy-1-methoxymethyl-10,13-dimethyl-4-{[methyl-(3-morpholin-4-yl-propyl)-amino]-methylene}-3,7-dioxo-1,3,4,7,10,11,12,13,14,15,18,17-dodecahydro-2-oxa-cyclopenta[a]phenanthren-11-yl ester;

Acetic acid 4-{[(2-benzenesulfonyl-ethyl)-(3-diethylamino-propyl)-amino]-methylene}-6,17-dihydroxy-1-methoxymethyl-10,13-dimethyl-3,7-dioxo-1,3,4,7,10,11,12,13,14,15,16,17-dodecahydro-2-oxa-cyclopenta[a]phenanthren-11-yl ester;

Acetic acid 4-{[(1-aza-bicyclo[3.3.1]non-5-ylmethyl)-benzyl-amino]-methylene}-6,17-dihydroxy-1-methoxymethyl-10,13-dimethyl-3,7-dioxo-1,3,4,7,10,11,12,13,14,15,16,17-dodecahydro-2-oxa-cyclopenta[a]phenanthren-11-yl ester;

Acetic acid 6,17-dihydroxy-1-methoxymethyl-10,13-dimethyl-4-[4-(3-morpholin-4-yl-propyl)-piperazin-1-ylmethylene]-3,7-dioxo-1,3,4,7,10,11,12,13,14,15,16,17-dodecahydro-2-oxa-cyclopenta[a]phenanthren-11-yl ester;

Acetic acid 4-{[(2-dimethylamino-ethyl)-methyl-amino]-methylene}-6,17-dihydroxy-1-methoxymethyl-10,13-dimethyl-3,7-dioxo-1,3,4,7,10,11,12,13,14,15,16,17-dodecahydro-2-oxa-cyclopenta[a]phenanthren-11-yl ester;

Acetic acid 4-[4-(3-dimethylamino-propyl)-piperazin-1-ylmethylene]-6,17-dihydroxy-1-methoxymethyl-10,13-dimethyl-3,7-dioxo-1,3,4,7,10,11,12,13,14,15,16,17-dodecahydro-2-oxa-cyclopenta[a]phenanthren-11yl ester;

Acetic acid 6,17-dihydroxy-1-methoxymethyl-10,13-dimethyl-4-[4-(2-morpholin-4-yl-ethyl)-piperazin-1-ylmethylene]-3,7-dioxo-1,3,4,7,10,11,12,13,14,15,16,17-dodecahydro-2-oxa-cyclopenta[a]phenanthren-11-yl ester;

Acetic acid 6,17-dihydroxy-1-methoxymethyl-10,13-dimethyl-4-[4-(1-methyl-piperidin-4-yl)-piperazin-1-ylmethylene]-3,7-dioxo-1,3,4,7,10,11,12,13,14,15,16,17-dodecahydro-2-oxa-cyclopenta[a]phenanthren-11-yl ester;

[(11-Acetoxy-6,17-dihydroxy-1-methoxymethyl-10,13-dimethyl-3,7-dioxo-1,7,10,11,12,13,14,15,16,17-decahydro-2-oxa-cyclopenta[a]phenanthren-4-ylidenemethyl)-methyl-amino]-acetic acid tert-butyl ester;

Acetic acid 4-{[(2,3-dihydroxy-propyl)-methyl-amino]-methylene}-6,17-dihydroxy-1-methoxymethyl-10,13-dimethyl-3,7-dioxo-1,3,4,7,10,11,12,13,14,15,16,17-dodecahydro-2-oxa-cyclopenta[a]phenanthren-11-yl ester;

4[(11-Acetoxy-6,17-dihydroxy-1-methoxymethyl-10,13-dimethyl-3,7-dioxo-1,7,10,11,12,13,14,15,16,17-decahydro-2-oxa-cyclopenta[a]phenanthren-4-ylidenemethyl)-methyl-amino]-butyric acid;

1-(11-Acetoxy-6,17-dihydroxy-1-methoxymethyl-10,13-dimethyl-3,7-dioxo-1,7,10,11,12,13,14,15,16,17-decahydro-2-oxa-cyclopenta[a]phenanthren-4-ylidenemethyl)-azetidine-2-carboxylic acid;

1-(11-Acetoxy-6,17-dihydroxy-1-methoxymethyl-10,13-dimethyl-3,7-dioxo-1,7,10,11,12,13,14,15,16,17-decahydro-2-oxa-cyclopenta[a]phenanthren-4-ylidenemethyl)-pyrrolidine-2-carboxylic acid methyl ester;

Acetic acid 4-{[benzyl-(2-cyano-ethyl)-amino]-methylene}-6,17-dihydroxy-1-methoxymethyl-10,13-dimethyl-3,7-dioxo-1,3,4,7,10,11,12,13,14,15,16,17-dodecahydro-2-oxa-cyclopenta[a]phenanthren-11-yl ester;

Acetic acid 4-{[(2-diethylamino-ethyl)-methyl-amino]-methylene}-6,17-dihydroxy-1-methoxymethyl-10,13-dimethyl-3,7-dioxo-1,3,4,7,10,11,12,13,14,15,16,17-dodecahydro-2-oxa-cyclopenta[a]phenanthren-11-yl ester;

Acetic acid 4-{[(2-diethylamino-ethyl)-ethyl-amino]-methylene}-6,17-dihydroxy-1-methoxymethyl-10,13-dimethyl-3,7-dioxo-1,3,4,7,10,11,12,13,14,15,16,17-dodecahydro-2-oxa-cyclopenta[a]phenanthren-11-yl ester;

Acetic acid 4-{[benzyl-(2-dimethylamino-ethyl)-amino]-methylene}-6,17-dihydroxy-1-methoxymethyl-10,13-dimethyl-3,7-dioxo-1,3,4,7,10,11,12,13,14,15,16,17-dodecahydro-2-oxa-cyclopenta[a]phenanthren-11-yl ester;

Acetic acid 6,17-dihydroxy-1-methoxymethyl-10,13-dimethyl-3,7-dioxo-4-(4-oxo-piperidin-1-ylmethylene)-1,3,4,7,10,11,12,13,14,15,16,17-dodecahydro-2-oxa-cyclopenta[a]phenanthren-11-yl ester;

4-{[(2-Dimethylamino-ethyl)-ethyl-amino]-methylene}-6,17-dihydroxy-1-methoxymethyl-10,13-dimethyl-10,11,12,13,14,15,16,17-octahydro-1H,4H-2-oxa-cyclopenta[a]phenanthrene-3,7-dione;

Acetic acid 4-{[(2-dimethylamino-ethyl)-ethyl-amino]-methylene}-6,17-dihydroxy-1-methoxymethyl-10,13-dimethyl-3,7-dioxo-1,3,4,7,10,11,12,13,14,15,16,17-dodecahydro-2-oxa-cyclopenta[a]phenanthren-11-yl ester;

Acetic acid 4-[1,4']bipiperidinyl-1'-ylmethylene-6,17-dihydroxy-1-methoxymethyl-10,13-dimethyl-3,7-dioxo-1,3,4,7,10,11,12,13,14,15,16,17-dodecahydro-2-oxa-cyclopenta[a]phenanthren-11-yl ester;

Acetic acid 6,17-dihydroxy-1-methoxymethyl-10,13-dimethyl-4-morpholin-4-ylmethylene-3,7-dioxo-1,3,4,7,10,11,12,13,14,15,16,17-dodecahydro-2-oxa-cyclopenta[a]phenanthren-11-yl ester;

Propionic acid 4-{[(2-dimethylamino-ethyl)-methyl-amino]-methylene}-6,17-dihydroxy-1-methoxymethyl-10,13-dimethyl-3,7-dioxo-1,3,4,7,10,11,12,13,14,15,16,17-dodecahydro-2-oxa-cyclopenta[a]phenanthren-11-yl ester;

(1E,4S,4aR,5R,6aS,7S,9aR)-1-[(diethylamino)methylene]-5,7,11-trihydroxy-4-(methoxymethyl)-4a,6a-dimethyl-4a,5,6,6a,7,8,9,9a-octahydroindeno[4,5-h]isochromene-2,10(1H,4H)-dione;

Acetic acid 4-butylsulfanylmethylene-6,17-dihydroxy-1-methoxymethyl-10,13-dimethyl-3,7-dioxo-1,3,4,7,10,11,12,13,14,15,16,17-dodecahydro-2-oxa-cyclopenta[a]phenanthren-11-yl ester;

7-Pegylated di-(1E,4S,4aR,5R,6aS,7S)-1-{[[3-(dimethylamino)propyl](methyl)amino]methylene}-7,11-dihydroxy-4-(methoxymethyl)-4a,6a-dimethyl-2,10-dioxo-1,2,4,4a,5,6,6a,7,8,9,9a,10-dodecahydroindeno[4,5-h]isochromen-5-yl acetate;

(1E,4S,4aR,5R,6aS,7S)-1-{[[3-(dimethylamino)propyl](methyl)amino]methylene}-5,7,11-trihydroxy-4-(methoxymethyl)-4a,6a-dimethyl-4a,5,6,6a,7,8,9,9a-octahydroindeno[4,5-h]isochromene-2,10(1H,4H)-dione;

(1E,4S,4αR,5R,6α,7S,9α-1-({tert-butyl[2-(dimethylamino)ethyl]amino}methylene)-7,11-dihydroxy-4-

(methoxymethyl)-4α,6α-dimethyl-2,10-dioxo-1,2,4,
4α,5,6,6α,7,8,9,9a,10-dodecahydroindeno[4,5-h]
isochromen-5-yl acetate;
Butanoic acid 4-{[(2-dimethylamino-propyl)-methyl-amino]-methylene}-6,17-dihydroxy-1-methoxym-ethyl-10,13-dimethyl-3,7-dioxo-1,3,4,7,10,11,12,13,
14,15,16,17-dodecahydro-2-oxa-cyclopenta[a]
phenanthren-11-yl ester;
Acetic acid 4-{[(2-dimethylamino-propyl)-ethyl-amino]-methylene}-6,17-dihydroxy-1-methoxymethyl-10,13-dimethyl-3,7-dioxo-1,3,4,7,10,11,12,13,14,15,16,17-dodecahydro-2-oxa-cyclopenta[a]phenanthren-11-yl ester
(1E,4S,4aR,5R,6aS,7S,9aR)-1-({4-[2-(2,5-dioxo-2,5-dihydro-1H-pyrrol-1-yl]ethyl]piperazin-1-yl)methyl-ene)-7,11-dihydroxy-4-(methoxymethyl)-4a,6a-dimethyl-2,10-dioxo-1,2,4,4a,5,6,6a,7,8,9,9a,10-dodecahydroindeno[4,5-h]isochromen-5-yl acetate;
and salts, solvates, and hydrates thereof.

3. The compound of claim 2 wherein the compound is (1E,4S,4aR,5R,6aS,7S)-1-{[[3-(dimethylamino)propyl](methyl)amino]methylene}-7,11-dihydroxy-4-(methoxymethyl)-4a,6a-dimethyl-2,10-dioxo-1,2,4,4a,5,6,8a,7,8,9,9a,10-dodecahydroindeno[4,5-h]isochromen-5-yl acetate.

4. The compound of claim 1 wherein the compound is PEGylated.

5. The compound of claim 2 wherein the compound is PEGylated.

6. The compound of claim 3 wherein the compound is PEGylated.

7. A method of treating a PI3K-dependent condition, said condition selected from the group consisting of tumor cell proliferation, tumor cell growth, and tumorigenesis, comprising administering to a subject a PI3K-inhibiting amount of a compound according to claim 1.

8. A pharmaceutical composition comprising a compound according to claim 1 and a pharmaceutically acceptable carrier.

9. A method of treating tumor cell proliferation, tumor cell growth, or tumorigenesis comprising administering to a subject a pharmaceutical composition according to claim 8.

10. The method of claim 9 further comprising administering one or more agents that modulate growth factor signaling, cytokine response, and cell cycle control.

11. A method of treating tumor cell proliferation, tumor cell growth, or tumorigenesis comprising administering to a subject a pharmaceutical composition comprising a compound according to claim 1 and a pharmaceutically acceptable carrier.

12. The compound 7-Pegylated di-(1E,4S,4aR,5R,6aS,7S)-1-{[[3-(dimethylamino)propyl](methyl)amino]methylene}-7,11-dihydroxy-4-(methoxymethyl)-4a,6a-dimethyl-2,10-dioxo-1,2,4,4a,5,6,6a,7,8,9,9a,10-dodecahydroindeno[4,5-h]isochromen-5-yl acetate.

13. The method of claim 9, further comprising administering taxol.

14. The method of claim 13 further administering one or more agents that modulate growth factor signaling, cytokine response, and cell cycle control.

15. The method of claim 14, wherein the agent is selected from the group consisting of cytokines, interferon, rapamycin, pegylated rapamycin, HER2/EGFR inhibitors, MEK inhibitors, interferon-α(Intron-A), and Src kinase inhibitors.

* * * * *

UNITED STATES PATENT AND TRADEMARK OFFICE
CERTIFICATE OF CORRECTION

PATENT NO. : 7,666,901 B2
APPLICATION NO. : 11/248510
DATED : February 23, 2010
INVENTOR(S) : Zask et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 978 days.

Signed and Sealed this

Seventh Day of December, 2010

David J. Kappos
*Director of the United States Patent and Trademark Office*